US011098265B2

(12) United States Patent
Dayton et al.

(10) Patent No.: US 11,098,265 B2
(45) Date of Patent: Aug. 24, 2021

(54) SILICA ADSORBENT TREATMENT FOR REMOVAL OF CHLOROPHYLL DERIVATIVES FROM TRIACYLGLYCEROL-BASED OILS

(71) Applicant: Bunge Global Innovation, LLC, White Plains, NY (US)

(72) Inventors: Christopher Loren Gene Dayton, Jupiter, FL (US); Demetrius Michos, Clarksville, MD (US); Cristian Libanati, Silver Spring, MD (US); Chelsea Grimes, Stoney Beach, MD (US)

(73) Assignee: Bunge Global Innovation, LLC, Chesterfield, MO (US)

( * ) Notice: Subject to any disclaimer, the term of this patent is extended or adjusted under 35 U.S.C. 154(b) by 0 days.

(21) Appl. No.: 16/828,369

(22) Filed: Mar. 24, 2020

(65) Prior Publication Data
US 2020/0308505 A1 Oct. 1, 2020

Related U.S. Application Data

(60) Provisional application No. 62/824,636, filed on Mar. 27, 2019.

(51) Int. Cl.
*C11B 3/10* (2006.01)
*C11B 3/00* (2006.01)

(52) U.S. Cl.
CPC .............. *C11B 3/10* (2013.01); *C11B 3/003* (2013.01)

(58) Field of Classification Search
CPC .................................. C11B 3/20; C11B 3/003
USPC ........................................................... 554/191
See application file for complete search history.

(56) References Cited

U.S. PATENT DOCUMENTS

| 4,681,768 A | 7/1987 | Mulflur et al. |
| 4,781,864 A | 11/1988 | Pryor et al. |
| 9,295,810 B2 | 3/2016 | Hicks et al. |
| 9,493,748 B2 | 11/2016 | Soe et al. |

(Continued)

FOREIGN PATENT DOCUMENTS

| EP | 0269173 A2 | 6/1988 | |
| EP | 0558173 A1 * | 9/1993 | ............... C11B 3/10 |

(Continued)

OTHER PUBLICATIONS

International Search Report and Written Opinion for PCT/US2020/024433, dated Jul. 3, 2020, 16 pages.

(Continued)

*Primary Examiner* — Deborah D Carr
(74) *Attorney, Agent, or Firm* — Armstrong Teasdale LLP

(57) ABSTRACT

The present invention relates to a process for treating an oil comprising a chlorophyll derivative. In particular, the present disclosure relates to an improved process for removing impurities, including chlorophyll derivatives and/or trace metals, from an oil using an adsorbent comprising a silica treated with an alkali earth metal oxide, such as magnesium oxide. The process comprises contacting the oil with the adsorbent, wherein the pH of the silica is about 7 or greater, including from about 7 to about 10. The process may further comprise contacting the oil with a polypeptide having decolorase activity or a composition comprising the polypeptide, prior to contact with the adsorbent.

40 Claims, 17 Drawing Sheets

Specification includes a Sequence Listing.

(56) References Cited

U.S. PATENT DOCUMENTS

| | | |
|---|---|---|
| 2005/0130160 A1 | 6/2005 | Chew et al. |
| 2005/0186666 A1 | 8/2005 | Schneider et al. |
| 2006/0110747 A1 | 5/2006 | Ramseier et al. |
| 2008/0058262 A1 | 3/2008 | Rasochova et al. |

FOREIGN PATENT DOCUMENTS

| | | | |
|---|---|---|---|
| EP | 0558173 A1 | 9/1993 | |
| EP | 1104448 A1 * | 6/2001 | ............ C11B 3/001 |
| EP | 1104448 B1 | 5/2005 | |
| WO | 1996000787 A1 | 1/1996 | |
| WO | 2000056900 A2 | 9/2000 | |
| WO | 2005086900 A2 | 9/2005 | |
| WO | 2006077258 A1 | 7/2006 | |
| WO | 2008000632 A1 | 1/2008 | |
| WO | 2010143149 A2 | 12/2010 | |
| WO | 2013160372 A1 | 10/2013 | |
| WO | 2014098957 A2 | 6/2014 | |
| WO | WO-2014098957 A2 * | 6/2014 | ........ A61M 39/0693 |

OTHER PUBLICATIONS

Altschul et al., "Basic Local Alignment Search Tool" J. Molecular Biology, 215(3): 403-410 (1990).

Altschul et al., "Gapped BLAST and PSI-BLAST: a new generation of protein database search programs," Nucleic Acids Research, 25(17): 3389-3402 (1997).

Gunstone et al. (Editors) "The lipid handbook," 3rd Edition (2007) p. 56.

Hwang et al., "HPLC Determination of Pheophorbide a and Pyropheophorbide a in Dried Laver Product Implicated in Food Poisoning," Journal of Food Hygiene Society, Japan, 46(2): 45-48 (2005).

Meesters, G.M.H. "Encapsulation of Enzymes and Peptides," Chapter 9 in Encapsulation Technologies for Active Food Ingredients and Food Processing, Zuidam & Nedovic Editors, Springer, pp. 253-268 (2010).

Needleman et al., "A general method applicable to the search for similarities in the amino acid sequence of two proteins," Journal of Molecular Biology, 48(3): 443-453 (1970).

Rice et al., "EMBOSS: the European Molecular Biology Open Software Suite," TIG, 16(6): 276-277 (2000).

Suzuki et al., "Behavior of Chlorophyll Derivatives in Canola Oil Processing," Journal of the American Oil Chemists' Society, 70(9): 837-841 (1993).

PQ Corporation "Typical Property Data for PQ® Sorbsil R40" Product Brochure, Issue 3, Aug. 2008 (1 page).

PQ Corporation "Typical Property Data for PQ® Sorbsil R92" Product Brochure, Issue 4, Sep. 2008 (1 page).

* cited by examiner

| Seq ID | Organism of origin | Sum phorbides | Sum phytines | Pheop horbide B | Pyro pheophorbid e B | Pheo phorbide A | Pyro pheophorbide A | Pheophyti n B | Pyro pheophyti n B | Pheo phytin A | Pyro pheophyt in A |
|---|---|---|---|---|---|---|---|---|---|---|---|
| | | | | | | pH 7 | | | | | |
| CHL25 | Gossypium raimondii | 275665 | 1931477 | 110063 | nd | 87548 | 78054 | 172154 | 480011 | 501490 | 777822 |
| CHL25 | Gossypium raimondii | 217243 | 1920403 | nd | nd | 146036 | 71207 | 150671 | 445076 | 499908 | 824748 |
| CHL26 | Hordeum vulgare var. distichum | 1761172 | nd | 253499 | 344182 | 504095 | 659396 | nd | nd | nd | nd |
| CHL26 | Hordeum vulgare var. distichum | 544302 | nd | 57773 | 32433 | 211504 | 242592 | nd | nd | nd | nd |
| CHL27 | Phoenix dactylifera | 214854 | 2005118 | 93188 | nd | 54401 | 67265 | 166394 | 433895 | 561882 | 842947 |
| CHL27 | Phoenix dactylifera | 220930 | 2053900 | nd | nd | 117899 | 103031 | 193799 | 482559 | 555211 | 822331 |
| CHL28 | Wollemia nobilis | 136252 | 2098604 | nd | nd | 66640 | 69612 | 210029 | 501060 | 570068 | 817447 |
| CHL28 | Wollemia nobilis | 215865 | 1472498 | 67207 | 30122 | 51007 | 67529 | 167707 | nd | 529508 | 775283 |
| CHL29 | Cucumis sativus | 85466 | 2094838 | nd | nd | 47622 | 37844 | 197285 | 460480 | 572147 | 864926 |
| CHL29 | Cucumis sativus | 199316 | 1907160 | nd | 65112 | 59336 | 74868 | 219990 | 437255 | 425412 | 824503 |
| CHL30 | Tarenaya hassleriana | 407190 | 1651782 | 132167 | nd | 195116 | 79907 | 84617 | 459806 | 275750 | 831609 |
| CHL30 | Tarenaya hassleriana | 775787 | 1162942 | 147217 | 78822 | 370197 | 179551 | nd | 434141 | nd | 728801 |
| CHL31 | Solanum tuberosum | nd | 1946947 | nd | nd | nd | nd | 194042 | 519194 | 461284 | 772427 |
| CHL31 | Solanum tuberosum | 196969 | 2073336 | nd | nd | 88954 | 108015 | 218340 | 449385 | 587097 | 818514 |
| CHL32 | Populus trichocarpa | 125192 | 2010526 | nd | nd | 47822 | 77370 | 186712 | 469136 | 568785 | 785893 |
| CHL32 | Populus trichocarpa | 234302 | 1809325 | 67097 | 41140 | 60729 | 65336 | 145991 | 424868 | 500780 | 737686 |
| CHL33 | Vigna radiata | 206045 | 1981426 | nd | nd | 90029 | 116016 | 199490 | 443865 | 546929 | 791142 |

FIG. 2

| CHL33 | Vigna radiata | 193761 | 2108416 | nd | nd | 87575 | 106186 | 217705 | 482949 | 580089 | 827673 |
|---|---|---|---|---|---|---|---|---|---|---|---|
| N1 | Negative control GFP | nd | 1974089 | nd | nd | nd | nd | 207234 | 469358 | 543483 | 754014 |
| N1 | Negative control GFP | nd | 2083472 | nd | nd | nd | nd | 248846 | 423746 | 596598 | 814282 |
| P2 | Postive control Chlamydomon as reinhardtii | 699847 | nd | nd | nd | 284290 | 415557 | nd | nd | nd | nd |
| P2 | Postive control Chlamydomon as reinhardtii | 738791 | nd | nd | nd | 313132 | 425659 | nd | nd | nd | nd |

| Poly-peptide | Organism of origin | sum phorbides | sum phytines | Pheophorbide B | Pyro-pheophorbide B | Pheophorbide A | Pyro-pheophorbide A | Pheophytin B | Pyro pheophytin B | Pheophytin A | Pyro pheophytin A |
|---|---|---|---|---|---|---|---|---|---|---|---|
| CHL25 | Gossypium raimondii | 682832 | 1665483 | 203729 | 123544 | 200295 | 155264 | 154662 | 415114 | 424929 | 670778 |
| CHL25 | Gossypium raimondii | 433068 | 1639813 | 141560 | 57416 | 135845 | 98247 | 126519 | 393480 | 419178 | 700636 |
| CHL26 | Hordeum vulgare var. distichum | 1961984 | nd | 288065 | 428220 | 515318 | 730381 | nd | nd | nd | nd |
| CHL26 | Hordeum vulgare var. distichum | 1235980 | nd | 198696 | 271455 | 332811 | 433018 | nd | nd | nd | nd |
| CHL27 | Phoenix dactylifera | 206094 | 1798845 | nd | nd | 102826 | 103268 | 174535 | 405629 | 485365 | 733316 |
| CHL27 | Phoenix dactylifera | 280806 | 1733146 | 82107 | 32874 | 89643 | 76182 | 149358 | 439387 | 439352 | 705049 |
| CHL28 | Wollemia nobilis | 158680 | 2075438 | nd | nd | 69972 | 88708 | 238509 | 535100 | 531720 | 770109 |
| CHL28 | Wollemia nobilis | 191785 | 1914612 | nd | nd | 84514 | 107271 | 199692 | 485069 | 509453 | 720398 |
| CHL29 | Cucumis sativus | 395615 | 1979120 | 98132 | 52976 | 114957 | 129550 | 236918 | 464484 | 506263 | 771455 |
| CHL29 | Cucumis sativus | 124703 | 2016619 | nd | nd | 62823 | 61880 | 200440 | 520274 | 520436 | 775469 |
| CHL30 | Tarenaya hassleriana | 482799 | 1548865 | 131662 | 106789 | 245739 | 105398 | 85863 | 455875 | 270230 | 736897 |
| CHL30 | Tarenaya_hassleriana | 994370 | 1182489 | 266503 | nd | 442271 | 178807 | nd | 397455 | 120012 | 665022 |
| CHL31 | Solanum tuberosum | 184629 | 1725831 | 40036 | 36792 | 42879 | 64922 | 146351 | 439657 | 456005 | 683818 |
| CHL31 | Solanum tuberosum | 151987 | 1755184 | nd | nd | 70020 | 81967 | 174556 | 427006 | 476779 | 676843 |
| CHL32 | Populus trichocarpa | 197752 | 1764263 | 43990 | 38111 | 37199 | 78452 | 157704 | 428592 | 469300 | 708667 |
| CHL32 | Populus trichocarpa | 393823 | 2227493 | 67553 | nd | 133308 | 192962 | 255280 | 552761 | 602588 | 816864 |
| CHL33 | Vigna radiata | 182783 | 1854267 | nd | nd | 76870 | 105913 | 189671 | 461626 | 484065 | 718905 |
| CHL33 | Vigna radiata | 206810 | 2013555 | nd | nd | 91980 | 114830 | 234141 | 494192 | 526247 | 758975 |
| N1 | Negative control GFP | 146294 | 1831921 | nd | nd | 74351 | 71943 | 191888 | 404939 | 504627 | 730467 |
| N1 | Negative control GFP | 299942 | 1757280 | 79849 | 40073 | 93101 | 86919 | 172642 | 420907 | 468692 | 695039 |
| P2 | Postive control Chlamydomonas reinhardtii | 1141781 | nd | 132388 | 225164 | 302417 | 481812 | nd | nd | nd | nd |
| P2 | Postive control Chlamydomonas reinhardtii | 1175042 | nd | 138320 | 240386 | 314910 | 481426 | nd | nd | nd | nd |

FIG. 4A

| | a | | | | b | | | | |
|---|---|---|---|---|---|---|---|---|---|
| | CHYL | PYN | PPYN | POB | PPOB | CHYL | PYN | PPYN | POB | PPOB | Total |
| | ppm | | | | | ppm | | | | | ppm |
| Crude Canola | b.d. | 1.00 | 8.90 | b.d. | 0.50 | b.d. | 0.12 | 4.70 | b.d. | 0.18 | 15.40 |
| EDLC94 | b.d. | b.d. | 0.14 | 0.38 | 4.89 | b.d. | b.d. | 0.07 | 0.20 | 2.71 | 8.39 |
| CHL026 | b.d. | b.d. | 0.81 | 0.48 | 4.58 | b.d. | b.d. | 0.45 | 0.22 | 2.61 | 9.15 |

CHL=Chlorophyll; PYN= Pheophytin; PPYN= Pyropheophytin; POB= Pheophorbide; PPOB= Pyropheophorbide
b.d. = below detection

FIG. 4B

| | PC | PE | PI | PA | lyso-PC | lyso-PE | lyso-PI | lyso-PA | C | E | I | A |
|---|---|---|---|---|---|---|---|---|---|---|---|---|
| | (%) | (%) | (%) | (%) | (%) | (%) | (%) | (%) | (%) | (%) | (%) | (%) |
| EDLC94 | 0.81 | 0.22 | 0.54 | 0.31 | 4.37 | 1.29 | 2.17 | 1.09 | 0.08 | b.d. | b.d. | 0.11 |
| CHL026 | 0.39 | 0.22 | 0.18 | 0.11 | 3.14 | 0.85 | 1.69 | 0.93 | 0.08 | 0.04 | b.d. | 0.14 |

PC = Phosphatidyl Choline; PE = Phosphatidyl Ethanolamine; PI = Phosphatidyl Inositol; PA = Phosphatidic Acid
C = phosphocholine, E = phosphoethanolamine; I = phosphoinositol; A = phosphate
b.d. = below detection

| | a | | | | | b | | | | | Total |
|---|---|---|---|---|---|---|---|---|---|---|---|
| | CHYL | PYN | PPYN | POB | PPOB | CHYL | PYN | PPYN | POB | PPOB | |
| | | ppm | | | | | ppm | | | | ppm |
| Crude Canola Oil Start Material | b.d. | 0.90 | 8.20 | b.d. | 0.63 | b.d. | 0.13 | 3.90 | b.d. | 0.27 | 14.03 |
| Rxn 3 - CHL26 | b.d. | 0.15 | 2.60 | 0.69 | 4.65 | b.d. | 0.04 | 1.40 | 0.23 | 2.40 | 12.16 |
| Rxn 4 - ELDC94 | b.d. | 0.23 | 6.70 | 0.60 | 1.30 | b.d. | 0.05 | 3.30 | 0.12 | 0.60 | 12.90 |
| Rxn 5 - CHL26 | b.d. | 0.29 | 4.30 | 0.48 | 3.40 | b.d. | 0.06 | 2.20 | 0.11 | 1.70 | 12.54 |
| Rxn 6 - CHL26 | b.d. | 0.26 | 3.80 | 0.64 | 3.70 | b.d. | 0.05 | 1.90 | 0.17 | 1.90 | 12.42 |
| Rxn 7 - CHL26 | b.d. | b.d. | 0.82 | 0.79 | 5.90 | b.d. | b.d. | 0.44 | 0.13 | 3.20 | 11.28 |
| Crude Soybean Oil | 0.1 | 0.10 | 0.11 | b.d. | b.d. | b.d. | b.d. | b.d. | b.d. | b.d. | 0.31 |
| Rxn 8 - CHL26 | b.d. | 0.11 | 0.12 | b.d. | b.d. | b.d. | 0.05 | 0.05 | b.d. | b.d. | 0.28 |

CHYL=Chlorophyll; PYN= Pheophytin; PPYN= Pyropheophytin; POB= Pheophorbide; PPOB= Pyropheophorbide
b.d.=below detection

FIG. 5A

| | PC (%) | PE (%) | PI (%) | PA (%) | lyso-PC (%) | lyso-PE (%) | lyso-PI (%) | lyso-PA (%) | C (%) | E (%) | I (%) | A (%) |
|---|---|---|---|---|---|---|---|---|---|---|---|---|
| Rxn 3 - CHL26 Gums | b.d. | b.d. | b.d. | b.d. | 0.12 | 0.4 | 0.92 | 1.11 | 0.14 | b.d. | b.d. | b.d. |
| Rxn 4 - ELDC94 Gums | b.d. | b.d. | b.d. | b.d. | 0.35 | 0.6 | 1.12 | 1.14 | 0.13 | b.d. | b.d. | b.d. |
| Rxn 5 - CHL26 Gums | b.d. | b.d. | b.d. | 0.11 | 0.13 | 0.6 | 1.19 | 1.29 | 0.17 | b.d. | b.d. | b.d. |
| Rxn 6 - CHL26 Gums | b.d. | b.d. | b.d. | b.d. | b.d. | 0.6 | 1.06 | 1.08 | 0.13 | b.d. | b.d. | b.d. |
| Rxn 7 - CHL26 Gums | 0.44 | 0.57 | 0.42 | 0.41 | 3.81 | 3.11 | 0.87 | 0.94 | 0.05 | b.d. | b.d. | b.d. |
| Rxn 8 - CHL26 SBO Gums | b.d. | b.d. | b.d. | b.d. | 0.11 | 0.2 | 0.21 | 0.17 | 0.09 | 0.11 | 0.23 | 0.27 |

PC = Phosphatidyl Choline; PE = Phosphatidyl Ethanolamine; PI = Phosphatidyl Inositol; PA = Phosphatidic Acid
C = phosphocholine; E = phosphoethanolamine; I = phosphoinositol; A = phosphate
b.d. = below detection

FIG. 5B

|  | a | | | | | b | | | | | Total |
|---|---|---|---|---|---|---|---|---|---|---|---|
|  | CHYL | PYN | PPYN | POB | PPOB | CHYL | PYN | PPYN | POB | PPOB |  |
|  | ppm | | | | | ppm | | | | | ppm |
| Rxn 3 - CHL26 Gums | b.d. | b.d. | 0.06 | 0.59 | 4.30 | b.d. | b.d. | b.d. | b.d. | 1.50 | 6.45 |
| Rxn 4 - ELDC94 Gums | b.d. | b.d. | 0.11 | 0.50 | 2.00 | b.d. | b.d. | 0.07 | b.d. | 0.56 | 3.24 |
| Rxn 5 - CHL26 Gums | b.d. | b.d. | 0.16 | 0.20 | 1.80 | b.d. | b.d. | 0.14 | b.d. | 0.68 | 2.98 |
| Rxn 6 - CHL26 Gums | b.d. | b.d. | 0.13 | 0.14 | 1.30 | b.d. | b.d. | 0.06 | b.d. | 0.55 | 2.18 |
| Rxn 7 - CHL26 Gums | b.d. | b.d. | b.d. | 0.22 | 3.30 | b.d. | b.d. | b.d. | b.d. | 1.50 | 5.02 |
| Rxn 8 - CHL26 SBO Gums | b.d. | b.d. | b.d. | 0.44 | 0.12 | b.d. | b.d. | b.d. | b.d. | b.d. | 0.56 |

CHYL=Chlorophyll; PYN= Pheophytin; PPYN= Pyropheophytin; POB= Pheophorbide; PPOB= Pyropheophorbide
b.d. = below detection;
SBO=Soybean oil

FIG. 5C

| | a (ppm) | | | | | a' (ppm) | | b (ppm) | | | | | b' (ppm) | | | Total ppm |
|---|---|---|---|---|---|---|---|---|---|---|---|---|---|---|---|---|
| | CHYL | PYN | PPYN | POB | PPOB | PYN | POB | CHYL | PYN | PPYN | POB | PPOB | CHYL | PYN | POB | |
| ORCAN | 0.08 | 9.29 | 6.69 | b.d. | b.d. | 4.80 | b.d. | 0.17 | 2.23 | 2.83 | b.d. | b.d. | 0.11 | 1.20 | b.d. | 27.38 |
| Rxn 9 - ELDC94 | 0.17 | 1.96 | 3.01 | 2.65 | 1.06 | 1.50 | 0.30 | 0.12 | 0.66 | 0.81 | 0.07 | 0.20 | b.d. | 0.30 | 0.05 | 12.86 |
| Rxn 10 - ELDC94 | 0.08 | 4.77 | 6.22 | 0.22 | 0.14 | 3.19 | 0.06 | 0.11 | 1.28 | 2.82 | b.d. | b.d. | b.d. | 0.9 | b.d. | 19.79 |
| Combined 9 & 10 | 0.19 | 5.97 | 6.85 | 0.18 | 0.15 | 1.85 | 0.05 | 0.12 | 1.64 | 1.58 | b.d. | b.d. | b.d. | 0.50 | b.d. | 19.10 |
| Rxn 11 - CHL26 | 0.09 | 1.96 | 3.01 | 2.96 | 1.17 | 3.38 | 0.32 | 0.12 | 0.73 | 1.69 | 0.16 | 0.34 | b.d. | 0.62 | b.d. | 16.56 |
| Rxn 12 - CHL26 | n.m. | n.m. | n.m. | n.m. | n.m. | n.m. | n.m. | n.m. | n.m. | n.m. | n.m. | n.m. | n.m. | n.m. | n.m. | n.m. |
| Combined 11 & 12 | 0.10 | 2.22 | 3.18 | 3.03 | 1.29 | 3.16 | 0.28 | 0.12 | 0.73 | 1.73 | 0.86 | 0.64 | 0.12 | 0.64 | 0.08 | 18.19 |
| ORSBO | 0.21 | 0.70 | 0.24 | b.d. | ND | 1.26 | b.d. | 0.28 | 0.24 | 0.49 | b.d. | b.d. | b.d. | 0.43 | b.d. | 3.85 |
| Rxn 13 - ELDC94 | 0.17 | 0.31 | 0.05 | 0.03 | 0.03 | b.d. | b.d. | 0.22 | 0.11 | 0.23 | b.d. | b.d. | b.d. | b.d. | b.d. | 1.15 |
| ORSBO | 0.22 | 0.72 | 0.25 | b.d. | b.d. | 1.27 | b.d. | 0.26 | 0.24 | 0.52 | b.d. | b.d. | b.d. | 0.43 | b.d. | 3.90 |
| Rxn 14 - | 0.17 | 0.31 | 0.08 | 0.05 | 0.05 | b.d. | 0.03 | 0.22 | 0.11 | 0.23 | 0.03 | 0.05 | 0.11 | ND | b.d. | 1.41 |

FIG. 6

|  | a | | | | a' | | | b | | | | b' | | | Total |
| --- | --- | --- | --- | --- | --- | --- | --- | --- | --- | --- | --- | --- | --- | --- | --- |
|  | CHYL | PYN | PPYN | POB | PPOB | PYN | POB | CHYL | PYN | PPYN | POB | PPOB | CHYL | PYN | POB |  |
|  | ppm | | | | | ppm | | ppm | | | | | ppm | | | ppm |
| CHL26 | | | | | | | | | | | | | | | | |
| Ref. SBO | 0.20 | 0.71 | 0.26 | b.d. | b.d. | 1.27 | b.d. | 0.27 | 0.23 | 0.52 | b.d. | b.d. | b.d. | 0.43 | b.d. | 3.90 |
| Rxn 15 - ELDC94 | 0.17 | 0.33 | 0.13 | b.d. | b.d. | 0.62 | b.d. | 0.22 | 0.11 | 0.25 | b.d. | b.d. | b.d. | 0.21 | b.d. | 2.05 |
| Ref SBO | 0.21 | 0.36 | 0.12 | b.d. | b.d. | 0.63 | b.d. | 0.28 | 0.12 | 0.26 | b.d. | b.d. | b.d. | 0.21 | b.d. | 2.19 |
| Rxn 16 - CHL26 | 0.17 | 0.32 | 0.10 | 0.04 | 0.03 | 0.61 | b.d. | 0.22 | 0.11 | 0.24 | b.d. | b.d. | b.d. | b.d. | b.d. | 1.84 |

CHYL=Chlorophyll; PYN= Pheophytin; PPYN= Pyropheophytin; POB= Pheophorbide; PPOB= Pyroppheophorbide
b.d.= below detection; n.m. = not measured ORCAN=Once refined Canola oil; ORSBO= Once refined soybean oil; SBO=Soybean oil

FIG. 6A

SILICA ADSORBENT TREATMENT FOR REMOVAL OF CHLOROPHYLL DERIVATIVES FROM TRIACYLGLYCEROL-BASED OILS

CROSS-REFERENCE TO RELATED APPLICATIONS

This application claims priority benefit of U.S. Provisional Application Ser. No. 62/824,636 filed Mar. 27, 2019, the entire contents of which are incorporated by reference herein.

FIELD OF THE DISCLOSURE

The present disclosure relates to a process for treating an oil comprising chlorophyll derivatives. In particular, the present disclosure relates to an improved process for removing impurities, including chlorophyll derivatives and/or trace metals, from an oil, and to improved silica based adsorbents for use in the process.

SEQUENCE LISTING

The instant application contains a Sequence Listing which has been submitted electronically in ASCII format and is hereby incorporated by reference in its entirety. Said ASCII copy, created on Mar. 26, 2019, is named '35893-513_SEQ_LIST.txt' and is 36,864 bytes in size.

BACKGROUND OF THE DISCLOSURE

Crude triacylglycerol oils obtained from either pressing or solvent extraction methods are a complex mixture of triacylglycerols, phospholipids, sterols, tocopherols, diacylglycerols, free fatty acids, trace metals, chlorophylls, beta-carotene, and other minor compounds. It is desirable to remove the phospholipids, free fatty acids, trace metals, chlorophylls, and beta-carotene in order to produce a quality fully refined oil or a salad oil with a bland taste, light color, and a long shelf life.

The removal of phospholipids generates the largest amount of neutral oil losses associated with the refining of triacylglycerol oils. The removal of chlorophylls generates the second largest amount of neutral oil losses associated with the refining of triacylglycerol-based oils.

Several different techniques may be used for phospholipid removal, including water degumming, enzyme assisted water degumming, acid degumming, caustic refining, and enzymatic treatment.

Water degumming is usually applied to crude oils containing a high amount of hydratable phospholipids. Due to its mild characteristics, the phospholipids obtained can be used as lecithin (a natural emulsifier). The oil obtained from this technique is generally referred to in the industry as being "degummed," despite being only partially degummed. Since water degummed oil still contains high amounts of phospholipids, especially non-hydratable phospholipids, the use of other process techniques, such as caustic refining or phospholipase A (PLA) enzyme degumming, can be required to produce a finished, high quality oil having high stability and low color.

In the water degumming process, water is added to crude oil with mixing to aid the hydration of the phospholipids present in the oil. The hydration of the phospholipids or "gums" causes the gums to swell and agglomerate as a flocculent, which is subsequently separated from the remainder of the oil. The oil loss from water degumming processes may be significant, with a negative impact in the overall economic balance on the refined oil process cost.

Enzyme assisted water degumming is usually applied to crude oils containing a high amount of hydratable phospholipids, where the goal is to react all of the hydratable phospholipids and convert them into diacylglycerols increasing the oil yield, while maintaining the non-hydratable phospholipids in the oil. Enzymes utilized for this process are Phospholipase C (PLC) and Phosphatidyl Inositol Phospholipase (PI-PLC).

In the enzyme assisted water degumming process, water and PLCs are added to crude oil with mixing. The enzymes are then allowed to react with the phospholipids in the oil with shear mixing to aid in the conversion of phosphatidyl choline (PC), phosphatidyl ethanolamine (PE), and PI to diacylglycerols in the oil. The heavy phase (water, denature protein, and phosphor-compounds) has a specific gravity higher than that of the oil and may be separated by settling, filtration, or the industrial practice of centrifugation. The enzyme assisted water degumming process removes predominately only the hydratable phospholipids. The remaining phospholipids, measured as the salts of phosphatidic acid can be removed in subsequent processing operations.

Acid degumming is usually applied to crude oils when the goal is the total removal of phospholipids. The oil obtained is usually called "super-degummed" or "totally degummed" in the industry. Crude oil is treated with phosphoric acid or citric acid. The acid improves the hydrophilic nature of the non-hydratable phospholipids (NHPs), thus aiding in their removal. Water is then added to the acid-treated crude oil, and the oil is mixed to aid the hydration of the phospholipids. The hydration of the phospholipids or "gums" causes the gums to swell and agglomerate as a flocculent, which is subsequently removed. The acid degumming process removes most of the phospholipids, but enough still remain in the degummed oil to require additional processing. As in the water degumming process, some of the oil is emulsified, and is considered a process loss, with the negative economic impact on the overall economic balance of the refined oil process cost.

Caustic refining is usually applied to crude or water degummed oils when the goal is to remove all of the phospholipids and free fatty acids. Crude or water degummed oil is treated with phosphoric acid or citric acid. The acid improves the hydrophilic nature of the NHPs, thus aiding in their removal. A diluted sodium hydroxide solution is added to the acid-treated oil. The caustic solution neutralizes the free fatty acids (producing sodium soaps), neutralizes the excess acid, and with the sodium soaps created, assists in hydrating and emulsifying all the remaining phospholipids. The sodium hydroxide solution/oil is mixed and then separated by settling, filtration, or industrially by centrifugation. The caustic treated oil is then "washed" and centrifuged again. The oil from the centrifuge is known as "Once Refined" and the water is commonly known as "Wash Water". For food applications, the "once refined" oil is usually submitted for bleaching and deodorization to produce salad oil. An alternative to water washing is to treat the caustic treated oil with an adsorbent silica gel and filter out the residual soaps and phospholipids not removed in the initial centrifugation.

"Enzymatic refining" or "enzymatic degumming" is used when the goal is the total removal of phospholipids. Generally, enzymatic degumming treatments of the prior art have been practiced on oils that have been degummed previously by one of the other methods, typically water degumming. For food applications, the enzyme degummed oil is sequentially submitted to bleaching and deodorization, a process known in the industry as "physical refining." Enzymatic degumming provides a better oil yield than water, acid, or caustic degumming, with improved economic results.

The enzymatic reaction changes the nature of the phospholipid, cleaving some of the phospholipid parts. This reduces the phospholipids' emulsification properties, so that less oil is lost when the gums are separated from the oil, thus saving oil. Enzymes exhibiting activity with phospholipids are commonly called "phospholipases". The types of phospholipase are based on the position on the phospholipid molecule at which the enzyme reacts, and are known as PLA1, PLA2, PLC, and PLD. Different types of phospholipases will yield different compounds upon reacting with the phospholipids.

Commercial PLA1 enzymes with phospholipase activity are Lecitase® Ultra and QuaraLowP. Commercial PLA2 enzymes with phospholipase activity are Rohalase Xtra and LysoMax. These products are known to yield polar lysophospholipids and polar fatty acids when mixed with degummed oil with a 1-1.5% water citric acid-NaOH buffer at 4.5<pH<7.0 and 40° C.<T<55° C. The PLA1 selectively hydrolyzes the fatty acid opposite the phosphate functional group on the glycerol backbone and the PLA2 selectively hydrolyzes the fatty acid in the center of the glycerol backbone of the phospholipid. PLAs are non-selective for the phospholipids they react with.

The resulting reaction yields a lyso-phospholipid and a fatty acid. The lyso-phospholipid molecule has lost one hydrophilic functional group, and the remaining alcohol group at the reaction site is hydrophilic. Now with two hydrophilic sites, the lyso-phospholipid molecule is water soluble, and has lost its emulsification properties. The PLA1 or PLA2 degumming process thus reduces refining losses by no longer removing any neutral oil with the gums, and the only loss is the original phospholipid molecule.

It is known in the art that PLC enzymes react with a phospholipid by selectively hydrolyzing the phosphate functional group. The resulting reaction yields a diacylglycerol ("DAG") and a phosphatidic group. The diacylglycerol molecule no longer has the phosphate functional group and does not need to be removed. The PLC degumming process reduces the refining loss by retaining the original phospholipid molecule, while removing only the phosphate functional group. However, PLC does not react with all of the phospholipids present in the oil. Generally, PLC does not react with either phosphatidic acid (PA) or phosphatidyl inositol (PI). A PI-PLC used in combination with PLC enables the reaction and removal of PC, PE, and PI. Yet the non-hydratable phosphatides that remain in oil after water degumming. Thus, the enzymatic assisted water degumming treated oil must be further treated with caustic to remove the residual gums, or may further be treated with PLA1 or PLA2.

Triacylglycerol oils from oilseeds such as soybean and canola, and oil fruits, such as palm and algal source oils, contain chlorophyll. Chlorophyll is removed during many stages of the oil production process, including seed crushing, oil extraction, degumming, caustic treatment and bleaching steps. In the last of these, the bleaching process residual chlorophyll is removed to achieve acceptable levels. This chlorophyll is typically removed from the oil in a bleaching process step involving heating the oil and running it through an adsorbent to remove chlorophyll and other color-bearing compounds that impact the appearance and/or stability of the finished oil.

High level of chlorophyll pigments imparts undesirable color and induce oxidation of oil during storage leading to a deterioration of the oil. In the edible oil processing industry, a bleaching step is employed to lower chlorophyll levels to as low as 0.02 ppm to guarantee oil quality in terms of color and organolepticity. This bleaching step increases processing cost and reduces oil yield due to entrainment in the bleaching clay. The "spent" clay then must be disposed of environmentally and is a hazardous material to transport due to the spontaneous combustion nature acid treated material and adsorbed oil, approximately 30% wt.

Chlorophyll is modified during oil processing into a derivative known as pheophytin, by the loss of the magnesium ion from the porphyrin (chlorine) ring (see FIG. 1). Typically, pheophytin is more abundant in oil during processing than chlorophyll. Pheophytin can be further degraded into pyropheophytin (see Behavior of Chlorophyll Derivatives in Canola Oil Processing", JAOCS, Vol. no. 9 Sep. 1993, p. 837-841). Pyropheophytin is predominantly formed processing of vegetable oils (see e.g. 'The lipid handbook' ed. Frank D. Gunstone, John L. Harwood, Albert J. Dijkstra. 2007-3rd ed., p. 56). Chlorophyll, pheophytin and pyropheophytin occur in two forms the A and B form. The A component has a methyl group at the C7 position. The B component has an aldehyde at the C7 position.

The use of enzymes for the removal of pyropheophytin in vegetable oils is known from WO2010/143149 and WO2013/160372. WO2010/143149 discloses methods for treating pyropheophytin-containing compositions using enzymes capable of hydrolysing pyropheophytin derived for instance from *Triticum aestivum* and *Chlamydomonas reinhardtii*. WO2013/160372 discloses several chlorophyllase enzymes for instance from *Arabidopsis thaliana* and *Triticum aestivum*, which were able to convert pheophytin and pyropheophytin in oil.

Silicas have also been used as an adsorbent for removing impurities from triacylglycerol-based oils. Examples of silicas that have been used to purify oils include those described in U.S. Pat. Nos. 9,295,810; 4,781,864; and 9,493,748. Such silicas, however, are not fully effective at removing impurities from oils, and undesirable levels of impurities, including colorants such as chlorophyll derivatives, may remain in the oils even after silica treatment.

There is thus a need for alternative silicas that are capable of removing impurities from triacylglycerol-based oils.

SUMMARY OF THE DISCLOSURE

In one aspect, the present disclosure is directed to a process for treating an oil comprising a chlorophyll derivative, the process comprising contacting the oil with an adsorbent comprising a silica treated with an alkaline earth metal oxide, wherein the adsorbent has a pH of about 7 or greater, including from about 7 to about 10, comprises about 0.1 wt. % or greater of alkaline earth metal oxide, such as MgO, on a dry basis, and has a water content of about 3 wt. % or greater, and preferably, about 10 wt. % or greater, or from about 25 wt. % to about 75 wt. %.

In one particular aspect, the present disclosure is directed to a process for treating an oil comprising a chlorophyll derivative, the process comprising contacting the oil with an adsorbent comprising a silica treated with an alkaline earth metal oxide, wherein the adsorbent has a pH of from about 7 to about 10, and comprises from about 2.5 to about 15 wt.

%, or from about 5 to about 25 wt %, or from about 10 to about 20 wt % of MgO, on a dry basis, and has a water content of from about 25 to about 75 wt. %.

In another aspect, the present disclosure is directed to a process for treating an oil comprising a chlorophyll derivative, the process comprising: contacting the oil with a polypeptide having decolorase activity, or a composition comprising the polypeptide, to produce a decolorase-treated oil, and contacting the decolorase-treated oil with an adsorbent comprising a silica treated with an alkaline earth metal oxide, wherein the adsorbent has a pH of about 7 or greater, e.g., from about 7 to about 10, comprises about 0.1 wt. % or greater of alkaline earth metal oxide, such as MgO, on a dry basis, and has a water content of about 3 wt. % or greater, preferably, about 10 wt. % or greater, or from about 25 to about 75 wt. %.

In another aspect, the present disclosure is directed to a process for treating an oil comprising a chlorophyll derivative, the process comprising: contacting the oil with a polypeptide having decolorase activity, or a composition comprising the polypeptide, to produce a decolorase-treated oil, and contacting the decolorase-treated oil with an adsorbent comprising a silica treated with an alkaline earth metal oxide; wherein the adsorbent has a pH of from about 7 to about 10, and comprises from about 2.5 to about 15 wt. %, or from about 5 to about 25 wt %, or from about 10 to about 20 wt % of MgO, on a dry basis, and has a water content of from about 25 to about 75 wt. %.

In another aspect, the present disclosure is directed to a process for treating an oil comprising pyropheophytin, the process comprising: contacting the oil with a polypeptide having pyropheophytinase activity, or a composition comprising the polypeptide, wherein pyropheophytin is converted into pyropheophorbide, and optionally wherein pheophytin is converted into pheophorbide to produce a pyropheophytinase-treated oil, and contacting the pyropheophytinase-treated oil with an adsorbent comprising a silica treated with an alkaline earth metal oxide, wherein the adsorbent has a pH of about 7 or greater, e.g. from about 7 to about 10, comprises about 0.1 wt. % or greater of alkaline earth metal oxide, such as MgO, on a dry basis, and has a water content of about 3 wt. % or greater, preferably, about 10 wt. % or greater, or from about 25 to about 75 wt. %.

In another aspect, the present disclosure is directed to a process for treating an oil comprising pyropheophytin, the process comprising: contacting the oil with a polypeptide having pyropheophytinase activity, or a composition comprising the polypeptide, wherein pyropheophytin is converted into pyropheophorbide, and optionally wherein pheophytin is converted into pheophorbide to produce a pyropheophytinase-treated oil, and contacting the pyropheophytinase-treated oil with an adsorbent comprising a silica treated with an alkaline earth metal oxide; wherein the adsorbent has a pH of from about 7 to about 10, and comprises from about 2.5 to about 15 wt. %, or from about 5 to about 25 wt %, or from about 10 to about 20 wt % of MgO, on a dry basis, and has a water content of from about 25 to about 75 wt. %.

In another aspect, the present disclosure is directed to a process for treating an oil comprising a chlorophyll derivative, the process comprising: contacting the oil with a polypeptide having decolorase activity, or a composition comprising the polypeptide, to produce a decolorase-treated oil, and contacting the decolorase-treated oil with an adsorbent comprising a silica treated with an alkaline earth metal oxide, wherein the adsorbent has a pH of about 7 or greater, e.g. from about 7 to about 10, comprises about 0.1 wt. % or greater of alkaline earth metal oxide, such as MgO, on a dry basis, and has a water content of about 3 wt. % or greater, preferably, about 10 wt. % or greater, such as from about 25 to about 75 wt. %; and wherein the treatment reduces the total concentration of chlorophyll derivatives in the composition by at least 5% by weight, compared to the total concentration of chlorophyll derivatives in the composition prior to contact with the adsorbent.

In another aspect, the present disclosure is directed to a process for treating an oil comprising a chlorophyll derivative, the process comprising: contacting the oil with a polypeptide having decolorase activity, or a composition comprising the polypeptide, to produce a decolorase-treated oil, and contacting the decolorase-treated oil with an adsorbent comprising a silica treated with an alkaline earth metal oxide; wherein the adsorbent has a pH of from about 7 to about 10, and comprises from about 2.5 to about 15 wt. %, or from about 5 to about 25 wt %, or from about 10 to about 20 wt % of MgO, on a dry basis, and has a water content of from about 25 to about 75 wt. %; and wherein the treatment reduces the total concentration of chlorophyll derivatives in the composition by at least 5% by weight, compared to the total concentration of chlorophyll derivatives in the composition prior to contact with the adsorbent.

In another aspect, the polypeptide used in a process of the present disclosure is a polypeptide having pyropheophytinase activity, wherein the polypeptide is selected from the group consisting of:
  a. an isolated polypeptide which has at least 80%, 85%, 86%, 87%, 88%, 89%, 90%, 91%, 92%, 93%, 94%, 95%, 96%, 97%, 98% or at least 99%, or 100% identity to amino acids 1 to 318 of SEQ ID NO: 1; and,
  b. a polypeptide encoded by a nucleic acid sequence that has at least 80%, 85%, 86%, 87%, 88%, 89%, 90%, 91%, 92%, 93%, 94%, 95%, 96%, 97%, 98% or at least 99%, or 100% identity to the nucleic acid sequence of SEQ ID NO: 2.

In one embodiment, the polypeptide used in a process of the present disclosure converts a chlorophyll substrate into a chlorophyll product. A chlorophyll substrate may be selected from the group consisting of chlorophyll, pheophytin, pyropheophytin, and combinations thereof, and the chlorophyll product may be selected from the group consisting of chlorophyllide, pheophorbide, pyropheophorbide, and combinations thereof.

In one aspect, the oil comprises pyropheophytin, the polypeptide has pyropheophytinase activity as disclosed herein, and the pyropheophytin is converted into pyropheophorbide.

In another aspect, the present disclosure is directed to an oil produced by a process disclosed herein.

In another aspect, the present disclosure is directed to improved silica based adsorbents for use in the processes of the disclosure. The adsorbents comprise an amorphous porous silica treated with an alkaline earth metal oxide, preferably magnesium oxide, in an amount sufficient to provide a pH of about 7 or greater and a water content of about 3 wt. % or greater in the final adsorbent.

BRIEF DESCRIPTION OF THE DRAWINGS

FIGS. 2-2A: HPLC results of incubation pheophytin a and b and pyropheophytin a and b with different putative chlorophyllases at pH 7 and 50° C., for 24 hours. The amounts of the substrates pheophytin a and b and pyropheophytin a and b and the reaction products pheophorbide a and b and pyropheophorbide a and b are given as peak surface areas. The first two columns show the sum of reaction products and substrates. "nd" means: not detectable.

FIG. 3: HPLC results of incubation pheophytin a and b and pyropheophytin a and b with different putative chlorophyllases at pH 5 and 50° C., for 24 hours. The amounts of the substrates pheophytin a and b and pyropheophytin a and b and the reaction products pheophorbide a and b and pyropheophorbide a and b are given as peak surface areas. The first two columns show the sum of reaction products and substrates. "nd" means: not detectable.

FIGS. 4A and 4B: 4A: Chlorophyll derivatives 4B: Phosphor compounds in canola oil after 24 h incubation with CHL26 enzyme from *Hordeum vulgare* or the reference enzyme ELDC94 from *Chlamydomonas reinhardtii*.

FIGS. 5A-5C: 5A: Chlorophyll derivatives, and 5B: Phosphor compounds in canola oil and soy bean after several incubations with CHL26 enzyme from *Hordeum vulgare* and/or the reference enzyme ELDC94 from *Chlamydomonas reinhardtii*, under different reaction conditions and 5C: chlorophyll derivatives in the obtained gums.

FIGS. 6-6A: Chlorophyll derivatives in canola oil and soybean oil after caustic refining and after incubation with CHL26 enzyme from *Hordeum vulgare* or the reference enzyme ELDC94 from *Chlamydomonas reinhardtii*.

DEFINITIONS

Figure 1:
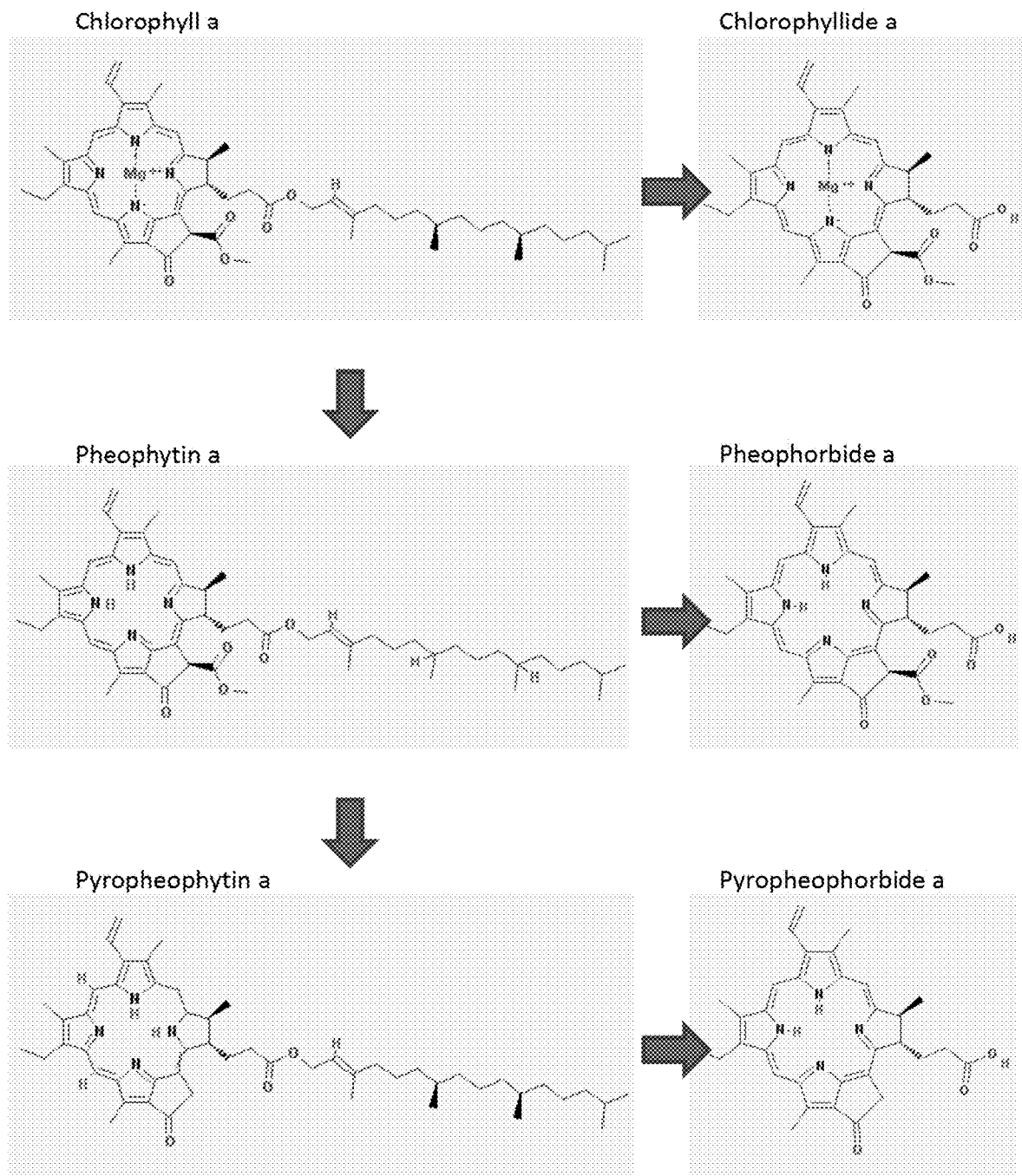
FIG. 1: Overview of the conversion of chlorophyll into pheophytin and pyropheophytin and into the respective reaction products chlorophyllide, pheophorbide and pyropheophorbide. The A compounds are shown, which have a methyl group at the C7 position. B compounds have an aldehyde in the C7 group instead of a methyl group. Structures are taken from PubChem, NCBI.
Figure 7:
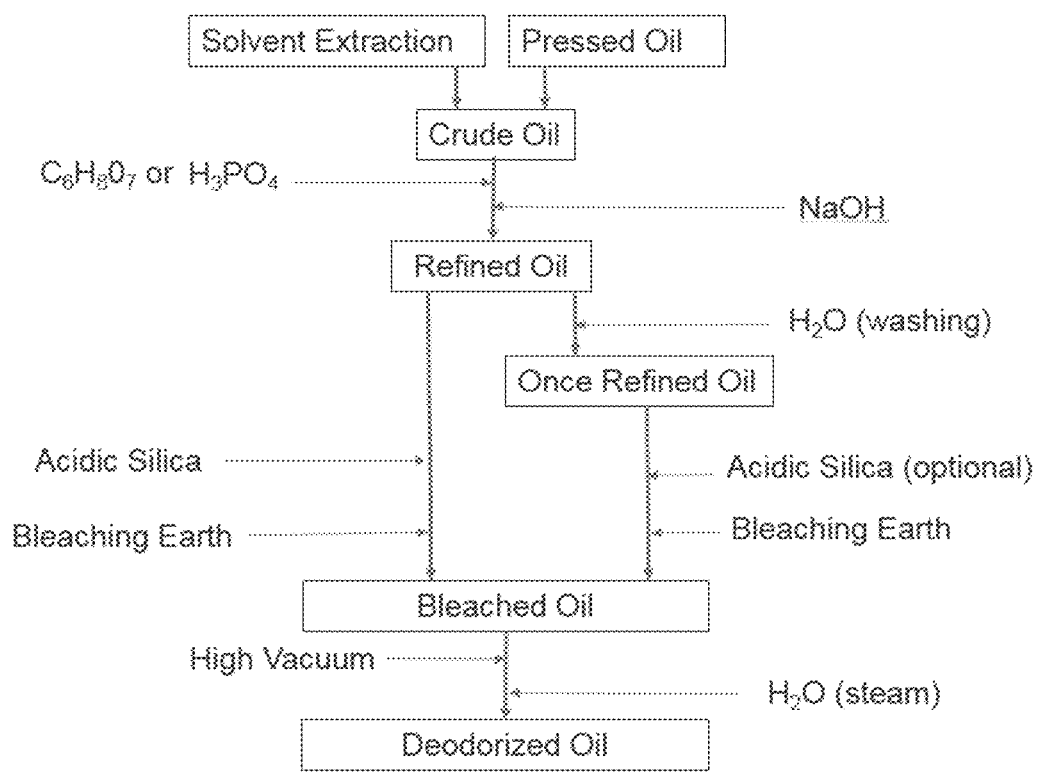
FIG. 7: Schematic presentation of a typical chemical refinery process for triacylglycerol based oils. A process of solvent extraction and/or pressing on an oilseed (rapeseed or soybean), oil fruit plant (palm), or single cell source (algal) to obtain a crude oil. The crude oil this then treated with citric or phosphoric acid to react with the non-hydratable phospholipids and then the addition of sodium hydroxide to neutralize the free fatty acids and form sodium soaps. The sodium soaps form an emulsion with the water present allowing the removal of non-hydratable phospholipids when the oil is centrifuged to produce refined oil. The refined oil may then be washed with hot water and centrifuged to remove the remaining soaps and phospholipids. Alternatively, the refined oil may be treated with acidic silica to adsorb soaps, trace metals and phospholipids. The industrial acidic silicas do not have any capacity to remove chlorophyll or chlorophyll derivatives. The oil is then treated with bleaching earth to remove the soaps, phospholipids, and chlorophyll and chlorophyll derivatives present in the oil. The final step in the deodorization step of steam distillation at elevated temperatures and vacuums of less than 5 mBar. The distillation primarily removes peroxides, aldehydes, ketones and other flavor compounds. It also destroys beta-carotene and removes the remaining free fatty acids (0.1 percent) to reach a level of 0.02 to 0.05% final Free Fatty Acid (FFA).
Figure 8:
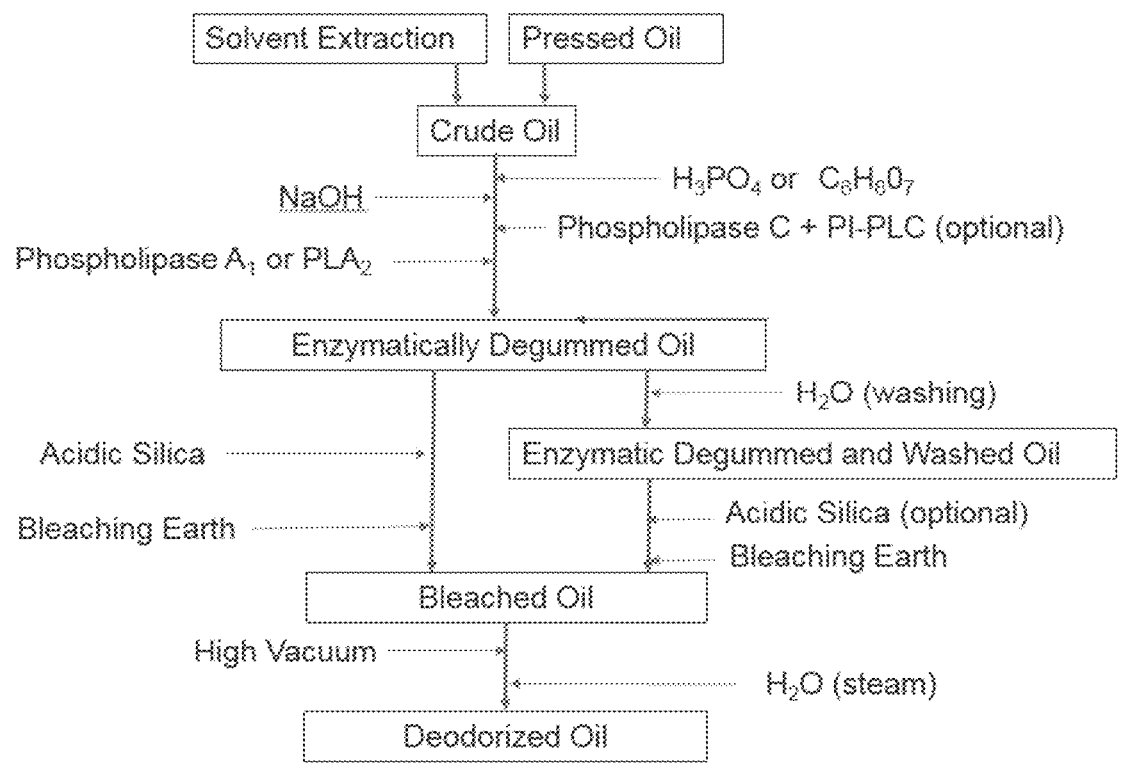
FIG. 8: Schematic presentation of a typical enzymatic degumming/physical refining process. The crude oil is treated with phosphoric or citric acid to enable the non-hydratable phospholipids to lose the calcium or magnesium bond to them at a pH of roughly 2. The sodium hydroxide is then added to bring the pH above 4 for citric acid or above 6 for phosphoric acid in order that the phospholipase may work and obtain a very low residual phosphorus <5 ppm) after the enzymatic reaction with the PLAs. Alternatively, the PLAs may be reacted with the PLC and/or PI-PLC to maximize the oil yield and still obtain a very low residual phosphorus allowing for physical refining. The oil is then either washed or treated with an acidic silica followed or in combination with bleaching earth. After the bleaching process with chlorophyll levels of less than 50 ppb, the oil is physically refined in the deodorizer. The high temperature steam distillation removes all of the compounds describe above in FIG. 7, but its primary purpose is the removal of FFA. The FFAs are distilled and collected in the scrubber. Very limited neutral oil is lost in the deodorization process compared to the losses associated from the emulsions formed in water degumming or chemical refining.
Figure 9:
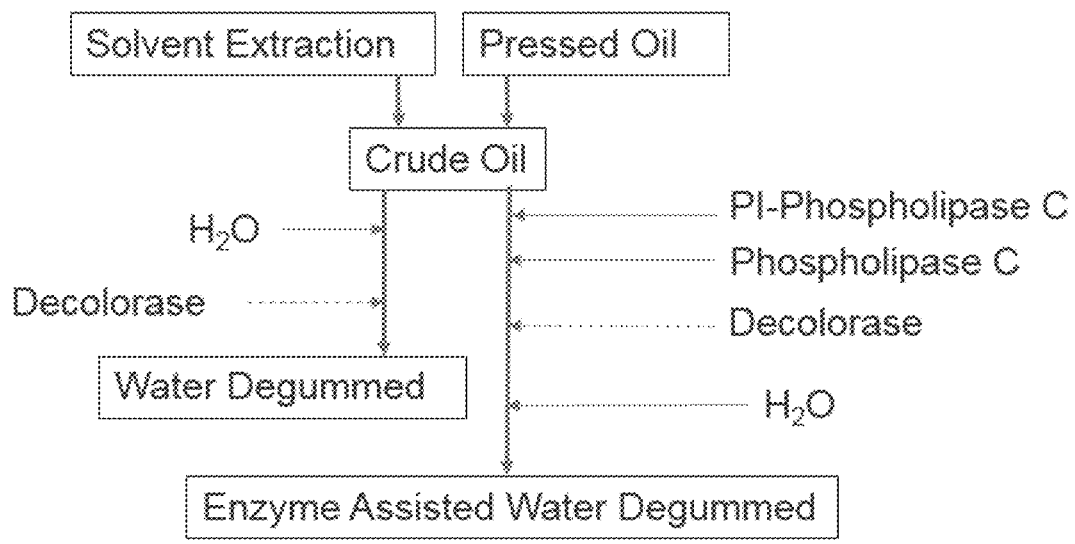
FIG. 9: Schematic presentation of the use of a decolorase enzyme in the water degumming process or the enzyme assisted water degumming process. A decolorase enzyme may be added with the water at 60° C., or with the PLC, or with the combination of PLC and PI-PLC. After two hours of incubation, the oil is heated to 70 to 85° C. and centrifuged to remove the reacted gums and reacted chlorophyll derivatives.
Figure 10:
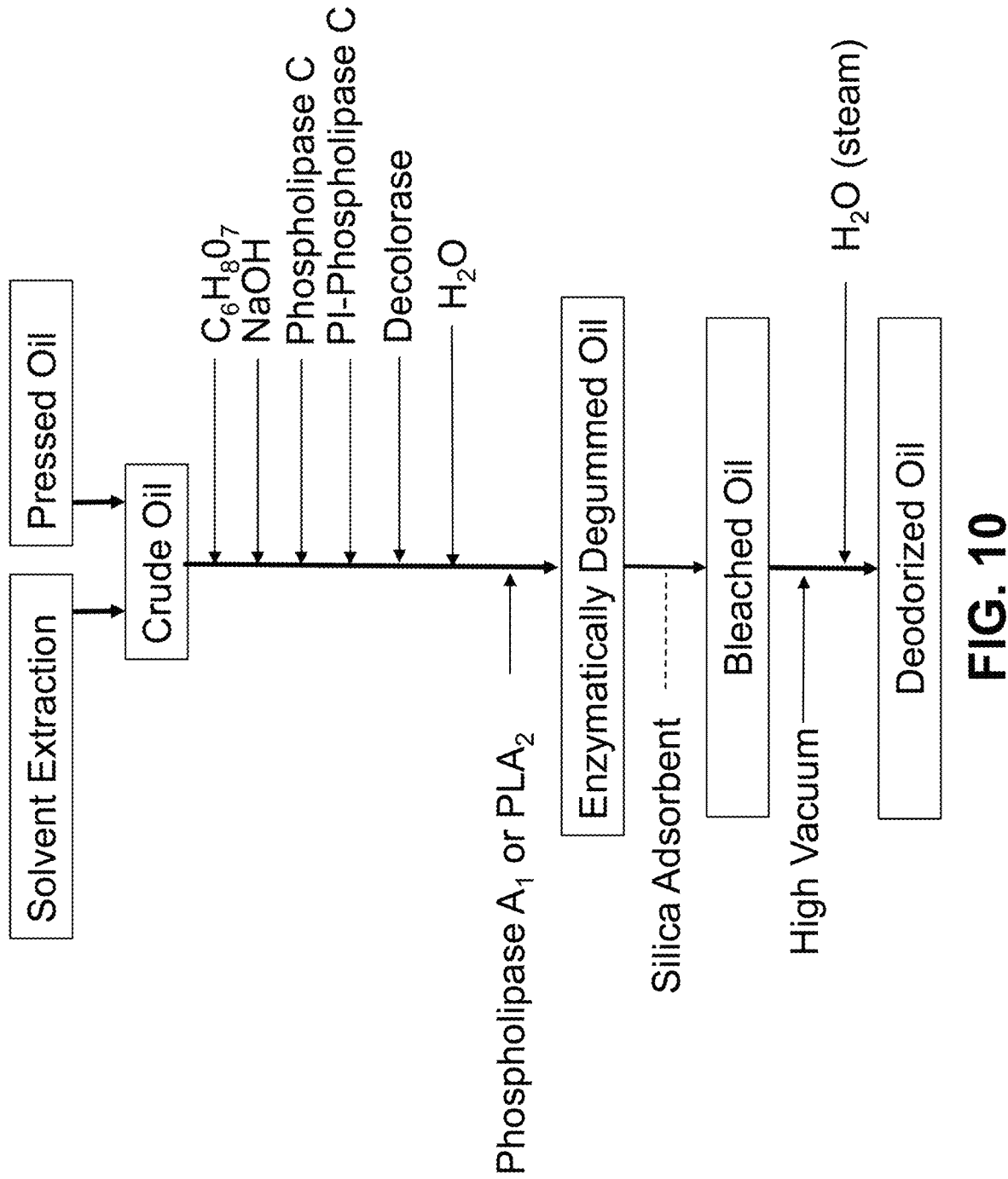
FIG. 10: Schematic presentation of an enzymatic degumming process modified to include treatment with a decolorase enzyme and a silica adsorbent (such as a MgO-treated adsorbent) of the present disclosure. The crude oil is first treated with citric acid to a pH of roughly 2 to dissociate the bond calcium and magnesium ions, the pH is raised above 4 to enable the PLCs and Decolorase enzymes in a pH that enable them to work efficiently. 1 to 5 percent water is added for the hydrolysis reactions. After the completion of the PLCs and Decolorase incubations, a PLA1 or PLA2 may be added to react with the non-hydratable phospholipids present in the oil. After an additional incubation of 2 to 6 hours, the oil is heated to 70 to 85° C. and centrifuged to remove the reacted gums and chlorophyll derivatives producing an oil with less than 5 ppm residual phosphorus in the oil. The enzymatically degummed oil may then be contacted with a silica adsorbent of the present disclosure, optionally under vacuum, to further remove chlorophyll derivatives and trace metals, as described herein.
Figure 11:
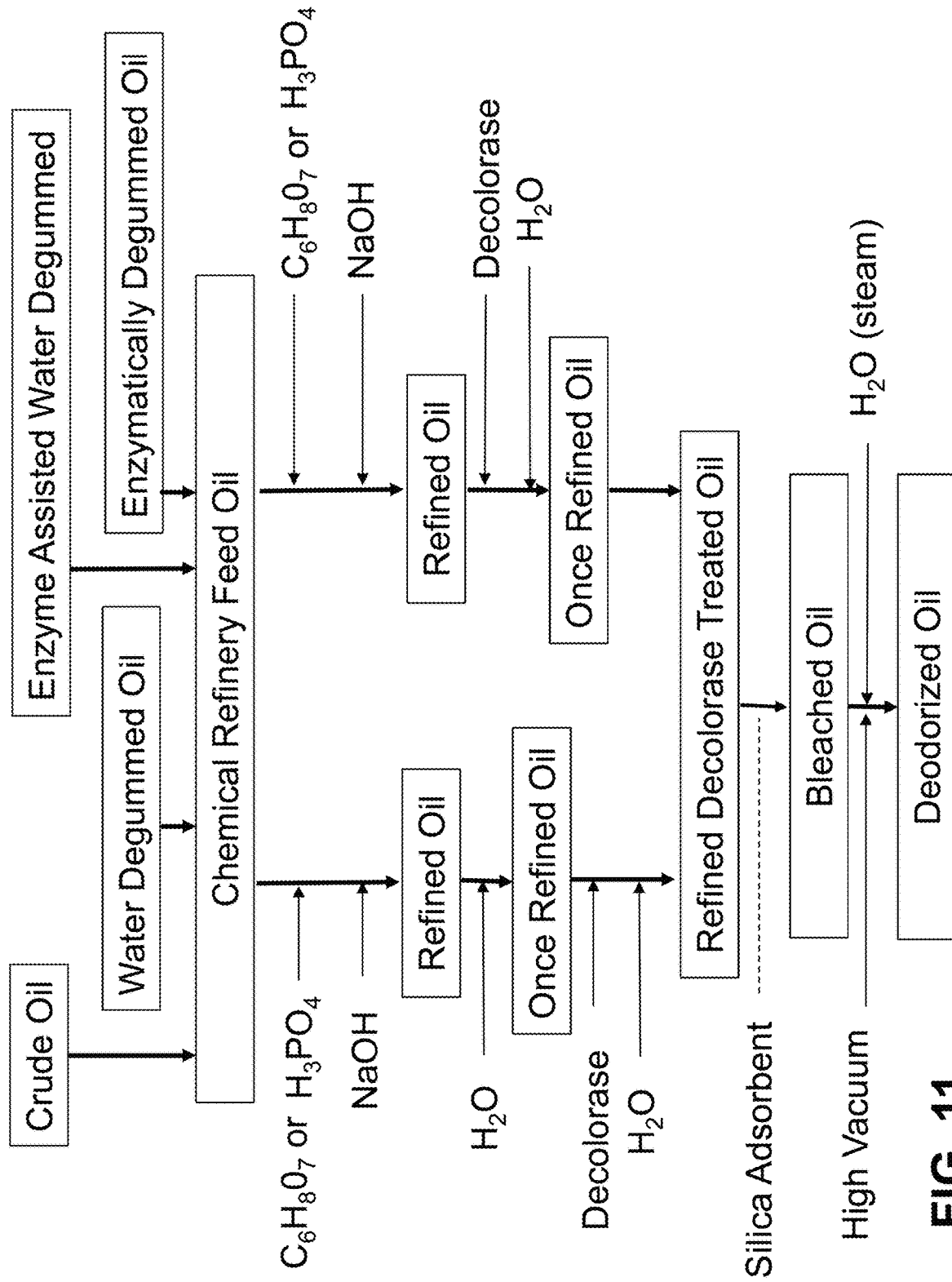
FIG. 11: Schematic presentation of a chemical refining process with a decolorase enzyme, followed by treatment with a silica adsorbent of the present disclosure. The decolorase enzyme may not be added in the acid or caustic addition steps due to the very low pH (roughly 2) and the very high pH (roughly 14) in the early steps of the process. The decolorase enzyme must be added after the initial centrifuge step in the refined oil. It is advantageous to add the decolorase enzyme with the washing step at a temperature suitable for the enzyme (50 to 65° C.). Allow an incubation time of at least two hours followed by heating to 70 to 85° C. prior to centrifugation. The oil would then be further processed by contacting with a silica adsorbent of the present disclosure, optionally under vacuum, to further remove chlorophyll derivatives and/or trace metals, as described herein.
Figure 12:
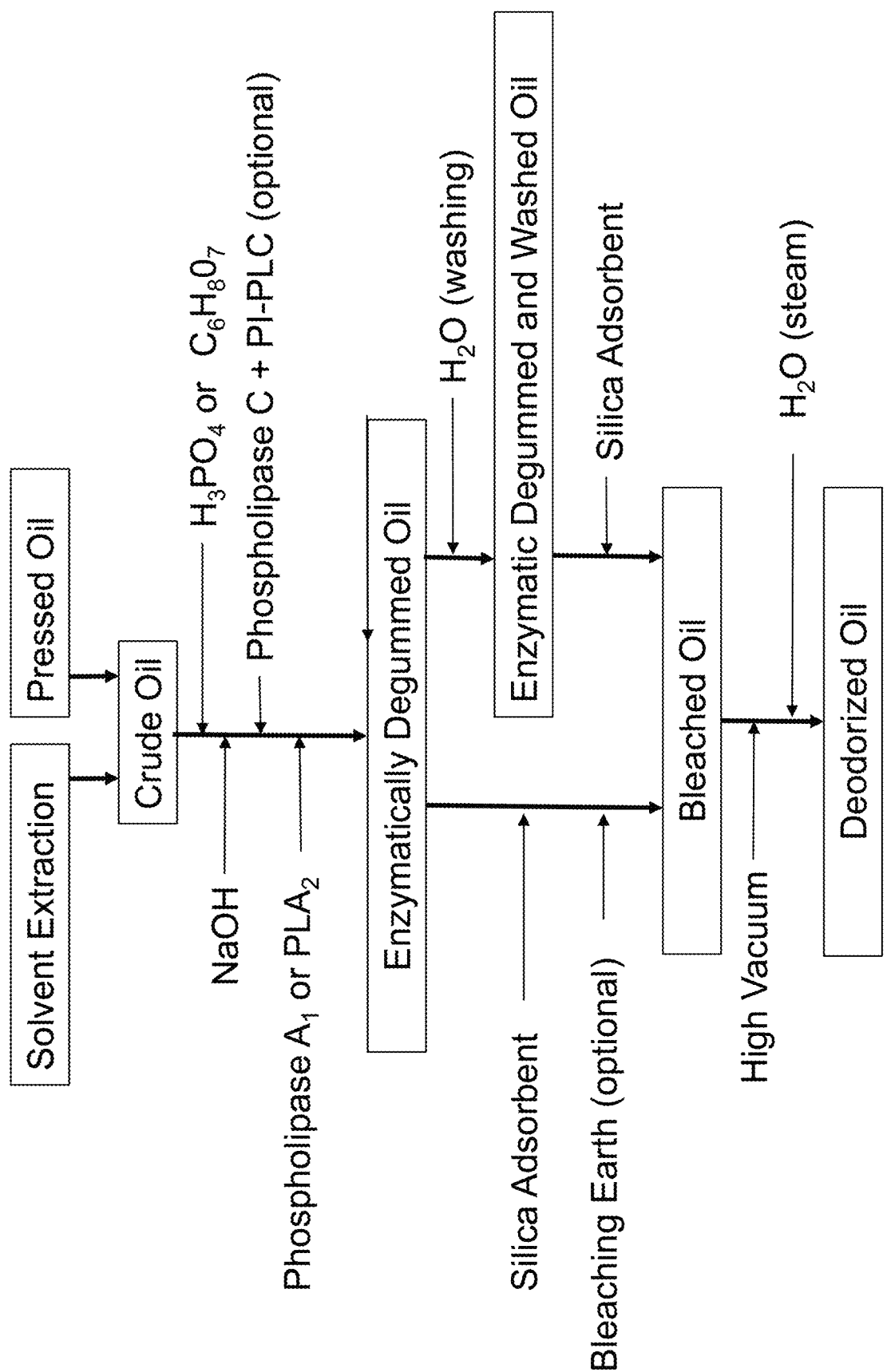
FIG. 12: Schematic presentation of an enzymatic degumming/physical refining process modified to include treatment with a silica adsorbent of the present disclosure, but without decolorase treatment. The enzymatically degummed oil or the enzymatically degummed and washed oil is contacted with a silica adsorbent of the present disclosure, and optionally with bleaching earth, optionally under vacuum, to remove chlorophyll derivatives and trace metals, as described herein.
Figure 13:
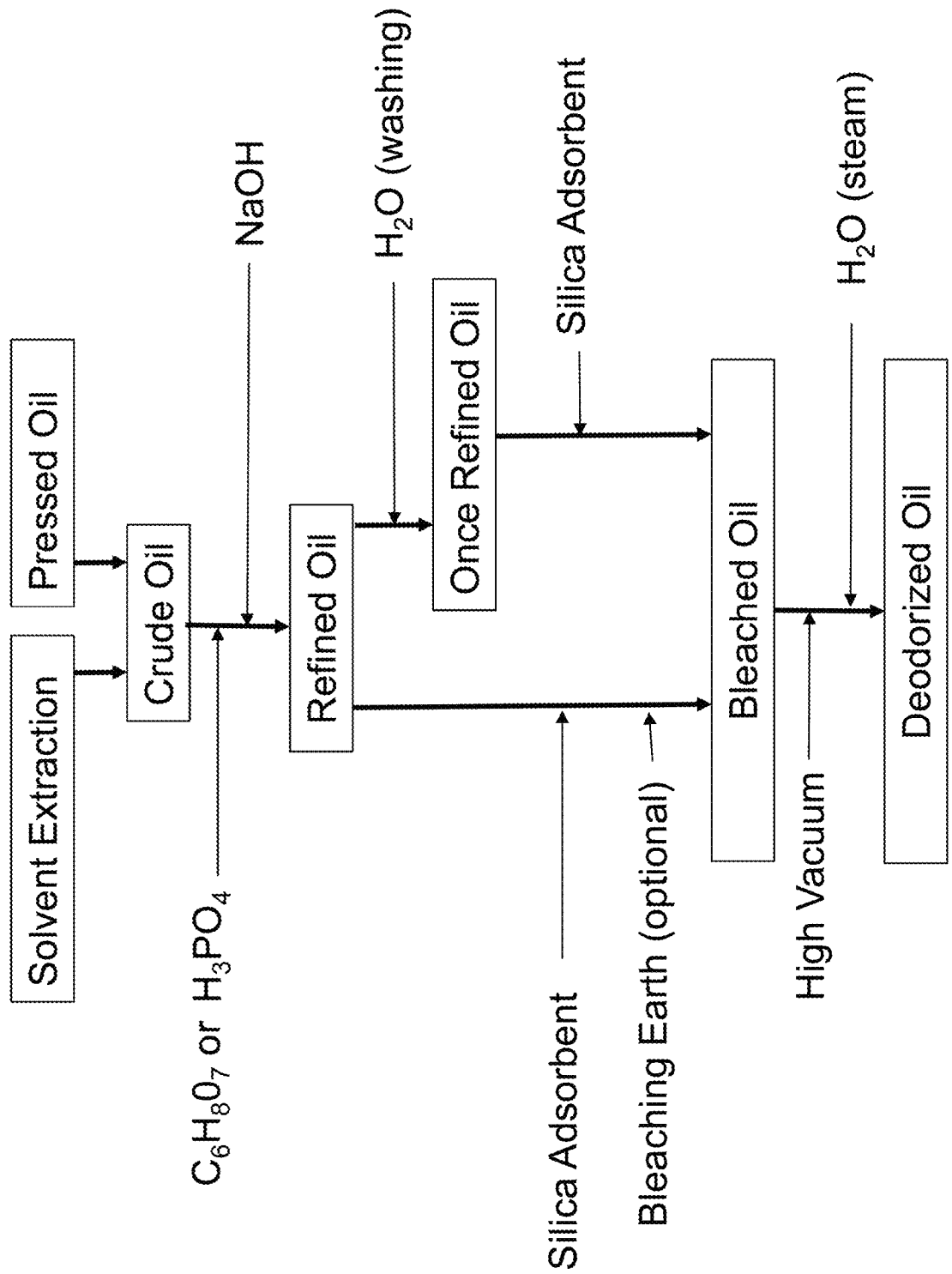
FIG. 13: Schematic presentation of a chemical refinery process for triacylglycerol based oils, modified to include treatment with a silica adsorbent of the present disclosure, but without decolorase treatment. The refined oil or the once refined oil is contacted with a silica-based adsorbent of the present disclosure, and optionally with bleaching earth, optionally under vacuum, to remove chlorophyll derivatives and trace metals, as described herein.

The term "control sequence" can be used interchangeably with the term "expression-regulating nucleic acid sequence". The term as used herein refers to nucleic acid sequences necessary for and/or affecting the expression of an operably linked coding sequence in a particular host organism, or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgamo sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign (heterologous) to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

The term "chlorophyll derivatives" as used herein includes chlorophyll substrates and chlorophyll products. Chlorophyll substrates comprise chlorophyll, pheophytin and pyropheophytin. Chlorophyll products comprise chlorophyllide, pheophorbide and pyropheophorbide. Chlorophyll derivatives comprise so-called a and b compounds.

The term "decolorase" (as well as variations thereof, including the phrase "a polypeptide having decolorase activity"), as used herein, means the polypeptide is capable of converting one or more chlorophyll substrate into a chlorophyll product. For instance, the polypeptide may be capable of hydrolyzing chlorophyll into chlorophyllide; hydrolyzing pheophytin into pheophorbide; and/or hydrolyzing pyropheophytin into pyropheophorbide. The term "decolorase activity" thus may include chlorophyllase activity, pheophytinase activity, pyropheophytinase activity, or combinations thereof.

The term "hydrogel" is used herein to refer to a silica-based adsorbent that has a water content of about 25 wt % or greater, and preferably from about 25 to about 75 wt. %.

The term "amorphous" is used herein to mean a solid material whose constituent atoms, molecules, or ions are arranged in a random, non-ordered pattern that extends in all three directions, which may be determined by X-ray diffraction or differential scanning calorimetry.

The term "porous", as used herein, refers to materials having an internal porosity of 0.1 cc/g or greater as measured by Barrett-Joyner-Halenda (BJH) nitrogen porosimetry as described in DIN 66134.

The term "treated", as used herein with reference to treating with an alkaline earth metal oxide, refers to the intimate mixing of silica and the alkaline earth metal oxide under high shear conditions.

The term "particle surface area" is defined as meaning a particle surface area as measured by the Brunauer Emmet Teller (BET) nitrogen adsorption method.

The phrase "median particle size" refers to median particle size (D50, which is a volume distribution with 50 volume percent of the particles being smaller than this number and 50 volume percent of the particles being bigger than this number in size), measured by dynamic light scattering when the particles are slurried in water or an organic solvent such as acetone or ethanol.

The term "triacylglycerol-based oil" refers to an oil comprising triacylglycerol.

The term "expression" includes any step involved in the production of the polypeptide including, but not limited to, transcription, post transcriptional modification, translation, post-translational modification, and secretion.

An expression vector comprises a polynucleotide coding for a polypeptide, operably linked to the appropriate control sequences (such as a promoter, RBS/Shine Delgado and transcriptional and translational stop signals) for transcription and/or translation in vitro, or in the host cell, of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell.

A host cell may be a prokaryotic, archaebacterial, or eukaryotic host cell. A prokaryotic host cell may be, but is not limited to, a bacterial host cell. A eukaryotic host cell may be, but is not limited to, a yeast, a fungus, an amoeba, an alga, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

The term "promoter" is defined herein as a DNA sequence that binds RNA polymerase and directs the polymerase to the correct downstream transcriptional start site of a nucleic acid sequence to initiate transcription. A promotor sequence may be native of or heterologous relative to the nucleic acid sequence encoding the polypeptide.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term "recombinant" is synonymous with "genetically modified" and "transgenic".

The terms "sequence identity" and "sequence homology" are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region.

The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 1, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

DETAILED DESCRIPTION OF THE DISCLOSURE

The present disclosure relates to processes for removing impurities, including phosphorus-containing compounds such as phosphorus gums, soap, trace metals, chlorophyll derivatives, free fatty acids, and the like, from oils, and in particular from triacylglycerol-based oils. More particularly, the present disclosure is directed to adsorbents comprising an amorphous, porous silica that has been treated with an alkaline earth metal oxide, and the use of such adsorbents, to remove impurities from oils.

It has now been discovered that treating a porous, amorphous silica having a specified water content with alkaline earth metals such as magnesium, and in particular with alkaline earth metal oxides, such as magnesium oxide, results in an adsorbent having an improved ability to remove impurities, such as chlorophyll derivatives and trace metals, from oils, as compared to previously known silicas. It has further been discovered that alkaline earth metal oxide-treated silica adsorbents having a pH of about 7 or greater, and preferably from about 7 to about 10, are capable of removing more impurities (e.g., trace metals, chlorophyll derivatives, etc.) from triacylglycerol-based oils than are prior adsorbents based on other types of silicas, such as xerogel, or acidic hydrogels.

Thus, in one aspect, the present disclosure is directed to a process for treating an oil comprising a chlorophyll derivative, the process comprising contacting the oil with an adsorbent, wherein the adsorbent comprises a silica, and in particular a porous, amorphous silica, that has been treated with an alkaline earth metal oxide, such as MgO, wherein the adsorbent has a pH of about 7 or greater, and a water content of about 3 wt. % or greater, or preferably about 10 wt. % or greater, or from about 25 to about 75 wt. %. In one particular embodiment, the adsorbent is a hydrogel, and has a pH of from about 7 to about 10, and a water content of from about 25 to about 75 wt. %, and comprises from about 2.5 to about 15 wt. %, or from about 5 to about 25 wt %, or from about 10 to about 20 wt % of MgO, on a dry basis.

In one embodiment, the adsorbent comprises a porous, amorphous silica treated with an alkaline earth metal oxide in an amount sufficient to provide about 0.1 wt. % or greater, and more typically, from about 1 wt. % to about 40 wt. %, or from about 5 wt. % to about 25 wt. %, or from about 10 to about 20 wt %, or from about 2.5 wt. % to about 15 wt. %, of alkali earth metal oxide, on a dry basis. In one particular embodiment, the silica is treated with magnesium oxide (MgO), and the amorphous silica is a gel. In such embodiments, the adsorbent comprises about 0.1 wt % or greater of MgO, or from about 1 wt. % to about 40 wt. %, or from about 2.5 wt. % to about 15 wt. %, or from about 5 wt. % to about 25 wt. %, or from about 5 wt. % to about 15 wt. %, or from about 10 wt. % to about 20 wt. %, or from about 10% to about 15 wt. % of MgO, on a dry basis. In one particular embodiment, the adsorbent comprises from about 10 wt. % to about 20 wt. % of MgO.

In some embodiments, the adsorbent of the present disclosure has a molar ratio of MgO to $SiO_2$ of from about 1:3.8 to about 1:26, including from about 1:12.77 to about 1:3.3, or from about 1:12.77 to about 1:4.89, or from about 1:8.09 to about 1:4.90, or from about 1:5.44 to about 1:4.89. In one particular embodiment, the adsorbent has a molar ratio of from about 1:5.44 to about 1:4.89 of MgO to $SiO_2$.

The adsorbent of the present disclosure may have a water content of at least about 3 wt. %, and more typically, about 10 wt. % or greater, about 20 wt. % or greater, or even about 55 wt. % or greater. In certain embodiments, the adsorbents of the present disclosure are advantageously prepared from silica hydrogels, and have a water content of from about 25 wt. % to about 75 wt. %. In other embodiments, the adsorbents have a water content of from about 30 wt. % to about 65 wt. %, or from about 40 wt. % to about 70 wt. %, or from about 50 wt. % to about 65 wt. %, or from about 55 wt. % to about 67 wt. %, or from about 58 wt. % to about 65 wt. %.

The adsorbents of the present disclosure have a pH of about 7 or greater, including from about 7 to about 10, or from about 7.5 to about 9.7, or from about 8.0 to about 9.5, or from about 8.0 to about 9.0, or from about 8.2 to about 9.3. As discussed herein, and as demonstrated in the examples, the adsorbents of the present disclosure have been discovered to be superior at removing impurities from oils, as compared to prior adsorbents based on acidic hydrogels.

The adsorbent of the present disclosure may have a median particle size of from about 0.1 to about 2000 microns, including from about 1 to about 1000 microns, or from about 2 to about 500 microns, or from about 5 to about 50 microns. In one embodiment, the adsorbent has a median particle size of from about 10 to about 30 microns.

The adsorbents of the present disclosure may have a surface area of about 50 $m^2/g$ or greater, including about 300 $m^2/g$ or greater, or about 650 $m^2/g$ or greater. In some embodiments, the adsorbent of the present disclosure has a surface area of from about 50 $m^2/g$ to about 800 $m^2/g$, or from about 300 $m^2/g$ to about 700 $m^2/g$, as determined by BET surface measurement.

The adsorbent of the present disclosure may have a pore volume of about 0.1 cc/g or great, preferably about 0.4 cc/g or greater. In some embodiments, the pore volume of the adsorbent may range from about 0.2 cc/g to about 2.0 cc/g, or from about 0.7 cc/g to about 2.0 cc/g, as determined by nitrogen porosimetry.

In one particular embodiment, the adsorbent of the present disclosure comprises an amorphous silica gel that has been treated with magnesium oxide (MgO), and that has a pH of from about 7 to about 10, and comprises from about 2.5 wt. % to about 15 wt. % MgO, on a dry basis, and has a water content of from about 25 wt. % to about 75 wt. %. More particularly, in one embodiment, the adsorbent of the present disclosure comprises an amorphous silica gel that has been treated with MgO, and that has a pH of from about 8 to about 9, comprises from about 10 wt. % to about 20 wt. % of MgO, on a dry basis, and has a water content of from about 50 wt. % to about 65 wt. %.

Suitable silicas that can be used to prepare the adsorbents of the present disclosure include amorphous porous silica gels and precipitates having a moisture content of about 3 wt. % or greater in the pores of the silica. In one embodiment, the amorphous silica is a "hydrogel" having a moisture content of about 25 wt. % or greater, preferably greater than 40 wt. %, most preferably greater than 50 wt. % and even more preferably, from about 30 to about 65 wt. % moisture. In some embodiments, suitable silica hydrogels include, but are not limited to, commercially available silica gels, such as TRISYL® silica and TRISYL® 300 (W.R. Grace & Co.-Conn., Columbia, Md.).

In another embodiment, a substantially moisture-free silica may be used as a starting silica. By "substantially water free" is meant that the silica used to prepare the adsorbent has less than about 15% moisture. The substantially water-free silica is subsequently hydrated by contacting the gel with a sufficient amount of water to provide the desired moisture content, i.e., about 30 wt. % or greater, preferably in the pores of the silica prior to combining with the alkaline earth metal oxide. The amount of water to be added correlates to the pore volume of the specific silica used, and can readily be determined by those skilled in the art. Non-limiting descriptions of the preparation of silicas suitable for use in the processes of the present disclosure are set forth in the examples.

Suitable alkaline earth metal oxide useful to prepare the adsorbents of the disclosure include, but are not limited to, magnesium oxide, calcium oxide, strontium oxide, barium oxide, beryllium oxide or combinations thereof. Preferably, the alkaline earth metal oxide is magnesium oxide.

The adsorbents of the present disclosure may be prepared by physically blending, preferably under high shear conditions, the desired amount of an alkaline metal oxide powder with the amorphous silica gel having the desired water content. The blending is conducted for a time and a temperature sufficient to provide free-flowing powder. Preferably, the blending is conducted at a temperature ranging from about room temperature to about 100° C. and for a time sufficient to obtain a homogeneous mixture, e.g. about 1 sec or greater. The final adsorbent of the invention comprises an alkaline earth metal oxide treated silica gel having a moisture content of about 3 wt. % or greater and a pH of about 7 or greater. In one embodiment the final adsorbent is a free-flowing powder provided by W.R. Grace & Co.-Conn under the product designation SP-2115 which product contains from about 10 to about 13 wt. % magnesium oxide, on a dry basis, a water content of from about 50 to about 65% and a pH of about 8.2 to about 9.3.

In general, the processes of the present disclosure comprise contacting the oil with an adsorbent of the present disclosure in an amount effective to remove impurities from the oil. In a non-limiting embodiment, the oil is contacted with the adsorbent of the present disclosure in an amount of about 10 wt. % or less, based on the weight of the oil. In other embodiments, the oil is contacted with the adsorbent in an amount of from about 0.01 wt. % to about 10 wt. %, or in an amount of from about 0.1 wt. % to about 8 wt. %, or in an amount of about 0.1 wt. % to about 5 wt. %, or in an amount of about 0.1 wt. % to about 1 wt. %, or in an amount of about 0.1 wt. % to about 0.5 wt. %, or in an amount of about 0.1 wt. % to about 0.4 wt. %, or in an amount of about 0.1 wt. % to about 0.3 wt. %, or in an amount of about 0.1 wt. % to about 0.2 wt. %, based on the weight of the oil.

In certain embodiments, the oil may be contacted with an adsorbent of the present disclosure at a temperature of less than about 100° C., or more typically, at a temperature of from about 60° C. to less than about 100° C., including at a temperature of about 80° C. In some embodiments, the oil may be contacted with an adsorbent of the present disclosure under vacuum at a temperature of less than about 110° C., such as at a temperature of from about 70° C. to about 130° C., or at a temperature of about 100° C. In one embodiment, the vacuum may be from about 50 to about 700 mbar, and more typically is about 100 mbar. In one embodiment, the oil is contacted with the adsorbent of the present disclosure under vacuum of about 100 mbar at a temperature of about 100° C. In another embodiment, the oil is contacted with the adsorbent of the present disclosure at a temperature of from about 60° C. to less than about 100° C., or at a temperature of about 80° C., followed by application of a vacuum of from about 50 to about 700 mbar, and more typically about 100 mbar, and an increase in temperature to about 70° C. to about 130° C. In one particular embodiment, the oil is contacted with an adsorbent of the present disclosure at a temperature of about 80° C., followed by application of a vacuum of about 100 mbar, and an increase in temperature to about 100° C. In some embodiments, the adsorbent is contacted with the oil for from about 5 to about 240 minutes, including from about 15 to about 60 minutes. Following treatment, the silica may be removed from the oil using any suitable technique, including filtration.

Impurities that may be removed from the oils using the processes of the present disclosure include, but are not limited to, phosphorus-containing compounds, including phosphorus gums, soap, trace metals (such as, but not limited to, sodium, potassium, magnesium, calcium, iron, aluminum, and lead), chlorophyll substrates (including chlorophyll, pheophytin, pyropheophytin), chlorophyll derivatives (including chlorophyllide, pheophorbide, and pyropheophorbide), and free fatty acids (FFA).

The treatment of the oil with an adsorbent of the present disclosure as hereinabove described provides an oil which meets acceptable standards for the trade and transportation of edible oils, including cooking oils. Such standards include those of the National Institute of Oilseed Products (NIOP), the American Oil Chemists Society, and the ISO.

Oils that may be treated using the processes of the present disclosure include, but are not limited to, a triacylglycerol-based oil selected from the group consisting of canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, sesame oil, soybean oil, sunflower seed oil, tall oil, tsubaki oil, vegetable oil, and an oil from algae. In one embodiment, the oil is an oil from algae.

The adsorbent of the present disclosure may be used to remove impurities from oils at a variety of stages during oil processing. For instance, the oil to be treated may be selected from the group consisting of a crude non-degummed oil, a degummed oil, a caustic refined oil, a caustic refined and water washed oil, or a water degummed oil. In one embodiment, the oil is a crude oil, and the process comprises contacting a crude oil with a silica of the present disclosure.

In another embodiment, the oil is first subjected to decolorase treatment prior to contacting with the adsorbent. For instance, in one embodiment, the process comprises contacting an oil comprising a chlorophyll derivative with a polypeptide having decolorase activity, or with a composition comprising the polypeptide, to produce a decolorase-treated oil, and contacting the decolorase-treated oil with an adsorbent of the present disclosure. Examples of suitable polypeptides having decolorase activity that may be used in the processes of the present disclosure include, but are not limited to, those polypeptides discussed in detail hereinafter. Suitable processes for producing decolorase-treated oil, as well as various oil processing methods, are also described in detail hereinafter.

Treatment of the oil with an adsorbent of the present disclosure advantageously reduces the level of impurities relative to the level of impurities in the oil prior to contact with the adsorbent. For example, contacting an oil (including a decolorase-treated oil) with a silica of the present disclosure may reduce the total concentration of chlorophyll derivatives (including chlorophyll substrates and/or chlorophyll products) in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll derivatives (by weight) present in the oil prior to contact with the silica.

In another embodiment, the chlorophyll derivative in the oil comprises pyropheophytin, and contacting the oil (including a decolorase-treated oil) with an adsorbent of the present disclosure may reduce the total concentration of pyropheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pyropheophytin (by weight) present in the oil prior contact with the adsorbent.

In another embodiment, the chlorophyll derivative in the oil comprises pheophytin, and contacting the oil (including a decolorase-treated oil) with an adsorbent of the present disclosure may reduce the total concentration of pheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pheophytin (by weight) present in the oil prior to contact with the silica.

In another embodiment, the chlorophyll derivative in the oil comprises chlorophyll, and contacting the oil (including a decolorase-treated oil) with a silica of the present disclosure reduces the total concentration of chlorophyll in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll (by weight) present in the oil prior to prior to contact with the silica.

In another embodiment, contacting an oil (including a decolorase-treated oil) with a silica-based adsorbent of the present disclosure may reduce the total concentration of trace metal impurities (such as, but not limited to, sodium, potassium, magnesium, calcium, iron, aluminum, and lead), in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of trace metal impurities (by weight) present in the oil prior to contact with the adsorbent.

In another embodiment, an oil comprising a chlorophyll derivative, and in particular a chlorophyll substrate, is contacted with a polypeptide having decolorase activity, or with a composition comprising the polypeptide, to produce a decolorase-treated oil. In one such embodiment, the chlorophyll substrate comprises pyropheophytin, the decolorase treatment converts at least a portion of the pyropheophytin into pyropheophorbide, and contacting the decolorase-treated oil with an adsorbent of the present disclosure reduces the total concentration of pyropheophorbide in the decolorase-treated oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pyropheophorbide (by weight) present in the decolorase-treated oil prior contact with the adsorbent. In another embodiment, the chlorophyll substrate comprises pheophytin, the decolorase treatment converts at least a portion of the pheophytin into pheophorbide, and contacting the decolorase-treated oil with an adsorbent of the present disclosure reduces the total concentration of pheophorbide in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pheophorbide (by weight) present in the decolorase-treated oil prior to contact with the adsorbent. In another embodiment, the chlorophyll substrate comprises chlorophyll, the decolorase treatment converts at least a portion of the chlorophyll into chlorophyllide, and contacting the decolorase-treated oil with an adsorbent of the present disclosure reduces the total concentration of chlorophyllide in the decolorase-treated oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyllide (by weight) present in the decolorase-treated oil prior to prior to contact with the adsorbent.

In one embodiment, the process of the present disclosure further comprises contacting the oil or the decolorase-treated oil with an additional enzyme selected from the group consisting of a phospholipase, a pheophytinase, a pyropheophytinase, a pheophorbidase, a chlorophyllase, and combinations thereof.

In another embodiment, the present disclosure is directed to a process for treating an oil comprising pyropheophytin, the process comprising contacting the oil with a polypeptide having pyropheophytinase activity, or with a composition comprising the polypeptide, wherein pyropheophytin is converted into pyropheophorbide, and optionally where pheophytin is converted into pheophorbide, to produce a pyropheophytinase-treated oil, and contacting the pyropheophytinase treated oil with an adsorbent of the present disclosure.

Polypeptides

Any suitable polypeptide having decolorase activity may be used in the processes of the present disclosure. In one particular embodiment, the polypeptide is a polypeptide having pyropheophytinase activity, and is selected from the group consisting of:

a. an isolated polypeptide which has at least 80%, 85%, 86%, 87%, 88%, 89%, 90%, 91%, 92%, 93%, 94%, 95%, 96%, 97%, 98% or at least 99%, or which has 100% identity to amino acids 1 to 318 of SEQ ID NO: 1; and, b. a polypeptide encoded by a nucleic acid sequence that has at least 80%, 85%, 86%, 87%, 88%, 89%, 90%, 91%, 92%, 93%, 94%, 95%, 96%, 97%, 98%, or 99%, or which has 100% identity to the nucleic acid sequence of SEQ ID NO: 2.

A polypeptide having pyropheophytinase activity may be a polypeptide which has at least 80% identity to amino acids 1 to 318 of SEQ ID NO: 1. A polypeptide as disclosed herein may have at least 85%, 86%, 87%, 88%, 89%, 90%, 91%, 92%, 93%, 94%, 95%, 96%, 97%, 98% or at least 99% identity to amino acids 1 to 318 of SEQ ID NO: 1. A polypeptide as disclosed herein may have at least 85%, 86%, 87%, 88%, 89%, 90%, 91%, 92%, 93%, 94%, 95%, 96%, 97%, 98%, or at least 99% identity to amino acids 1 to 318 of SEQ ID NO: 1. A polypeptide having pyropheophytinase activity as disclosed herein may comprise, or contain, or consist of amino acids 1 to 318 of SEQ ID NO: 1. A polypeptide having pyropheophytinase activity may comprise, or contain, or consist of amino acids 2 to 318 of SEQ ID NO: 1. Surprisingly, it was found that a polypeptide which has at least 80% identity to amino acids 1 to 318, or to amino acids 2 to 318 of SEQ ID NO: 1 comprises pyropheophytinase activity.

A polypeptide having pyropheophytinase activity hydrolyses pyropheophytin into pyropheophorbide (see also FIG. 1). A polypeptide having pyropheophytinase activity as disclosed herein preferably hydrolyses pyropheophytin a and pyropheophytin b into their pyropheophorbide a and b compounds. Accordingly, pyropheophytinase activity can be determined by the formation of pyropheophorbide.

A polypeptide as disclosed herein may further comprise pheophytinase activity. A polypeptide having pheophytinase activity hydrolyses pheophytin into pheophorbide. Preferably a polypeptide as disclosed herein hydrolyses pheophytin a and/or pheophytin b into their respective pheophorbide compounds. Accordingly, pheophytinase activity can be determined by the formation of pheophorbide.

A polypeptide as disclosed herein having pyropheophytinase activity may also comprise chlorophyllase activity. A polypeptide having chlorophyllase activity hydrolyses the conversion of chlorophyll into chlorophyllide. Preferably a polypeptide as disclosed herein hydrolyses chlorophyll a and/or chlorophyll b into their respective chlorophyllide compounds.

In one embodiment, a polypeptide as disclosed herein has pyropheophytinase activity, pheophytinase activity, and chlorophyllase activity.

Determination of pyropheophytin, pheophytin, chlorophyll and the reaction products pyropheophorbide, pheophorbide, chlorophyllide can be performed by HPLC as disclosed in the Examples.

A polypeptide may be derivable from any suitable origin, for instance from plant, algae or cyanobacteria. A polypeptide as disclosed herein may be derived from plant, for instance from *Hordeum* sp., or *Triticum* sp., for instance *Hordeum vulgare* or *Triticum aestivum*. A polypeptide as disclosed herein may also be generated using standard molecular techniques e.g. de novo synthesis.

A polypeptide having decolorase activity such as pyropheophytinase activity as disclosed herein may be an isolated, a pure, recombinant, synthetic or a variant polypeptide. A polypeptide as disclosed herein may be purified. Purification of proteins can be performed by several methods known to a person skilled in the art.

A variant polypeptide of a polypeptide having pyropheophytinase activity as disclosed herein may be a polypeptide that has at least 85%, 86%, 87%, 88%, 89%, 90%, 91%, 92%, 93%, 94%, 95%, 96%, 97%, 98%, or at least 99% identity to amino acids 1 to 318 of SEQ ID NO: 1, or to amino acids 2 to 318 of SEQ ID NO:1.

A polypeptide having pyropheophytinase activity as disclosed herein may be a polypeptide, for instance a variant polypeptide, which, when aligned with an amino acid sequence according to SEQ ID NO: 1 comprises a substitution, deletion and/or insertion at one or more amino acid positions as compared to SEQ ID NO: 1. For instance, a polypeptide as disclosed herein may be a polypeptide, which when aligned with a polypeptide of SEQ ID NO:1 comprises 1, 2, 3, 4, 5, 6, 7, 8, 9, 10, 11 or 12, or more amino substitutions, deletions and/or insertions as compared to SEQ ID NO: 1, whereby the polypeptide still has the activity or function of a polypeptide as disclosed herein. The skilled person will appreciate that these minor amino acid changes in a polypeptide as disclosed herein may be present (for example naturally occurring mutations) or made (for example using r-DNA technology) without loss of the protein function or activity. In case these mutations are present in a binding domain, active site, or other functional domain of the polypeptide a property of the polypeptide may change but the polypeptide may keep its activity. In case a mutation is present which is not close to the active site, binding domain, or other functional domain, less effect may be expected.

A polypeptide as disclosed herein may be encoded by any suitable polynucleotide sequence, as long as the polypeptide exhibits pyropheophytinase activity as disclosed herein. Typically, a polynucleotide sequence encoding a polypeptide having pyropheophytinase activity as disclosed herein is a codon optimized sequence, or a codon pair optimized sequence for expression of the polypeptide in a particular host cell.

Compositions

The processes of the present disclosure may further comprise contacting an oil with a composition comprising a polypeptide having decolorase activity, such as disclosed herein.

Such a composition may comprise a carrier, an excipient, or other compounds. Typically, a composition, or a formulation, comprises a compound with which a polypeptide having decolorase activity (including pyropheophytinase activity) may be formulated. Suitable formulations include liquid formulations, such as emulsions, suspensions and solutions, pastes, gels, granules and freeze-dried or spray-dried powders.

An excipient as used herein is an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the polypeptide or the composition comprises an encapsulated polypeptide in liquid matrices like liposomes or gels like alginate or carrageenans. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

A composition as disclosed herein may also comprise a carrier comprising a polypeptide as disclosed herein. For instance, a polypeptide as disclosed herein can be immobilized on silica. A polypeptide as disclosed herein may be bound or immobilized to a carrier by known technologies in the art.

A composition comprising a polypeptide having decolorase activity (including pyropheophytinase activity) as disclosed herein may comprise one or more further enzymes, for instance a lipase, such as phospholipase, for instance phospholipase A, B and/or C, a chlorophyllase, pheophytinase and/or a pyropheophytinase. A further enzyme may be a phospholipase C (PLC), a phosphatidyl-inositol PLC and/or a phospholipase A, such as a phospholipase A1 or a phospholipase A2.

A composition comprising a polypeptide having decolorase activity (including pyropheophytinase activity) as disclosed herein may comprise cell fractions for instance cell fractions from a host cell wherein the polypeptide having decolorase activity has been produced. Cell fractions may be generated by various methods for instance after disruption of the host cell by sonification and/or use of glass beads.

The present disclosure also relates to a process for preparing a composition comprising a polypeptide as disclosed herein, which may comprise spray drying a fermentation medium comprising the polypeptide, or granulating, or encapsulating a polypeptide as disclosed herein, and preparing the composition.

Nucleic Acids, Expression Vectors, and Recombinant Host Cells

The present disclosure also relates to a nucleic acid which has at least 80%, 85%, 86%, 87%, 88%, 89%, 90%, 91%, 92%, 93%, 94%, 95%, 96%, 97%, 98%, or at least 99% identity or which has 100% identity to a nucleic acid sequence encoding a polypeptide as disclosed herein. A nucleic acid as disclosed herein may be a nucleic acid which has at least 80%, 85%, 86%, 87%, 88%, 89%, 90%, 91%, 92%, 93%, 94%, 95%, 96%, 97%, 98% or at least 99% identity to SEQ ID NO: 2. A nucleic acid as disclosed herein may comprise or contain SEQ ID: NO:2. A nucleic acid as disclosed herein may further comprise a promotor sequence and/or other control sequence.

A nucleic acid encoding a polypeptide having decolorase activity (including pyropheophytinase activity) as disclosed herein may be a codon optimized, or a codon pair optimized sequence for expression of a polypeptide as disclosed herein in a particular host cell. A host cell may for instance be *Pseudomonas* sp, for instance *Pseudomonas fluorescens*.

In one other embodiment of the present invention a nucleic acid is disclosed that is an isolated, pure, recombinant, synthetic or variant nucleic acid of the nucleic acid of SEQ ID NO: 2. A variant nucleic acid sequence may for instance have at least 80%, 85% 86%, 87%, 88%, 89%, 90%, 91%, 92%, 93%, 94%, 95%, 96%, 97%, 98%, or at least 99% sequence identity to SEQ ID NO: 2.

The present invention also relates to an expression vector comprising a nucleic acid as disclosed herein, wherein the nucleic acid is operably linked to one or more control sequence(s) that direct expression of the polypeptide in a host cell.

There are several ways of inserting a nucleic acid into a nucleic acid construct or an expression vector which are known to a skilled person in the art, see for instance Sambrook & Russell, *Molecular Cloning: A Laboratory Manual*, 3rd Ed., CSHL Press, Cold Spring Harbor, N.Y., 2001. It may be desirable to manipulate a nucleic acid encoding a polypeptide of the present invention with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter.

Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Promoters suitable in bacterial hosts are promoters which may be selected from the group of the *E. coli* lac promoter, the aroH promoter, the araBAD promoter, the T7 promoter, the trc promoter, the tac promoter and the trp promoter. Other examples of promoters are the promotor of the *Streptomyces coelicolor* agarase gene (dagA), the promoter of the *Bacillus lentus* alkaline protease gene (aprH), the promoter of the *Bacillus licheniformis* alkaline protease gene (subtilisin Carlsberg gene), the promoter of the *Bacillus subtilis* levansucrase gene (sacB), the promoter of the *Bacillus subtilis* alpha amylase gene (amyE), the promoter of the *Bacillus licheniformis* alpha amylase gene (amyL), the promoter of the *Bacillus stearothermophilus* maltogenic amylase gene (amyM), or the promoter of the *Bacillus amyloliquefaciens* alpha-amylase gene (amyQ). Another example is a "consensus" promoter having the sequence TTGACA for the "−35" region and TATAAT for the "−10" region.

The present invention also relates to a recombinant host cell comprising a nucleic acid as disclosed herein, or an expression vector as disclosed, wherein the nucleic acid is heterologous to the host cell. A recombinant host cell as disclosed herein may be a host cell wherein the nucleic acid and the encoding polypeptide having decolorase (including pyropheophytinase) activity as disclosed herein are heterologous to the host cell.

A host cell as disclosed herein may be any suitable microbial, plant or insect cell. A suitable host cell may be a fungal cell, for instance from the genus *Acremonium, Aspergillus, Chrysosporium, Fusarium, Penicillium, Rasamsonia, Trichoderma, Saccharomyces, Kluyveromyces, Pichia*, for instance *Aspergillus niger, Aspergillus awamori, Aspergillus foetidus, A. oryzae, A. sojae, Rasamsonia emersonii Chrys-*

*osporium lucknowense, Fusarium oxysporum, Trichoderma reesei* or, *Saccharomyces cerevisiae, Kluyveromyces lactis,* or *Pichia pastoris.*

A host cell may be a prokaryotic cell, such as a bacterial cell. The term "bacterial cell" includes both Gram-negative and Gram-positive microorganisms. Suitable bacteria may be from the genus *Escherichia, Pseudomonas, Bacillus, Enterobacter, Lactobacillus, Lactococcus,* or *Streptomyces.* A bacterial cell may be from the species *B. subtilis, B. amyloliquefaciens, B. licheniformis, B. puntis, B. megaterium, B. halodurans, B. pumilus, Pseudomonas zeaxanthinifaciens, Pseudomonas fluorescens,* or *E. coli.*

A suitable bacterial host cell may for instance be a *Pseudomonas* sp., such as *Pseudomonas fluorescens.*

Methods of Polypeptide Production

Polypeptides suitable for use in the processes of the present disclosure (e.g., polypeptides having decolorase activity, including a polypeptide having pyropheophytinase activity, can be produced by cultivating a host cell as disclosed herein in a suitable fermentation medium under conditions that allow expression of the polypeptide and producing the polypeptide. A skilled person in the art understands how to perform a process for the production of a polypeptide as disclosed herein depending on a host cell used, such as pH, temperature and composition of a fermentation medium. Host cells can be cultivated in shake flasks, or in fermenters having a volume of 0.5 or 1 litre or larger to 10 to 100 or more cubic metres. Cultivation may be performed aerobically or anaerobically depending on the requirements of a host cell. In the event the host cell is *Pseudomonas* sp., for instance *Pseudomonas fluorescens,* cultivation of the host cell is performed under aerobic conditions.

Advantageously, a polypeptide as disclosed herein is recovered or isolated from the fermentation medium, for instance by centrifugation or filtration known to a person skilled in the art. Recovery of a polypeptide having pyropheophytinase activity may also comprise disruption of the cells wherein the polypeptide is produced. Disruption of cells can be performed using glass beads and, or sonification known to a person skilled in the art.

Processes for Treating Oils Comprising Chlorophyll Derivatives with a Polypeptide Having Decolorase Activity In one embodiment, the processes of the present disclosure also comprise treating an oil, comprising a chlorophyll derivative (such a pyropheophytin) with a polypeptide having decolorase activity as disclosed herein, or with a composition comprising a polypeptide as disclosed herein above. In one embodiment, the polypeptide as disclosed herein has pyropheophytinase activity. In another embodiment, the polypeptide has pheophytinase activity. In another embodiment, the polypeptide has pyropheophytinase activity and pheophytinase activity. In another embodiment, the polypeptide has pyropheophytinase activity, pheophytinase activity, and chlorophyllase activity.

As discussed herein, a polypeptide having pyropheophytinase activity is capable of hydrolyzing pyropheophytin into pyropheophorbide, a polypeptide having pheophytinase activity is capable of hydrolyzing the pheophytin into pheophorbide, and a polypeptide having chlorophyllase activity is capable of hydrolyzing chlorophyll into chlorophyllide. Thus, in one embodiment, the decolorase treatment may reduce the level of one or more chlorophyll substrate in the oil. In various embodiments, the chlorophyll substrate may be chlorophyll, pheophytin, and/or pyropheophytin. For example, the treatment with the decolorase may reduce the total concentration of chlorophyll substrates in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll substrate (by weight) present in the oil prior to treatment. The reduction in total concentration of chlorophyll substrate may be the result of conversion of pyropheophytin into pyropheophorbide, pheophytin into pheophorbide, and/or chlorophyll into chlorophyllide.

In another embodiment, the chlorophyll substrate in the oil comprises pyropheophytin, and at least a portion of the pyropheophytin is converted into pyropheophorbide as a result of the decolorase treatment. For example, the decolorase treatment may reduce the total concentration of pyropheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pyropheophytin (by weight) present in the oil prior to decolorase treatment. The reduction in total concentration of pyropheophytin may be the result of conversion of pyropheophytin into pyropheophorbide. In another embodiment, the chlorophyll substrate in the oil comprises pheophytin, and at least a portion of the pheophytin is converted into pheophorbide as a result of the treatment. For example, the decolorase treatment may reduce the total concentration of pheophytin in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of pheophytin (by weight) present in the oil prior to decolorase treatment. The reduction in total concentration of pheophytin may be the result of conversion of pheophytin into pheophorbide. In such embodiments, the polypeptide exhibits pheophytinase activity.

In another embodiment, the chlorophyll substrate in the oil comprises chlorophyll, and at least a portion of the chlorophyll is converted into chlorophyllide as a result of the decolorase treatment. For example, the decolorase treatment may reduce the total concentration of chlorophyll in the oil by at least 5%, at least 10%, at least 20%, at least 30%, at least 40%, at least 50%, at least 60%, at least 70%, at least 80%, at least 90%, at least 95%, at least 99%, or by 100% by weight, compared to the total concentration of chlorophyll (by weight) present in the oil prior to decolorase treatment. The reduction in total concentration of chlorophyll may be the result of conversion of chlorophyll into chlorophyllide. In such embodiments, the polypeptide exhibits chlorophyllase activity.

An oil comprising pyropheophytin, pheophytin, and/or chlorophyll may further comprise other substrates such as phospholipids. Optionally, a process for treating an oil as disclosed herein further comprises removal of phospholipids, as described hereinafter.

Any oil comprising a chlorophyll derivative, including a chlorophyll substrate, may be treated in accordance with the present process in order to remove one or more undesirable chlorophyll derivative from the oil. The oil may be a triacylglycerol-based oil, including various vegetable- or algal-based oils. In one embodiment, suitable oils that may be used in connection with the present treatment include, but are not limited to the following: canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, sesame oil, soybean oil, sunflower or sunflower seed oil, tall oil, tsubaki oil, vegetable oil, and oil from algae. In one embodiment, an oil that can be treated in accordance with the present disclosure is selected from the group consisting of canola oil, corn oil, olive oil, palm oil, palm kernel oil, peanut oil, rapeseed oil, rice bran oil, sesame oil, soybean oil and sunflower seed oil. In one embodiment, the oil is an oil from algae.

Contacting an oil comprising one or more chlorophyll substrate with a polypeptide having decolorase activity may be performed during any suitable time and at any suitable pH and temperature. Said contacting may be performed at a pH and temperature which are applied during degumming of a triacylglycerol oil. A suitable pH may be from pH 2 to pH 10, for instance from pH 3 to pH 9, from pH 4 to pH 8, from pH 5 to pH 7, from pH 5 to 8, or from pH 6.5 to 7.5. In one embodiment, the polypeptide is contacted with the oil at a pH of from 4.0 to 7.5, or from 4.5 to 8.0, or from 4.5 to 7.0. In one embodiment, the polypeptide is contacted with the oil at a pH of from 4.0 to 5.0, or more specifically at a pH of 4.5. In another embodiment, the polypeptide is contacted at a pH of 7.0.

A suitable temperature for contacting an oil comprising one or more chlorophyll substrate with a polypeptide having decolorase activity as disclosed herein may be from 10° C. to 90° C., for instance from 20° C. to 80° C., from 30° C. to 70° C., from 45° C. to 70° C., from 40° C. to 60° C., or from 50° C. to 65° C.

For instance, contacting an oil comprising one or more chlorophyll substrate with a polypeptide having decolorase activity may be performed at a pH of from 5 to 8, and a temperature of from 40° C. to 60° C., or at a pH of from 4.5 to 7.0 and a temperature of from 40° C. to 60° C., or at a pH of 7.0 and a temperature of from 45° C. to 70° C., or at a pH of 7.0 and a temperature of from 50° C. to 65° C.

The polypeptide having decolorase activity may be dosed into the oil comprising a chlorophyll substrate in any suitable amount. For example, the polypeptide may be dosed in a range of 1 to 50 U/gram of treated oil, such as from 1.4 to 50 U/gram of treated oil, or 5 to 50 U/gram of treated oil. One unit is defined in accordance with the enzyme activity taught in the examples below.

Surprisingly, it was found that a polypeptide having decolorase, such as pyropheophytinase activity as disclosed herein converts a higher amount of chlorophyll substrates to chlorophyll products under acidic and caustic conditions as compared to a reference polypeptide. A reference polypeptide is a polypeptide comprising the amino acid sequence according to SEQ ID NO: 12. SEQ ID NO: 12 comprises *Chlamydomonas reinhardtii* chlorophyllase having pyropheophytinase activity.

Contacting an oil comprising one or more chlorophyll substrate with a polypeptide having decolorase activity may be performed during oil degumming. Oil degumming comprises several processing steps, such as pressing and/or hexane extraction, degumming, for instance in the presence of degumming enzymes such as phospholipases as disclosed in WO2005/086900 or WO2011/046812, refining, bleaching and deodorization. Contacting an oil comprising one or more chlorophyll substrate with a polypeptide having pyropheophytinase activity, pheophytinase activity, and/or chlorophyllase activity may be performed during a bleaching step in oil degumming processing, as described in more detail hereinafter.

Contacting a polypeptide having pyropheophytinase activity with an oil, such as a triacylglycerol oil or an algal oil, may comprise dispersing an aqueous solution comprising the polypeptide as disclosed herein in the oil. An oil that is treated with a polypeptide having pyropheophytinase activity typically comprises 0.5 to 10 w/w % of water, for instance 1 to 10 w/w % of water, 1 to 5 w/w % of water, 2 to 8 w/w % of water, 2 to 4 w/w % of water, 3 to 6 w/w % of water, 0.5 to 5 w/w % of water, 1 to 3 w/w %, 1.5 to 2 w/w % of water, or 5 w/w % water.

The polypeptide may be contacted with the oil for a period of from 5 minutes to 24 hours, from 10 minutes to 12 hours, from 15 minutes to 10 hours, from 0.5 to 24 hours, from 1 to 12 hours, from 1.5 to 6 hours, or from 2 to 4 hours. In one embodiment, the polypeptide may be contacted with the oil for 2 hours. After said contacting, a water phase and an oil phase are usually separated.

An oil that is treated in a process as disclosed herein may be a crude non-degummed, degummed (water degummed, enzyme degummed, or acid degummed), caustic refined or a caustic refined and water washed oil or a water degummed oil. In one particular embodiment, the oil comprises a non-degummed crude oil. A crude oil usually is an oil that is mechanically pressed, or solvent extracted, and wherein the oil usually contains Free Fatty Acids (FFA) and phospholipids. A degummed oil is an oil wherein the majority of phospholipids have been removed from a crude oil. Usually a degummed oil comprises between 0.5 to 200 ppm atomic phosphorous, such as between 1 and 100 ppm atomic phosphorous, such as between 5 and 50 ppm atomic phosphorous. A refined oil is an oil where the FFA have been neutralized by a caustic treatment and removed. A caustic treatment of oil usually comprises treating an oil with sodium hydroxide.

Contacting a polypeptide having decolorase (e.g., pyropheophytinase) activity as disclosed herein with an oil, for instance during degumming of an oil may be performed at any suitable temperature, for instance at a temperature from 45 to 70° C., including from 50 to 65° C.

Contacting a polypeptide having decolorase (e.g., pyropheophytinase) activity as disclosed herein with an oil, for instance during degumming of an oil may be performed at any suitable pH, such as pH of from 3.5 to 8.0, for instance pH 4 to 7.5, for instance pH 4.5 to 7.0

In one embodiment, the treatment process disclosed herein further comprises subjecting the oil to water degumming. As discussed herein, water degumming is usually applied to crude oils containing a high amount of hydratable phospholipids. Due to its mild characteristics, the phospholipids obtained can be used as lecithin (a natural emulsifier). The oil obtained from this process is generally referred to in the industry as being "degummed," despite being only partially degummed.

Thus, in one aspect, the treatment process of the present disclosure comprises contacting an oil (e.g., a non-degummed crude oil), comprising a chlorophyll derivative (such as a chlorophyll substrate), with water and a polypeptide of the present disclosure. Typically, the temperature of the oil is from 45 to 70° C., including from 50 to 65° C. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The polypeptide as disclosed herein and water may be added as a single composition, or the polypeptide may be added separately from the water. Typically, no acid or base is added to the resulting mixture, and the process proceeds at a neutral pH (e.g., around pH 7.0). Following contact with the polypeptide and water, the oil may optionally be mixed using a shear mixer. The oil is subsequently incubated with stirring (e.g., using a continuously stirred reactor) for from 0.5 to 24 hours, or 1 to 12 hours, or 1.5 to 6 hours, or 2 to 4 hours, which aids in hydration of phospholipids present in the oil. Following incubation and stirring, the oil is heated to a temperature of from 70 to 85° C. The resulting oil may be separated by settling, filtration, or the industrial practice of centrifugation. The centrifuge yields two streams, water degummed oil and wet gums.

In another embodiment, the treatment process disclosed herein further comprises subjecting an oil to enzyme assisted water degumming. As discussed herein, enzyme assisted water degumming is usually applied to crude oils containing a high amount of hydratable phospholipids where the goal is to react all of the hydratable phospholipids and convert them into diacylglycerols increasing the oil yield, while maintaining the no-hydratable phospholipids in the oil. Enzymes utilized for this process include phospholipase C (PLC) and phosphatidyl inositol-phospholipase (PI-PLC).

Thus, in one aspect, the treatment process of the present disclosure comprises contacting an oil (e.g., a non-degummed crude oil), comprising a chlorophyll derivative (such as a chlorophyll substrate) with water, a polypeptide of the present disclosure, and an additional enzyme. The additional enzyme may be selected from the group consisting of PLC, PI-PLC and combinations thereof. In one embodiment, the additional enzyme includes both PLC and PI-PLC. Typically, the temperature of the oil is from 45 to 70° C., including from 50 to 65° C. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The PLC (e.g., Purifine PLC) may be added in an amount of from 50 to 500 ppm, including from 100 to 400 ppm, or from 150 to 250 ppm. The PI-PLC may be added in an amount of from 50 to 500 ppm, including from 100 to 400 ppm, or from 150 to 250 ppm. In one embodiment, the additional enzyme is Purifine 4G, which contains both PLC and PI-PLC. In this embodiment, the Purifine 4G may be added in an amount of from 50 to 500 ppm, including from 100 to 400 ppm, or from 150 to 250 ppm. The polypeptide as disclosed herein, additional enzymes, and water may be added as a single composition, or the polypeptide as disclosed herein, additional enzymes, and water may be added separately. Typically, no acid or base is added to the resulting mixture, and the process proceeds at a neutral pH (e.g., around pH 7.0). Following contact with the polypeptide, additional enzymes, and water, the composition may optionally be mixed using a shear mixer. A suitable shear mixer is the continuous shear mixer IKA Dispax Reactor. The composition is subsequently incubated with stirring (e.g., using a continuously stirred reactor) for from 0.5 to 24 hours, or 1 to 12 hours, or 1.5 to 6 hours, or 2 to 4 hours, which aids in conversion of PC, PE, and PI to diacylglycerols in the oil. Following incubation and stirring, the composition is heated to a temperature of from 70 to 85° C., such as 85° C. The resulting composition may be separated by settling, filtration, or the industrial practice of centrifugation. The centrifuge yields two streams, water degummed oil and heavy phase (containing water, denatured protein, and phosphor-compounds).

In another embodiment, the treatment process disclosed herein further comprises subjecting the oil to enzyme degumming. Enzyme degumming may be applied to crude oils or to oils that have been degummed previously by a different method, such as water degumming, enzyme assisted water degumming, or acid degumming. A processor who wishes to produce lecithin for the food or industrial market may water degum the oil prior to further processing. The destruction of the phospholipids is unacceptable in lecithin applications.

Thus, in one aspect, the treatment process of the present disclosure comprises contacting a composition, such as an oil (e.g., a crude oil or previously degummed oil), comprising a chlorophyll derivative (such as a chlorophyll substrate), with a polypeptide of the present disclosure. The pH of the oil may be adjusted prior to contacting with the polypeptide, for example by addition of an acid (e.g., citric or phosphoric acid) in an amount of from 100 to 1000 ppm, including 500 ppm. Typically, the pH is adjusted to a pH of from 4.5 to 8.0, including from 4.5 to 7.0. Typically, the temperature of the oil is from 70 to 85° C. at the time of pH adjustment. Following acid addition, the resulting oil may be mixed for from 5 minutes to 24 hours, depending on the type of mixer (e.g., high shear, agitator, etc.). One skilled in the art will understand that lower mixing times will be needed when high shear mixers are used, while higher mixing times will be needed when less shear is applied (e.g., when using a simple agitator). Following pH adjustment, the composition (e.g., oil) is cooled to from 45 to 70° C., including from 50 to 65° C., and water, a polypeptide of the present disclosure, and optionally an additional enzyme are added. The additional enzyme (when used) may be selected from the group consisting of PLC, PI-PLC, and combinations thereof. In one embodiment, the additional enzyme includes both PLC and PI-PLC. The water may be added in an amount of from 1 to 5 w/w %, including from 2 to 4 w/w %. The polypeptide may be dosed in an amount of 1 to 50 U/gram of treated oil, such as from 1.4 to 50 U/gram of treated oil, or 5 to 50 U/gram of treated oil. The PLC (e.g., Purifine PLC) may be added in an amount of from 50 to 500 ppm, including from 100 to 400 ppm, or from 150 to 250 ppm. The PI-PLC may be added in an amount of from 50 to 500 ppm, including from 100 to 400 ppm, or from 150 to 250 ppm. In one embodiment, the additional enzyme is Purifine 4G, which contains both PLC and PI-PLC. In this embodiment, the Purifine 4G may be added in an amount of from 50 to 500 ppm, including from 100 to 400 ppm, or from 150 to 250 ppm. The polypeptide, additional enzyme (when present), and water may be added as a single composition, or the polypeptide, additional enzymes, and water may be added separately.

Following contact with the polypeptide, additional enzyme (when present), and water, the composition may be mixed using a shear mixer. A suitable shear mixer is the continuous shear mixer IKA Dispax Reactor. Shear mixing is optional, particularly when the composition being treated is, or comprises, a crude, non-degummed oil. The composition is subsequently stirred (e.g., using a continuously stirred reactor) for from 0.5 to 24 hours, or 1 to 12 hours, or 1.5 to 6 hours, or 2 to 4 hours.

Following stirring, a phospholipase A (PLA) enzyme is added to the oil. The PLA enzyme may be a PLA1 enzyme and/or PLA2 enzyme. In one embodiment, the enzyme is a PLA1 enzyme. Sequences of amino acids with phospholipase activity are extensively reported in the art, including phospholipids having activity in triacylglycerol oils. Commercial PLA1 enzymes with phospholipase activity include Lecitase® Ultra and QuaraLowP. Commercial PLA2 enzymes with phospholipase activity include Rohalase Xtra and LysoMax. Any suitable PLA enzyme may be PLA added may vary depending on the manufacturer and the type of continuous stirred-tank reactor used. Following addition of the PLA enzyme, the oil may be mixed using a shear mixer. A suitable shear mixer is the continuous shear mixer IKA Dispax Reactor. The oil is subsequently incubated with stirring (e.g., using a continuously stirred reactor). The oil may be incubated with the PLA1 enzyme allowed to react for from 1 to 8 hours, or 2 to 7 hours, or 3 to 6 hours. Following incubation and stirring, the oil is heated to a temperature of from 70 to 85° C., such as 85° C. Reaction times may vary, depending on the PLA dosage and the level of non-hydratable phospholipids (NHPs) (e.g., Ca and Mg salts of phosphatidic acid) present. The resulting oil may be separated by settling, filtration, or the industrial practice of centrifugation.

In another embodiment, the treatment process of the present disclosure comprises contacting an oil, in particular a once refined oil, comprising a chlorophyll derivative (such as a chlorophyll substrate), with a polypeptide of the present disclosure. Typically, the temperature of the oil is from 45 to 70° C., including from 50 to 65° C. The polypeptide may be dosed in an amount of 1 to 50 U/gram of treated oil, such as from 1.4 to 50 U/gram of treated oil, or 5 to 50 U/gram of treated oil. Water may be added to the oil in an amount of from 1 to 10 w/w %, including from 2 to 8 w/w %, or 3 to 6 w/w %, or 5 w/w %. The polypeptide and water may be added as a single composition, or the polypeptide may be added separately from the water. Typically, no acid or base is added to the resulting mixture, and the process proceeds at a neutral pH (e.g., pH 7.0). Following contact with the polypeptide and water, the oil may be mixed using a shear mixer. A suitable shear mixer is the continuous shear mixer IKA Dispax Reactor. The oil is incubated with stirring for from 1.5 to 3 hours, including 2 hours. Following incubation and stirring, the oil is heated to a temperature of from 70 to 85° C. The resulting oil may be separated by settling, filtration, or the industrial practice of centrifugation.

In another embodiment a process for treating an oil comprising a chlorophyll derivative as disclosed herein may further comprise removal of pyropheophorbide, and/or pheophorbide. In one embodiment, a process for treating an oil comprising a chlorophyll derivative as disclosed herein may further comprise removal of chlorophyllide, pyropheophorbide, and/or pheophorbide. Pyropheophorbide, pheophorbide, and/or chlorophyllide can be removed during a water wash of the oil, during a chemical refining step (addition of water to remove excess soap), or by using an adsorbent of the present disclosure in the deodorization step.

In one embodiment, a process for treating an oil comprising a chlorophyll derivative, such a pyropheophytin, may further comprise treating the oil with an additional enzyme selected from the group consisting of a phospholipase, a chlorophyllase, a pheophytinase, a pyropheophytinase, and combinations thereof. A suitable phospholipase may be a phospholipase A, phospholipase B and/or phospholipase C or any suitable combination of these enzymes. Treating the oil with a phospholipase, so-called enzymatic degumming, reduces the phospholipid content in the oil, resulting in a lower atomic phosphorous content in the oil.

The present disclosure also relates to an oil (e.g., a triacylglycerol oil, vegetable oil, oil from algae, etc.) obtainable by a process as disclosed herein. An oil, which may be a triacylglycerol oil obtainable by a process as disclosed herein may comprise a polypeptide having decolorase activity, such as pyropheophytinase activity as disclosed herein.

Sequences

SEQ ID NO: 1=CHL26 polypeptide having decolorase including a pyropheophytinase activity from *Hordeum vulgare*.

MASAGDVFDHGRHGTSLARVEQAKNTRCSAASRVDADAQAQQSPPKPLLV

AAPCDAGEYPVVVFLHGYLCNNYFYSQLIQHVASHGFIVVCPQLYTVSGP

DTTSEINSAAAVIDWLAAGLSSKLAPGIRPNLAAVSISGHSRGGKVAFAL

GLGHAKTSLPLAALIAVDPVDGTGMGNQTPPPILAYKPNAIRVPAPVMVI

GTGLGELPRNALFPPCAPLGVSHAAFYDECAAPACHLVARDYGHTDMMDD

VTTGAKGLATRALCKSGGARAPMRRFVAGAMVAFLNKWVEGKPEWLDAVR

EQTVAAPVVLSAVEFRDE

SEQ ID NO: 2: Codon optimized nucleic acid sequence encoding a polypeptide having decolorase including pyropheophytinase activity from *Hordeum vulgare* CHL26 for expression in *Pseudomonas fluorescens*.
SEQ ID NO: 3; CHL25 putative chlorophyllase from *Gossypium raimondii*
SEQ ID NO: 4; CHL27 putative chlorophyllase from *Phoenix dactylifera*
SEQ ID NO: 5; CHL28 putative chlorophyllase from *Wollemia nobilis*
SEQ ID NO: 6; CHL29 putative chlorophyllase from *Cucumis sativus*
SEQ ID NO: 7; CHL30 putative chlorophyllase from *Tarenaya hassleriana*
SEQ ID NO: 8; CHL31 putative chlorophyllase from *Solanum tuberosum*
SEQ ID NO: 9; CHL32 putative chlorophyllase from *Populus trichocarpa*
SEQ ID NO: 10; CHL33 putative chlorophyllase from *Vigna radiata*
SEQ ID NO: 11; N1 Negative control, Green Fluorescent Protein (GFP)
SEQ ID NO: 12; P2, *Chlamydomonas reinhardtii* chlorophyllase having pyropheophytinase activity. SEQ ID NO: 12 is also referred to herein as ELDC94.
SEQ ID NO: 13; SpeI site and ribosome binding site
SEQ ID NO: 14; stop codon and XhoI site.

EXAMPLES

Materials and Methods
General
Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Water is Milli-Q water where nothing else is specified.
Analytical Methods:
pH—stoichiometric addition of acid and base to a water percentage that was added to the oil. 2 percent water in a 2000 grams reaction would be 40 grams, adding 2.0 grams of a 50 percent solution of citric acid, plus 1.6 mL of 4 M sodium hydroxide would yield a water solution with a pH of 4.5. The pH of the oil will always remain 7.

Soap—American Oil Chemists' Society Official Method Cc 13a-43, revised 2017.

Free Fatty Acid—American Oil Chemists' Society Official Method Ca 5a-40, revised 2017.

Color—American Oil Chemists' Society Official Method Ce 13e-92, reapproved 2017. Utilized Tintometer's PFX-950 at 5¼" cell.

Phosphorus and trace metals—American Oil Chemists' Society Official Method Ca 17-01-43, revised 2017.

Phospholipid Compositions For $^{31}$P NMR methods (also referred to as 31-P NMR), 10 µL of 10% DOL dispersion was dispersed in 1 mL of an aqueous solvent containing demineralized water with 10% deuterium oxide ($D_2O$, Cambridge Isotope Laboratories, DLM-4), 25 mg/mL deoxycholic acid (Sigma D2510), 5.84 mg/mL EDTA di Na (Titriplex III, Merck 108418), and 5.45 mg/mL TRIS base (Tris(hydroxymethyl) aminomethane, Merck 108387), of which the pH was adjusted to pH 9 using 4N KOH and to which 2 mg/mL TIP internal standard (tri-isopropylphosphate, Aldrich 554669) (accurately weighed) was added.

All samples were measured in a Bruker 400 MHz AvanceIII NMR spectrometer with a Prodigy BBO probe. The temperature of the probe head was set at 300K.

The measurement for quantification was performed with semi-quantitative parameters: 128 scans, 90° pulse, D1=5 sec. Values are reported in µmol/g of dry weight (DOL) of the sample.

Analysis of green color content by UV/Vis—The AOCS UV/Vis method is used to measure the green color content of oils. The AOCS UV/Vis method is described in Cc 13d-55, reapproved 2017.

Analysis of Chlorophyll Derivatives by HPLC-FLU

The analysis of pheophytins A and B, and pyropheophytins A and B, and their phorbides, as well as chlorophyll and chlorophyllide, was performed by HPLC using fluorescence detection, a method developed based on the work of Hwang et al J. Food Hyg. Soc. Japan Vol. 46, No. 2, 45-48, extended by fluorescence detection at λex 410 nm/λem 666 nm for the A compounds, and λex 436 nm/λem 653 nm for the B compounds.

Analysis for the Water Content of the Adsorbent

Water content, in wt %, is determined by heating the adsorbent to 1750 F until a constant weight is observed. The water content equals the mass lost divided by the original mass of the material expressed in percentage.

Sample Preparation

Oil samples were diluted in acetone, 1 g oil in 9 mL acetone, and centrifuged at 14000 rpm for 5 minutes. The clear supernatants were transferred into injection vials, and 10 µl of a sample was injected into the HPLC. As the chlorophyll levels were so low in all practical oil samples, these were not taken into account in the analysis.

Data Analysis

The peak surface areas (in arbitrary units) of the chromatograms indicate the amount of pheophytins, pyropheophytins, pheophorbides and pyropheophorbides present in the oil samples. FIGS. 2 and 3 show the peak surface areas of pheophytins, pyropheophytins, pheophorbides and pyropheophorbides in oil samples after incubation with putative chlorophyllases at pH 5 and pH 7. The sum of the peak surface area of phytines, the sum of peak surface area of phorbides and the peak surface area of the individual compounds are shown. The formation of pheophorbide and pyropheophorbide is a measure for the presence of pheophytinase activity and pyropheophytinase activity, respectively.

Enzymes

Purifine® Phospholipase C (PLC), and Purifine® PI-PLC and a fungal PLA1 were obtained from DSM.

Purifine® Phospholipase C comprises amino acids 38-282 of SEQ ID NO: 2, having the amino acid substitutions 63D, 131S and 134D disclosed in WO2005/086900

Purifine® PI-PLC comprises the mature polypeptide according to SEQ ID NO: 8 disclosed in WO2011/046812.

Fungal PLA1 comprises the mature amino acid sequence of SEQ ID NO: 1 disclosed in European application no. EP18171015.3

Equipment

The overhead mixer was an IKA RW 20 Digital with a flat blade paddle.

The centrifuge was a De Laval Gyro—Tester installed with "The Bowl Unit" for continuous separation. The centrifuge bowl was closed with the plug screws installed.

Shear mixing was accomplished with an Ultra-Turrax homogenizer SD-45 with a G450 rotor stator at 10,000 rpm.

Silica Adsorbents

Test adsorbents SP-2113, SP-2114, SP-2115, SP-2116, SP-2117, and SP-2119 were obtained from W.R. Grace & Co.-Conn. (Columbia, Md.). TRISYL® silica and TRISYL® 300 (W.R. Grace & Co.-Conn., Columbia, Md.) are commercially available. The properties of various silicas and adsorbents used in the Examples are set forth below.

| Base Silica Type | | pH | $Na_2O$ (wt % on a dry basis) | MgO (wt % on a dry basis) | Water Content (wt %) | Median Particle Size (µm) |
|---|---|---|---|---|---|---|
| SP-2113 | Hydrogel | 10.2 | 5.81 | <0.1 | 51.9 | 20 |
| SP-2114 | Hydrogel | 8.6 | <0.1 | 5.0 | 60.2 | 20.1 |
| SP-2115 | Hydrogel | 8.7 | <0.1 | 11.7 | 58.4 | 20.1 |
| SP-2116 | Acidic hydrogel | 6.1 | 2.91 | <0.1 | 53.7 | 21 |
| SP-2117 | Acidic hydrogel | 6.1 | 4.88 | <0.1 | 54.6 | 21 |
| SP-2119 | Xerogel | 9.1 | 0.10 | 5.2 | 11.7 | 19.1 |
| TriSyl® silica | Acidic hydrogel | 4.5 | <0.1 | <0.1 | 60.0 | 20.0 |
| TriSyl® 300 | Acidic hydrogel | 2.5 | <0.1 | <0.1 | 60.0 | 20.0 |
| Adsorbent A | Hydrogel | 8.9 | <0.1 | 11.7 | 5.2 | — |
| Adsorbent B | Hydrogel | 9.8 | <0.1 | 34.5 | 48.9 | 14.3 |
| Adsorbent C | Xerogel | 8.7 | 0.10 | 9.4 | 51.8 | 19.4 |
| Adsorbent D | Xerogel | 8.3 | <0.1 | 14.7 | 56.7 | 151 |

Example 1. Expression of a Putative Chlorophyllases in *Pseudomonas*

Putative chlorophyllases (CHL) as provided in the tables of FIGS. 2 and 3 were expressed in the *Pseudomonas* system obtained from Dow Global Technologies Inc. (US20050130160, US20050186666 and US20060110747). The 12 synthetic genes based on the protein sequence of the putative chlorophyllases protein sequences as shown in FIGS. 2-2A and 3 were designed by optimizing the gene codon usage for *Pseudomonas* according to the algorithm of DNA2.0 (GeneGPS® technology). For cloning purposes, the DNA sequence contain a SpeI site and ribosome binding site (ACTAGTAGGAGGTAACTAATG) (SEQ ID NO: 13) at the 5'-end and a stop codon and XhoI site (TGATGACTCGAG) (SEQ ID NO: 14) at the 3'-end.

SEQ ID NO: 2 shows the codon optimized nucleic acid sequence encoding the putative chlorophyllase SEQ ID NO:1 of *Hordeum vulgare*.

The DNA sequences were inserted in the pDOW1169 vector (Dow Global Technologies Inc., US20080058262) using SpeI and XhoI restriction enzyme cloning. The pDOW1169 vectors containing the genes encoding the CHL and PPH enzymes under control of a modified tac promotor were then introduced into *Pseudomonas fluorescens* uracil auxotrophic strain DPfl0. The transformed cells were selected after incubating on M9 minimal medium at 30° C. for 48 hours (Dow Global Technologies Inc., US20050186666) without uracil (Schneider et al. 2005).

Correct transformants were pre-cultured in 24 well pre-sterile deep well plates (Axygen, Calif., USA) containing 3 ml M9 medium. Plates were covered by a Breathseal (Greiner bio-one, Frickenhausen, Germany) and incubated at 30° C., 550 rpm and 80% humidity for 16 hours in a Microton incubator shaker (Infors AG, Bottmingen, Switzerland). From these cultures 30 µl was used to inoculate a second 24 well pre-sterile deep well plates (Axygen, Calif., USA) containing 3 ml M9 medium at 30° C., 550 rpm for 24 hours. After 8 hours, the cultures were induced with IPTG (0.3 mM final concentration). Cultures were harvested by centrifugation for 10 minutes at 2750 rpm and the supernatants removed. The cell pellets were stored overnight at −20° C. The cell pellets from the 3 ml cultures were suspended in 1 ml lysis buffer and incubated for one hour at 37° C. Lysis buffer (1 mM EDTA, 50 mM Tris, pH 8, 0.25 mg/ml lysozyme, 10 mg/ml Dnasel, 25 µM $MgSO_4$ and 0.03% triton). The lysates were centrifuged at 2750 rpm for 10 minutes and the supernatants were removed and stored.

Example 2. Determination of Pyropheophytinase Activity in Cell-Free Extracts in Crude Canola Oil Incubation Crude canola oil from North American origin, high in pheophytins and pyropheophytins was used to determine activity of the enzyme in the supernatant as produced in Example 1 on pyropheophytin A and B in the following way. Buffer (5% (v/v)) was added to oil under high-shear mixing using a Silverson mixer. For pH 5, a 20 mM citric acid buffer was used. For pH 7 a 20 mM phosphate buffer was used. A 24 wells microtiter plate was filled with 1.425 mL buffer-in-oil dispersion per well, and to each well 75 µL, 5% (v/v) cell-free extract (supernatant) produced in Example 1 was added. A list of tested samples is given in the tables of FIG. 2-2A and FIG. 3, and include a positive reference containing *Chlamydomonas reinhardtii* pyropheophytinase and negative control Green Fluorescent Protein (GFP). The microtiter plate was covered with plastic foil [Fasson S695]. Each well was stirred with an individual magnetic stirring bar. Incubations were performed at 50° C. using a KBMD microtiterplate stirrer. Samples were taken after 24 hours and analysed for the presence of pheophytins A and B, and pyropheophytins A and B, and their phorbides using HPLC-FLU as described above.

The results in FIGS. 2 and 3 show that only CHL26, a putative chlorophyllase from *Hordeum vulgare*, was able to hydrolyse all pheophytins and pyropheophytins into their respective (pyro)pheophorbides at pH 7 and pH 5.

Example 3. Incubation of Crude Canola Oil with CHL26 Versus Time

Incubation of crude canola oil with 5% cell free extract of *Hordeum vulgare* putative chlorophyllase CHL26 produced as described in Example 1, was repeated in the same way as described in Example 2 at pH7. Samples were taken after 30 min, 2 hr, 5 hr, and 24 hr. Pyropheophytin a and b, and pheophytin a and b, pyropheophorbide a and b and pheophorbide a and b were measured by HPLC as described above.

The formation of the reaction products pyropheophorbide a and b and pheophorbide a and b in Table 1 is expressed as percentage of the amount reaction product (respective phorbide molecule) after 24 hr.

Table 2 shows the relative amounts of pheophytins and pyropheophytins as a function of time after 0.5, 2 and 5 hr, expressed in percentages relatively to the value at t=0 (average of 4 measurements).

TABLE 1

Relative HPLC results for all reaction products after incubation for 0.5, 2, 5 and 24 hours at pH 7 and 50° C., in percentages relative to value after 24 hrs.

| time [hr] | Pheophorbide B (%) | Pyropheophorbide B (%) | Pheophorbide A (%) | Pyropheophorbide A (%) |
|---|---|---|---|---|
| 0.5 | 53.7 | 48.8 | 69.4 | 56.7 |
| 2 | 85.3 | 95.5 | 96.4 | 90.0 |
| 5 | 92.9 | 92.9 | 98.7 | 94.3 |
| 24 | 100.0 | 100.0 | 100.0 | 100.0 |

TABLE 2

Relative HPLC results for all phytin compounds after incubation for 0.5, 2, and 5 hours at pH 7 and 50° C., in percentages relative to value at t = 0.

| Time [hr] | Pheophytin B (%) | Pyropheophytin B (%) | Pheophytin A (%) | Pyropheophytin A (%) | Sum phytins (%) |
|---|---|---|---|---|---|
| 0 | 100.0 | 100.0 | 100.0 | 100.0 | 100.0 |
| 0.5 | 34.7 | 43.8 | 34.4 | 46.4 | 41.4 |
| 2 | 0.0 | 12.7 | 0.0 | 12.9 | 8.2 |
| 5 | 0.0 | 6.2 | 0.0 | 6.0 | 3.9 |

The results in Table 1 and 2 show that enzyme CHL26 from *Hordeum vulgare* is able to hydrolyse both pheophytin and pyropheophytin, and both the a and b compounds. After 2 hrs all pheophytins were converted (below detection limit), whereas after 5 hours almost all the pyropheophytins were converted.

Example 4. Production of CHL26 and ELDC94 by 10 L Bioreactor Fermentation

Strains and Inoculum

Of a *P. fluorescens* strain containing CHL26 (SEQ ID NO: 1) and *Chlamydomonas reinhardtii* (ELDC94; SEQ ID NO: 12) chlorophyllase as described in Example 1 a pre-culture was prepared in one-phase shake flasks with complex medium comprising yeast extract, slats and glycerol as a C-source, which was used as inoculum for the 10 L fermentations with inoculation ratio of 10% described below.

10 L Fermentations

Fermentation process was based on industrial *Pseudomonas fluorescens* fermentations (fed-batch process, sugar limited, IPTG induced). The fermentation process consisted of biomass production under exponential feed of glucose as C-source followed by production phase under IPTG induction system. After 23 hr fermentation (end of biomass production phase), IPTG was added to a final concentration of 0.125 mM in order to induce enzyme production. The feed rate of C-source (glucose) was reduced to ~70% of maximum and fermentation prolonged till 48-55 hours after inoculation.

At the end of fermentation, the broth was killed off and the enzyme release via benzoate treatment followed by pH increase of the fermentation broth.

Recovery

The intra-cellular enzyme was released by homogenization. Two passes at 750 bars, with a cooling period of 12-hours in-between was applied. Subsequently the homogenized broth was diluted with 30% water, 15% DBF (Dicalite BF), Calcium Chloride (20 g/kg original broth), and Flocculent C577 (0.1% on original broth) were added. The pH was adjusted to 8, and the material was clarified and ultra-filtrated. The UF was stabilized with 50% glycerol, and to ensure full killing of remaining bacteria MEP (methyl/ethyl paraben in a solution with propene-diol) was added, diluting the product with about 15% v/v.

Activity

Activity on p-NP Substrates

The enzyme activity was determined using the chromogenic substrate 4-nitrophenyl butyrate (Sigma N9874). Substrate stock solution: 50 mM pNP-butyrate in acetonitrile. Substrate solution: Prior to use the substrate stock solution was mixed in ratio 1:4 with 0.1 M phosphate buffer pH 7.0 also containing 0.2% BSA and 2.0% Triton X-100.

In micro titer plates, 120 µL phosphate buffer (same as above) was mixed with 15 µL substrate solution and equilibrated at 37° C. After starting the reaction by adding 15 µL sample, the OD at 405 nm was measured for 5 minutes. Also, a blank measurement was done by adding 15 µL buffer instead of sample. The slope of the linear part of the curve is used as measure for the activity. Samples were diluted such to assure that the absorbance increase after 5 minutes is less than 1.0.

Activity is calculated as follows:

$$U/mL = (\Delta Abs/min\ sample - \Delta Abs/min\ blank)/(\varepsilon_{pNP} \times 5) \times 1000 \times 150/15 \times Df/W$$

$\varepsilon_{pNP}$=Molar Extinction Coefficient of para-nitro-phenol [L·mol−1·cm−1]

5=Incubation time [min]
1000=factor from mmol to µmol
150=assay volume [µL]
=sample volume [µL]
Df=Dilution factor
W=weight of sample (g)

The activity is expressed as the amount of enzyme that liberates 1 micromol p-nitrophenol per minute under the conditions of the test. Calibration is done using a 4-nitrophenol standard solution (Sigma N7660) diluted in the above-mentioned phosphate buffer.

The activity of the final formulations of CHL26 was 1.4 U/g (0.5 w/w %), and of ELDC94 87 U/g (0.04 w/w %).

Example 5. Incubation of Crude Canola Oil with an Enzyme Having Pyropheophytinase Activity Derived from *Hordeum vulgare* (CHL26) Compared to Incubation of Crude Canola Oil with a Reference Enzyme (ELDC94) from *Chlamydomonas reinhardtii* at Various Conditions Crude canola oil was incubated with 0.5 w/w % cell free extract of *Hordeum vulgare* putative chlorophyllase CHL26 and compared to 0.04 w/w % of cell-free extract of *Chlamydomonas reinhardtii* chlorophyllase (coded ELDC94=Ref) both enzymes produced as described in Example 4. The incubation was performed on 10 g scale (10 g oil in 15 ml glass reaction vessels incubated on a hot plate aluminium reaction block with temperature control. Contents are kept vigorously stirred by magnetic bars), and now at three different temperatures (40, 50 and 60° C.), and under four regimes with varying acidity of the aqueous phase:

Acidic: 400 ppm citric acid pre-treatment;
Mildly acidic: pre-treatment with 500 ppm citric acid and 138 ppm caustic (NaOH);
Neutral: only water;
Mildly alkaline: pre-treatment with 150 ppm NaOH.

The total water level during incubation is 3% w/w, which includes enzyme formulation and pre-treatment solutions. Prior to the experiment, the acidity of the aqueous environment was assessed by diluting the pre-treated oil 1:1 with water and then the pH was measured by a pH meter. This resulted in the following pH values, indicative for the acidity of the aqueous environment in the dispersion during reaction: Acidic: pH 3.4; mildly acidic: pH 4.5; Neutral: pH 5.9 and alkalic pH 7.9.

For pre-treatment with citric acid, the citric acid (as 50% w/w solution) was added to the oil at 70° C., kept stirred at 70° C. for 30 minutes, subsequently the temperature was reduced to incubation temperature and for the mildly acid condition the NaOH (as 2.0% w/w solution) was added. In case of only NaOH addition, the oil was stirred at incubation temperature for 30 minutes.

During incubation, samples were taken after 0.5, 2, 4 and 24 hours, and analysed by HPLC-Flu as described in Example 2, now against a set of standards with known concentration. Concentrations of all substrates (chlorophyll, pheophytins, pyropheophytin—a and b) and all reaction products (chlorophyllide, pheophorbide, pyropheophorbide—a and b) were summed into total substrates and total reaction products, respectively, in mg/kg oil. All results are given in percentage of substrates and reaction products in the table below.

The results in Tables 3, 4 and 5 show that the *Hordeum vulgare* enzyme CHL26 according to SEQ ID NO: 1 has a wider application range in the presence of acid and caustic and is active at a higher temperature than the reference chlorophyllase from *Chlamydomonas reinhardtii*.

TABLE 3

Chlorophyll derivatives (wt %) in crude canola oil after incubation with the CHL26 enzyme from *Hordeum vulgare* or the reference enzyme ELDC94 from *Chlamydomonas reinhardtii* at different conditions at 40° C.

| 40° C. Condition | Time [hr] | CHL26 | | Reference | |
| --- | --- | --- | --- | --- | --- |
| | | Sum substrates | Sum reaction products | Sum substrates | Sum reaction products |
| — | 0 | 94.9 | 5.1 | 94.9 | 5.1 |
| Acidic | 0.5 | 66.5 | 33.5 | 80.6 | 19.4 |
| | 2 | 56.4 | 43.6 | 78.1 | 21.9 |
| | 4 | 51.9 | 48.1 | 75.2 | 24.8 |
| | 24 | 45.4 | 54.6 | 75.2 | 24.8 |
| Mildly acidic | 0.5 | 29.1 | 70.9 | 35.2 | 64.8 |
| | 2 | 10.0 | 90.0 | 28.7 | 71.3 |
| | 4 | 3.4 | 96.6 | 19.0 | 81.0 |
| | 24 | 0.0 | 100.0 | 15.4 | 84.6 |
| Neutral | 0.5 | 30.9 | 69.1 | 3.2 | 96.8 |
| | 2 | 10.0 | 90.0 | 1.7 | 98.3 |
| | 4 | 4.4 | 95.6 | 1.8 | 98.2 |
| | 24 | 3.0 | 97.0 | 1.7 | 98.3 |

TABLE 3-continued

Chlorophyll derivatives (wt %) in crude canola oil after
incubation with the CHL26 enzyme from *Hordeum vulgare*
or the reference enzyme ELDC94 from *Chlamydomonas reinhardtii*
at different conditions at 40° C.

| | | CHL26 | | Reference | |
|---|---|---|---|---|---|
| 40° C. Condition | Time [hr] | Sum substrates | Sum reaction products | Sum substrates | Sum reaction products |
| Mildly alkaline | 0.5 | 71.8 | 28.2 | 60.7 | 39.3 |
| | 2 | 72.5 | 27.5 | 55.2 | 44.8 |
| | 4 | 57.4 | 42.6 | 38.2 | 61.8 |
| | 24 | 14.8 | 85.2 | 32.8 | 67.2 |

TABLE 4

Chlorophyll derivatives (wt %) in crude canola oil after
incubation with the CHL26 enzyme from *Hordeum vulgare*
or the reference enzyme ELDC94 from *Chlamydomonas reinhardtii*
at different conditions at 50° C.

| | | CHL26 | | Reference | |
|---|---|---|---|---|---|
| 50° C. Condition | Time [hr] | Sum substrates | Sum reaction products | Sum substrates | Sum reaction products |
| — | 0 | 94.9 | 5.1 | 94.9 | 5.1 |
| Acidic | 0.5 | 87.7 | 12.3 | 89.9 | 10.1 |
| | 2 | 87.7 | 12.3 | 92.6 | 7.4 |
| | 4 | 88.5 | 11.5 | 93.4 | 6.6 |
| | 24 | 88.0 | 12.0 | 92.6 | 7.4 |
| Mildly acidic | 0.5 | 27.5 | 72.5 | 21.3 | 78.7 |
| | 2 | 9.7 | 90.3 | 11.7 | 88.3 |
| | 4 | 2.7 | 97.3 | 8.7 | 91.3 |
| | 24 | 2.2 | 97.8 | 2.1 | 97.9 |
| Neutral | 0.5 | 28.5 | 71.5 | 5.8 | 94.2 |
| | 2 | 13.7 | 86.3 | 3.9 | 96.1 |
| | 4 | 5.5 | 94.5 | 2.0 | 98.0 |
| | 24 | 0.6 | 99.4 | 0.6 | 99.4 |
| Mildly alkaline | 0.5 | 66.8 | 33.2 | 54.6 | 45.4 |
| | 2 | 66.4 | 33.6 | 62.1 | 37.9 |
| | 4 | 51.1 | 48.9 | 51.8 | 48.2 |
| | 24 | 10.9 | 89.1 | 41.0 | 59.0 |

TABLE 5

Chlorophyll derivatives (wt %) in crude canola oil after
incubation with the CHL26 enzyme from *Hordeum vulgare*
or the reference enzyme ELDC94 from *Chlamydomonas reinhardtii*
at different conditions at 60° C.

| | | CHL26 | | Reference | |
|---|---|---|---|---|---|
| 60° C. Condition | Time [hr] | Sum substrates | Sum reaction products | Sum substrates | Sum reaction products |
| — | 0 | 94.9 | 5.1 | 94.9 | 5.1 |
| Acidic | 0.5 | 90.5 | 9.5 | 94.7 | 5.3 |
| | 2 | 90.5 | 9.5 | 95.0 | 5.0 |
| | 4 | 90.7 | 9.3 | 92.7 | 7.3 |
| | 24 | 90.5 | 9.5 | 94.9 | 5.1 |
| Mildly acidic | 0.5 | 13.5 | 86.5 | 60.4 | 39.6 |
| | 2 | 2.5 | 97.5 | 65.7 | 34.3 |
| | 4 | 4.1 | 95.9 | 66.4 | 33.6 |
| | 24 | 2.0 | 98.0 | 68.5 | 31.5 |
| Neutral | 0.5 | 29.0 | 71.0 | 11.9 | 88.1 |
| | 2 | 10.1 | 89.9 | 7.4 | 92.6 |
| | 4 | 5.2 | 94.8 | 4.6 | 95.4 |
| | 24 | 0.0 | 100.0 | 1.5 | 98.5 |
| Mildly alkaline | 0.5 | 57.7 | 42.3 | 52.5 | 47.5 |
| | 2 | 65.1 | 34.9 | 80.4 | 19.6 |
| | 4 | 67.4 | 32.6 | 80.4 | 19.6 |
| | 24 | 33.0 | 67.0 | 93.0 | 7.0 |

Example 6. Incubation of Crude Canola Oil with an Enzyme from *Chlamydomonas* Reinhardtii (ELDC94), Followed by Treatment with Various Silicas 1,500 grams of crude canola oil was placed into a 2 liter jacketed glass beaker with an overhead mixer with a square paddle and mixed at 90 revolutions per minute (rpm). The jacket temperature was set at 65° C. 20 mL of ELDC94 *Chlamydomonas* (alga) (prepared as described in Example 4) and 100 grams of deionized water were added to the oil once the oil temperature had reached the set point. The material was shear mixed for 1 minute while covered with plastic wrap. The jacketed glass beaker was moved back to the overhead mixer and covered with plastic wrap. The material was mixed covered for 24 hours at 250 rpm.

1.5 grams of 50% (wt. %) citric acid was added to the mixing oil. The set point of the jacket was reduced to 55° C. Once the material reached 55° C., the oil was moved to the shear mixer. 1.2 mL of 4 N NaOH was added to the oil and shear mixed 30 seconds. 0.3 grams of Purifine® Phospholipase C (PLC) and 30 grams of deionized water were added. The oil was shear mixed for 1 minute while covered with plastic wrap. The jacketed glass beaker was moved back to the overhead mixer and covered again with plastic wrap. The oil was mixed for 2 hours at 55° C. at 250 rpm.

The beaker was moved back to the high shear mixer and 0.1 grams of Phospholipase A1 (PLA1) enzyme (Lecitase Ultra) was added to the oil and shear mixed 1 minute while covered with plastic wrap. The jacketed glass beaker was moved back to the overhead mixer and covered again with plastic wrap. The oil was mixed for 2 hours at 55° C. at 250 rpm. Increased the set point of the water bath to 75° C. Once the oil reached 75° C., the oil was centrifuged utilizing Gyro-Centrifuge with the bowl with holes closed. Samples of the oil were collected. The gums were discarded.

The above reaction was repeated 11 times and the oil was combined and labelled as "control".

Six 500 gram samples of the above enzyme treated canola oil "control" were added to six 1000 mL round bottom flask. The oils were heated to 80° C. and 0.25, 1.0, 2.0, 4.0, 6.0, and 8.0 grams of silica SP-2115 were mixed into the oil and a vacuum of approximately 100 mbar was added. The temperature was increased to 100° C. and mixed for 30 minutes. It was unexpected that the oil turned dark green during the adsorptive process with the test silica. In previous experiments using industrial silicas (TRISYL® (Grace Davison, Columbia, Md.), or, SORBSIL® silicas (INEOS Silicas, Joliet, Ill.) the color of the oil did not change. The vacuum was broken and the material filtered with a Buchner Funnel. The filter paper disc was a dark green color, but when using industrial silicas, the filter disc and cakes were always yellow. The filter disc and cake were a dark green color.

Two 500 gram samples of the above enzyme treated canola oil "control" from above were split and added to two 1000 mL round bottom flask with the configuration of Adsorbent procedure. The oils were heated to 80° C. and 1.0 and 2.0 grams of silica SP-2116 were mixed into the oil and a vacuum of approximately 100 mbar was added. The temperature was increased to 100° C. and mixed for 30 minutes. The color of the oil during the trial did not change from the original color. The vacuum was broken and the material filtered with a Buchner Funnel. The filter disc and cake were a yellow color.

Two 500 gram samples of the above enzyme treated canola oil "control" from above were split and added to two 1000 mL round bottom flask with the configuration of Adsorbent procedure. The oils were heated to 80° C. and 1.0 and 2.0 grams of silica SP-2117 were mixed into the oil and a vacuum of approximately 100 mbar was added. The temperature was increased to 100° C. and mixed for 30 minutes. The color of the oil during the trial did not change from the original color. The vacuum was broken and the material filtered with a Buchner Funnel. The filter disc and cake were a yellow color.

The content of the oils is set forth in Tables 6 and 7.

TABLE 6

P, Ca, Mg, and Fe content in ELDC94 treated oils following further treatment with various silicas

| | Phosphorus (ppm) | Calcium (ppm) | Magnesium (ppm) | Iron (ppm) |
|---|---|---|---|---|
| Crude Canola | 836 | 161 | 119 | 1.6 |
| Enzyme treated Control (ELDC94) | 14.2 | 11.42 | 1.99 | 0.42 |
| SP-2115 - 0.25 g | 9.34 | 6.19 | 1.19 | 0.19 |
| SP-2115 - 1 g | 9.34 | 7.32 | 1.43 | 0.25 |
| SP-2115 - 2 g | 4.52 | 3.86 | 1.17 | 0.13 |
| SP-2115 - 4 g | 3.24 | 3.26 | 0.90 | 0.14 |
| SP-2115 - 6 g | 5.24 | 4.37 | 1.53 | 0.16 |
| SP-2115 - 8 g | 1.96 | 2.12 | 0.88 | 0.05 |
| SP-2116 - 0.25 g | 9.99 | 6.81 | 1.25 | 0.21 |
| SP-2116 - 1 g | 9.43 | 7.01 | 1.42 | 0.22 |
| SP-2117 - 0.25 g | 10.06 | 7.32 | 1.31 | 0.23 |
| SP-2117 - 1 g | 9.55 | 7.81 | 1.57 | 0.16 |

TABLE 7

Content of chlorophyll derivatives in ELDC94 treated oils following further treatment with various silicas

| | Chlorophyll and Chlorophyll Derivatives | | | | | | | | |
|---|---|---|---|---|---|---|---|---|---|
| | "A" | | | | | "B" | | | |
| | CHYL (ppm) | PYN (ppm) | PPYN (ppm) | POB (ppm) | PPOB (ppm) | CHYL (ppm) | PYN (ppm) | Total (ppm) | UV/Vis (ppm) |
| Crude Canola | 0.31 | 5.48 | 11.72 | 0.06 | 0.94 | 0.56 | 0.79 | 19.86 | 53.60 |
| Control | b.d. | 0.49 | 2.79 | 1.49 | 2.95 | b.d. | 0.34 | 8.06 | 38.49 |
| SP-2115 - 0.25 g | b.d. | 0.47 | 2.73 | 1.3 | 2.95 | b.d. | 0.46 | 7.91 | 36.29 |
| SP-2115 - 1 g | b.d. | 0.31 | 1.65 | 0.98 | 1.62 | b.d. | b.d. | 4.56 | 25.65 |
| SP-2115 - 2 g | b.d. | 0.2 | 1.43 | b.d. | 0.89 | b.d. | b.d. | 2.52 | 20.36 |
| SP-2115 - 4 g | b.d. | b.d. | 0.83 | b.d. | 0.61 | b.d. | b.d. | 1.44 | 14.32 |
| SP-2115 - 6 g | b.d. | 0.39 | 0.68 | 0.32 | b.d. | b.d. | b.d. | 1.39 | 11.04 |
| SP-2115 - 8 g | b.d. | 0.34 | 0.58 | b.d. | b.d. | b.d. | b.d. | 0.92 | 8.93 |
| SP-2116 - 0.25 g | b.d. | 0.41 | 2.78 | 1.59 | 3.39 | b.d. | 0.44 | 8.61 | 39.03 |
| SP-2116 - 1 g | b.d. | 0.52 | 2.46 | 1.42 | 2.99 | b.d. | 0.39 | 7.78 | 36.51 |
| SP-2117 - 0.25 g | b.d. | 0.38 | 2.53 | 1.4 | 3.04 | b.d. | 0.34 | 7.69 | 38.66 |
| SP-2117 - 1 g | b.d. | 0.53 | 2.48 | 1.43 | 3.01 | b.d. | 0.39 | 7.84 | 36.66 |
| Control deodorized | b.d. | 0.11 | 1.02 | 1.58 | n.d. | b.d. | b.d. | 2.71 | 19.31 |
| SP-2115 - 6 g deodorized | b.d. | b.d. | b.d. | b.d. | b.d. | b.d. | b.d. | b.d. | 3.84 |

CHYL = Chlorophyll;
PYN = Pheophytin;
PPYN = Pyropheophytin;
POB = Pheophorbide;
PPOB = Pyropheophorbide
b.d. = below detection
n.d. = not determined ELDC94 *Chlamydomonas* (alga) enzyme decreases the amount of chlorophyll and chlorophyll derivates from 19.86 ppm to 8.06 ppm (53.6 to 38.49 ppm via the AOCS UV/VIS method) after 24 hours. However, it is not great enough to significantly enable the process in an industrial process. An enzyme with a greater ability to hydrolyze chlorophyll and chlorophyll derivatives is required as well as a process for greater removal of those generated derivatives.

The above data demonstrates that silica SP-2115 has the greatest capacity to remove metals, chlorophyll, and chlorophyll derivatives compared to the other two silicas. The UV/Ms method demonstrates that treatment with the low doses (i.e., 0.25 g and 1 g) of SP-2115 reduces the chlorophyll by 2.20 and 12.84 ppm, respectively, as compared to the amount of chlorophyll in the control (i.e., 38.49 ppm). In comparison, the amount of chlorophyll following treatment with the lowest dosages (i.e., 0.25 g) of SP-2116 and SP-2117 increased by 0.54 ppm and 0.17 ppm, respectively, while the amount of chlorophyll following treatment with the highest dosages (i.e., 1 g) of SP-2116 and SP 2117 decreased 1.98 ppm and 1.83 ppm, respectively, as compared to control. The HPLC test method demonstrates the same pattern of limited reduction at the highest dosage for SP-2116 and SP-2117. The data also demonstrates that the HPLC method for chlorophyll and chlorophyll derivatives needs to be improved by finding additional standards and response factors in order to bring it closer in line with the AOCS method for measuring the green color in vegetable oils. Additional work on the method has been completed and is encompassed in the following examples.

Example 7. Incubation of Solvent Extracted Crude Canola Oil with an Enzyme Having Pyropheophytinase Activity Derived from *Hordeum vulgare* (CHL26) Compared to a Reference Enzyme from *Chlamydomonas reinhardtii* (ELDC94)

A 35-pound container of solvent extracted crude canola oil was poured into large stainless-steel container and made uniform with IKA mixer.

After mixing, approximately 1.5 kg of crude canola was placed into a 2 liter jacketed glass beaker with an overhead mixer with a square paddle and mixed at 90 revolutions per minute (rpm). The jacket temperature was set at 65° C. 0.7 grams of enzyme ELDC94 (reaction 1) or 7.5 grams of CHL26 (reaction 2), produced as described in Example 4, were added to the oil together with 100 grams of deionized water once the oil temperature had reached the set point. The material was shear mixed for 1 minute while covered with plastic wrap. The jacketed glass beaker was moved back to the overhead mixer and covered with plastic wrap. The materials were incubated with the enzymes for 24 hours at 250 rpm.

1.5 grams of 50% (wt. %) citric acid was added to the mixing oil. The set point of the jacket was reduced to 55° C. Once the material reached 55° C., the oil was moved to the shear mixer. 1.2 mL of 4 N NaOH was added to the oil and shear mixed 30 seconds. 0.3 grams of Purifine® Phospholipase C (PLC) and 30 grams of deionized water were added. The oil was shear mixed for 1 minute while covered with plastic wrap. The jacketed glass beaker was moved back to the overhead mixer and covered again with plastic wrap. The oil was mixed for 2 hours at 55° C. at 250 rpm.

The beaker was moved back to the high shear mixer and 0.1 grams of a fungal phospholipase $A_1$ ($PLA_1$) enzyme was added to the oil and shear mixed 1 minute while covered with plastic wrap. The jacketed glass beaker was moved back to the overhead mixer and covered again with plastic wrap. The oil was mixed for 2 hours at 55° C. at 250 rpm. Increased the set point of the water bath to 75° C. Once the oil reached 75° C., the oil was centrifuged utilizing a Gyro-Centrifuge with the bowl with holes closed. Samples of the oil and gums were collected and analysed for the presence of P, Ca, Mg and Fe and chlorophyll derivatives (using HPLC) as described above.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined.

The results in Table 8 and FIG. 4 a) show that the CHL26 enzyme having pyropheophytinase activity according SEQ ID NO: 1 is able to reduce chlorophyll derivatives in solvent extracted crude canola oil. Chlorophyll substrates are chlorophyll, pheophytin, and pyropheophytin and chlorophyll products are chlorophyllide, pheophorbide and pyropheophorbide.

TABLE 8

Compounds (in ppm) in crude canola oil after treatment with enzymes CHL26 and the reference enzyme ELDC94

| Enzyme | P | Ca | Mg | Fe | Chlorophyll derivatives (HPLC) (ppm) | | |
|---|---|---|---|---|---|---|---|
| | | | | | Total | Substrates | Products |
| None* | 903.0 | 243.0 | 127 | 9.89 | 15.40 | 14.72 | 0.50 |
| ELDC94 | 88.5 | 80.9 | 14.6 | 1.49 | 8.39 | 0.21 | 8.18 |
| CHL26 | 82.0 | 77.3 | 14.1 | 1.58 | 9.15 | 1.26 | 7.89 |

*Starting material (crude canola oil)

The results in FIG. 4 b) show that there are still unreacted phospholipids present in the collected heavy phase, which is an indication that the phospholipase reactions were too short to come to completion.

Example 8. Incubation of Pressed Crude Canola Oil with the CHL26 Enzyme at Varying Conditions, and Treatment with Silica SP-2115

A 35-pound container of pressed crude canola oil was poured into large stainless-steel container and made uniform with IKA mixer Reaction 3—CHL26 Incubation with PLC and PI-PLC at pH 4.5 for 2 hr, Followed by a 2 hr Incubation with PLA1

About 1.5 kg of crude canola was placed into a 2 liter jacket glass beaker with an overhead mixer with a square paddle. The oil was mixed at 90 rpm. The jacket temperature was set at 70° C. 1.5 grams of 50% (wt. %) citric acid was added to the mixing oil and shear mixed 1 minute. The set point of the jacket was reduced to 60° C. Once the material reached 60° C., the oil was moved to the shear mixer. 1.2 mL of 4 N NaOH was added to the oil and shear mixed 30 seconds. 0.3 grams of Purifine PLC (LR79.14 Feb. 2018), 0.02 grams of Purifine PI-PLC, 7.5 grams of CHL26 enzyme [*Hordeum vulgare* var. *distichum* (barley, plant)], produced as described in Example 4, and 100 grams of deionized water. The material was shear mixed for 1 minute while covered with plastic wrap. The jacketed glass beaker was moved back to the overhead mixer and covered again with plastic wrap. The oil was mixed for 2 hours at 60° C. at 250 rpm.

The jacketed glass beaker was again moved to the hear mixer where 0.075 grams of $PLA_1$ (notebook, 0743B2) was added and the oil was shear mixed 1 minute. The jacketed glass beaker was moved back to the overhead and covered with plastic wrap. The oil was mixed and the reactions were allowed to continue for 2 hours at 250 rpm. Increased the set point of the water bath to 75° C. Once the oil reached 75° C., the oil was centrifuged utilizing Gyro-Centrifuge with the bowl with holes closed. Samples of the oil and gums were collected.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined.

Reaction 4—ELDC94 Incubation with PLC and PI-PLC at pH 4.5 for 2 hr, Followed by a 2 hr Incubation with $PLA_1$ The same procedure from reaction 1 above was employed for enzyme ELDC94, using 0.61 grams of the formulated enzyme solution (produced as described in Example 4).

Two 450 gram samples of the Reaction 4 enzyme treated canola oil were split and added to two 1000 mL round bottom flask with the configuration of Adsorbent procedure. The oils were heated to 80° C. and 1.0 and 2.0 grams of silica SP-2115 were mixed into the oil and a vacuum of approximately 100 mbar was added. The temperature was increased to 100° C. and mixed for 30 minutes. The oil turned dark green during the adsorptive process with the test silica. The vacuum was broken and the material filter with a Buchner Funnel. The filter disc and cake were a dark green color.

Reaction 5—CHL26 Incubation with PLC and PI-PLC at pH 4.5 for 2 hr, Followed by a 4 hr Incubation with $PLA_1$ The same procedure was followed as reaction 1, but the PLA1 reaction was allowed to react for 4 hours instead of only 2 hours.

Two 450 grams samples of the Reaction 5 enzyme treated canola oil were split and added to two 1000 mL round bottom flask with the configuration of Adsorbent procedure. The oils were heated to 80° C. and 2.0 and 3.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color Reaction 6—CHL26 Incubation with PLC and PI-PLC at pH 4.5 for 2 hr, Followed by a 4 hr Incubation with $PLA_1$ The same procedure was followed as reaction 3, except twice the amount of CHL26 (15 grams total) was added to the reaction.

Two 450 grams samples of the Reaction 6 enzyme treated canola oil were split and added to two 1000 mL round bottom flask with the configuration of Adsorbent procedure. The oils were heated to 80° C. and 1.0 and 2.0 g of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color.

Reaction 7—CHL26 Incubation with PLC and PI-PLC at Neutral pH for 2 hr, Followed by a 4 hr Incubation with $PLA_1$ The same procedure was followed as reaction 1, except no pH adjustment was made.

Reaction 8—SBO CHL26 Incubation with PLC and PI-PLC at pH 4.5 for 2 hr, Followed by a 2 hr Incubation with $PLA_1$ The same procedure as reaction 1 was followed, but the oil was a solvent extracted crude soybean oil (SBO).

Three 450 g samples of the Reaction 8 enzyme treated soybean oil were split and added to three 1000 mL round bottom flask with the configuration of Adsorbent procedure. The oils were heated to 80° C. and 0.25, 0.5 and 1.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color.

In Table 9 and FIG. 5b), the phosphorus (P), calcium (Ca), magnesium (Mg), and iron (Fe) contents of the oils and the respective gums before and after enzyme treatments according to reactions 1 to 6 are shown. At neutral pH, a higher amount of P remained in the oil as compared to reaction at pH 4.5. Table 9 also shows P, Ca, Mg, and Fe contents of the oils following treatment with silica SP-2115. This data demonstrates the silica treatment removes trace phosphorus and metals to levels sufficient to meet industrial standards for bleached oils without the use of bleaching earth. They did not lose their capacity to adsorb these impurities when the MgO was added.

The results in Table 10 and FIG. 5a) show that the CHL26 enzyme converts a higher amount of chlorophyll derivatives in crude canola oil as compared to ELDC94, when the enzymes are incubated under the same conditions (reactions 1 and 2). Table 10 also shows that contacting the enzyme treated oils with silica SP-2115 reduces the amount of both chlorophyll substrates and chlorophyll products in the oils, as compared the amount of chlorophyll substrates and products in enzyme treated oils that are not further contacted with the silica.

In the present example the CHL26 enzyme converted a higher amount of chlorophyll substrates into the respective chlorophyll products in crude canola oil under neutral conditions as compared to acid conditions (pH 4.5) (compare reaction 7 with reactions 3, 5 and 6).

The CHL26 enzymes also converts chlorophyll substrates in soybean oil into the respective chlorophyll products (reaction 8).

The results in Table 10 also show that a higher amount of chlorophyll products were found in the gums (heavy phase) when the oil was reacted with the CHL26 enzyme as compared to the reaction with the ELDC94 enzyme.

TABLE 9

Compounds in canola oil (Can) or soybean oil (SBO) after treatment with the CHL26 enzyme compared to reference enzyme ELDC94 and/or no enzyme treatment and/or after silica treatment

| Reaction | Oil | pH | Silica SP-2115 (grams) | P (ppm) | Ca (ppm) | Mg (ppm) | Fe (ppm) |
|---|---|---|---|---|---|---|---|
| None, Crude | Can | — | — | 210 | 90.5 | 36.7 | 0.90 |
| Rxn 3 - CHL26 | Can | 4.5 | — | 10.7 | 7.9 | 1.7 | 0.20 |
| Rxn 4 - ELDC94 | Can | 4.5 | — | 4.4 | 3.3 | 0.9 | 0.07 |
| Rxn 4 | | | 1 | 1.5 | 2.3 | 0.3 | 0.05 |
| Rxn 4 | | | 2 | 1.4 | 2.3 | 0.3 | 0.05 |
| None, Crude | Can | — | — | 210 | 90.5 | 36.7 | 0.90 |
| Rxn 5 - CHL26 | Can | 4.5 | — | 3.9 | 2.8 | 0.6 | 0.16 |
| Rxn 5 | | | 2 | 1.6 | 1.8 | 0.5 | 0.10 |
| Rxn 5 | | | 3 | b.d. | 0.3 | Tr | 0.02 |
| Rxn 6 - CHL26 | Can | 4.5 | — | 2.0 | 1.5 | 0.4 | 0.10 |
| Rxn 6 | | | 1 | 0.5 | 0.9 | 0.2 | 0.07 |
| Rxn 6 | | | 2 | 0.6 | 0.8 | 0.2 | 0.06 |
| Rxn 7 - CHL26 | Can | Neutral | — | 103 | 80.9 | 10.5 | 0.88 |

TABLE 9-continued

Compounds in canola oil (Can) or soybean oil (SBO) after treatment
with the CHL26 enzyme compared to reference enzyme ELDC94
and/or no enzyme treatment and/or after silica treatment

| Reaction | Oil | pH | Silica SP-2115 (grams) | P | Ca (ppm) | Mg | Fe |
|---|---|---|---|---|---|---|---|
| None, Crude | SBO | — | — | 773 | 66.2 | 64.3 | 0.76 |
| Rxn 8 - CHL26 | SBO | 4.5 | — | 5.8 | 0.5 | 0.7 | 0.04 |
|  | Rxn 8 |  | 0.25 | 0.6 | 0.2 | 0.1 | 0.03 |
|  | Rxn 8 |  | 0.5 | 0.7 | 0.2 | 0.2 | 0.03 |
|  | Rxn 8 |  | 1 | b.d. | 0.1 | 0.1 | 0.02 | b.d.—below detection
Tr—trace

TABLE 10

Chlorophyll derivatives in canola oil or soybean oil
and the separated gums after treatment with the CHL26
enzyme compared to reference enzyme ELDC94 and/or no
enzyme treatment and/or after silica treatment

| Oil | Chlorophyll derivatives in the oil (ppm) | | Chlorophyll derivatives in the gums (ppm) | |
|---|---|---|---|---|
|  | Substrates | Products | Substrates | Products |
| Crude Canola | 13.13 | 0.90 | — | — |
| Rxn 3 - CHL26, pH 4.5 | 4.19 | 7.97 | 0.06 | 6.39 |
| Rxn 4 - ELDC94, pH 4.5 | 10.28 | 2.62 | 0.18 | 3.06 |
| Rxn 4 - SP-2115, 1 g | 3.46 | b.d. | — | — |
| Rxn 4 - SP-2115, 2 g | 6.27 | 0.22 | — | — |
| Crude Canola | 13.13 | 0.90 | — | — |
| Rxn 5, CHL26, pH 4.5 | 6.85 | 5.69 | 0.30 | 2.68 |
| Rxn 5 - SP-2115, 2 g | 4.38 | 0.57 | — | — |
| Rxn 5 - SP-2115, 3 g | 0.78 | b.d. | — | — |
| Rxn 6 - CHL 26, pH 4.5 | 6.01 | 6.41 | 0.19 | 1.99 |
| Rxn 6 - SP-2115, 1 g | 3.88 | 1.22 | — | — |
| Rxn 6 - SP-2115, 2 g | 2.77 | 0.53 | — | — |
| Rxn 7 - CHL26, neutral pH | 1.26 | 10.02 | b.d. | 5.02 |
| Crude SBO | 0.31 | b.d. | — | — |
| Rxn 8 - CHL26, pH 4.5 | 0.28 | b.d. | b.d. | 0.56 |
| Rxn 8 - SP-2115, 0.25 g | 0.24 | b.d. | — | — |
| Rxn 8 - SP-2115, 0.5 g | 0.14 | b.d. | — | — |
| Rxn 8 - SP-2115, 1 g | 0.87 | b.d. | — | — | b.d.—below detection,

Example 9. Use of CHL26 Enzyme and Silica Treatment in Caustic Refining Application of Canola Oil and Soybean Oil The following experiments are an evaluation of the CHL26 in a caustic refining application where the oil has been treated with a phosphoric acid and sodium hydroxide, as occurs in industrial processes of canola and soybean oils. A "once refined" product is an oil that was treated with phosphoric acid, then treated with sodium hydroxide to convert the Free Fatty Acids (FFA) into sodium soaps that are water soluble and removed in water or "heavy" phase of the "refining" centrifuge. The oil was then washed with water (2 to 10 percent w/w) to remove the remaining soaps and residual phospholipids present in the oil. Optionally, the enzymes were evaluated after the refining centrifuge in the water washing step, but at a much lower temperature.

A five-gallon plastic pail of Once Refined Canola (OR-CAN) oil was mixed with a high shear mixer to make uniform. 2-3 kg samples were pulled for use in the experiments below.

Reaction 9—ELDC94-Comparative 2 kg of once refined canola was placed into a 4 liter glass beaker on a hot plate with overhead mixing at 90 rpm. The oil was heated to 60° C. under agitation. Once the material reached 60° C., the beaker was moved to the shear mixer. 0.8 grams of enzyme ELDC94 (produced as described in Example 4) and 100 grams of deionized water were added to the oil. The material was shear mixed for 1 minute while covered with plastic wrap to minimize water loss. The glass beaker was moved back to the overhead mixer and covered with plastic wrap. The oil was mixed for 4 hours at 60° C. at 250 rpm. The temperature was increased to 75° C. The oil was centrifuged utilizing Gyro-Centrifuge. The separated oil was collected.

The mixture of oil and heavy phase remaining in the centrifuge bowl were poured in to a 400 mL beaker where the oil was decanted off. The remaining oil and heavy phase were placed into 50 mL centrifuge tubes and spun. The oil from the decanted bowl and in the tubes was discarded and liquid heavy phases were combined. The heavy phase was a dark green.

Reaction 10—ELDC94-Comparative

Reaction 10 was a repeat of reaction 9, except 3 kg of oil was used and 2.0 grams of ELDC94 (produced as described in Example 4).

After the analyses of the oils from reaction 9 and 10, the oils were combined mixed and analysed again.

Reaction 11—CHL26

Reaction 11 was a repeat of reaction 9, except that 10.1 grams of CHL26 (produced as described in Example 4) was used instead of ELDC94. The heavy phase was a lighter green than reactions 9 and 10.

Reaction 12—CHL26

Reaction 12 was a repeat of reaction 10, except that 20 grams of CHL26 was utilized.

After analyses, the oils of reaction 11 and 12 were combined and mixed and after mixing analysed again.

Reaction 13—ELDC94-Comparative 3 kg of once refined soybean oil (ORSBO) was pulled from a caustic refining production line number 1 after the water washing centrifuge. The oil was placed into a 4 liter glass beaker and placed onto a hot plate with overhead mixing with a square mixing paddle (90 rpm). Once the material cooled 60° C., the beaker was moved to a shear mixer. 1.0 grams of ELDC94 enzyme produced as described in Example 4) and 150 grams of deionized water were added to the oil. The material was shear mixed for 1 minute while covered with a plastic wrap to minimize moisture loss. The glass beaker was moved back to the overhead mixer and again covered with a plastic wrap. The oil was mixed for 4 hours at 60° C. at 250 rpm. The temperature was increased to 75° C. and then the oil was centrifuged utilizing Gyro-Centrifuge.

Collected oil and heavy samples for further analyses.

The remaining oil and heavy phase remaining in the centrifuge bowl were poured in to a 400 mL beaker where the oil was decanted off. The remaining oil and heavy phase were placed into 50 mL centrifuge tubes and spun. The remaining oil in the tubes was discarded and liquid heavy phases were combined. The heavy phase was colorless, no discernible color pigments.

Reaction 14—CHL26

Reaction 14 was a repeat of reaction 13, except that 15 grams of CHL26 (produced as described in Example 4) was utilized instead of ELDC94.

Reaction 15—EDLC94-Comparative 3 kg grams of once refined soybean oil (ORSBO) was pulled from a caustic refining production line number 1 after the water washing centrifuge. The oil was placed into a 4 liter glass beaker and placed onto a hot plate with overhead mixing with a square mixing paddle (90 rpm). Once the material cooled 60° C., the beaker was moved to a shear mixer. 1.2 grams of ELDC94 enzyme produced as described in Example 4 and 150 grams of deionized water were added to the oil. The material was shear mixed for 1 minute while covered with a plastic wrap to minimize moisture loss. The glass beaker was moved back to the overhead mixer and again covered with a plastic wrap. The oil was mixed for 4 hours at 60° C. at 250 rpm. The temperature was increased to 75° C. and then the oil was centrifuged utilizing Gyro-Centrifuge.

Collected oil and heavy phase (gums) samples for further analyses.

The remaining oil and heavy phase remaining in the centrifuge bowl were poured in to a 400 mL beaker where the oil was decanted off. The remaining oil and heavy phase were placed into 50 mL centrifuge tubes and spun. The remaining oil in the tubes was discarded and liquid heavy phases were combined. The heavy phase was colorless, no discernible color pigments.

Reaction 16—CHL26

Reaction 16 was a repeat of reaction 15, except that 15 grams of CHL26 was utilized.

The results of reactions 9 to 16 and the results of the combined and mixed oils from reaction 9 and 10 and from reactions 11 and 12 are shown in Table 11 and FIGS. 6-6A.

The results in Table 9 and FIGS. 6-6A show that the enzyme CHL26, having pyropheophytinase converts a higher amount of chlorophyll substrates (chlorophyll, pheophytin and pyropheophytin) to its chlorophyll products (chlorophyllide, pheophorbide, pyropheophorbide) than the reference chlorophyllase enzyme ELDC94.

TABLE 11

Chlorophyll derivatives (substrates and products) in once refined canola oil (ORCAN) and once refined soybean oil (ORSBO) after caustic refining and after treatment with the CHL26 enzyme and the ELDC94 (reference) enzyme

| Enzyme reaction | Chlorophyll derivatives in oil (ppm) | |
|---|---|---|
| | Substrates | Products |
| None: ORCAN | 27.38 | b.d. |
| Rxn 9 - ELDC94 | 7.87 | 4.99 |
| Rxn 10 - ELDC94 | 19.37 | 0.42 |
| Combined 9 & 10 | 18.71 | 0.39 |
| Rxn 11 - CHL26 | 11.60 | 4.96 |
| Rxn 12 - CHL26 | n.m. | n.m. |
| Combined 11 & 12 | 12.00 | 6.19 |
| None: ORSBO | 3.85 | b.d. |
| Rxn 13 - ELDC94 | 1.09 | 0.06 |
| None: ORSBO | 3.90 | b.d. |
| Rxn 14 - CHL26 | 1.12 | 0.18 |
| None: ORSBO | 3.90 | b.d. |
| Rxn 15 - ELDC94 | 2.05 | b.d. |
| Rxn 16 - CHL26 | 1.77 | 0.07 | b.d. = below detection
n.m. = not measured

The results of Table 12 show the contents of free fatty acids (FFA), soap and phosphor and Ca, Mg, Fe, and/or chlorophyll in once refined canola oil and once refined soybean oil after enzymatic treatments described above.

TABLE 12

Composition of once refined canola oil (ORCAN), once refined soybean (ORSBO) oil after caustic refining and after treatment with the CHL26 enzyme and the ELDC94 (reference) enzyme

| | FFA (%) | Soap (ppm) | P (ppm) | Ca (ppm) | Mg (ppm) | Fe (ppm) | UV/Vis (ppb) | HPLC* (ppm) | Lovibond Color Red | Lovibond Color Yellow |
|---|---|---|---|---|---|---|---|---|---|---|
| ORCAN | 0.05 | 195 | 4.5 | 0.9 | 0.2 | 0.03 | 12047 | 27.38 | t.d. | t.d. |
| Rxn 9 - ELDC94 | 0.05 | b.d. | 0.5 | 0.7 | tr | 0.02 | 10461 | 12.86 | t.d. | t.d. |
| Rxn10 - ELDC94 | 0.07 | b.d. | 0.6 | 1.8 | tr | 0.03 | 9377 | 19.70 | t.d. | t.d. |
| Combined 9 & 10 | 0.06 | b.d. | 0.6 | 0.7 | tr | 0.07 | — | — | — | — |
| Rxn 11 - CHL26 | 0.06 | tr | 1.6 | 2.4 | 0.1 | 0.11 | 11079 | 16.56 | t.d. | t.d. |
| Rxn12 - CHL26 | 0.06 | b.d. | 1.7 | 2.9 | 0.1 | 0.07 | 11536 | n.m. | t.d. | t.d. |
| Combined 11 & 12 | 0.06 | tr | 1.7 | 2.7 | 0.1 | 0.09 | — | — | — | — |
| ORSBO | 0.12 | 20 | 0.3 | 0.2 | b.d. | b.d. | — | — | — | — |
| Rxn13 - ELDC94 | 0.10 | b.d. | 0.2 | 0.1 | b.d. | b.d. | — | — | — | — |
| ORSBO | 0.06 | 27 | 1.0 | 0.4 | tr | b.d. | — | — | — | — |
| Rxn14 - CHL26 | 0.05 | b.d. | 0.2 | 0.1 | b.d. | b.d. | — | — | — | — |
| ORSBO | 0.03 | 242 | 2.8 | 0.7 | 0.2 | tr | — | — | — | — |
| Rxn15 - ELDC94 | 0.02 | tr | 0.3 | 0.2 | b.d. | 0.1 | — | — | — | — |

TABLE 12-continued

Composition of once refined canola oil (ORCAN), once refined soybean (ORSBO) oil after caustic refining and after treatment with the CHL26 enzyme and the ELDC94 (reference) enzyme

|  | FFA (%) | Soap (ppm) | P (ppm) | Ca (ppm) | Mg (ppm) | Fe (ppm) | UV/Vis (ppb) | HPLC* (ppm) | Lovibond Color Red | Lovibond Color Yellow |
|---|---|---|---|---|---|---|---|---|---|---|
| ORSBO | 0.05 | 396 | 3.3 | 0.9 | 0.2 | b.d. | — | — | — | — |
| Rxn16 - CHL26 | 0.03 | tr | b.d. | 0.2 | b.d. | b.d. | — | — | — | — | tr = trace
b.d. = below detection
n.m. = not measured
t.d. = too dark to measure
*= HPLC was a measurement of total chlorophyll derivatives Reactions 9 and 10—Silica Treatment Oils from reactions 9 and 10 were combined and then split into three 500 gram samples of the enzyme treated ORCAN oil and added to three 1000 mL round bottom flask with the configuration of Adsorbent procedure. The oils were heated to 80° C. and 1.0, 2.0 and 3.0 grams of silica SP-2115 were mixed into the oil and a vacuum of approximately 100 mbar was added. The temperature was increased to 100° C. and mixed for 30 minutes. The oil turned dark green during the adsorptive process with the test silica. The vacuum was broken and the material filter with a Buchner Funnel. The filter paper disc was a dark green color. The oils were labeled as 9101, 9102, and 9103 respectively. Oil labeled as 9100 was the sample of reaction 9 and reaction 10 combined.

The canola oil treated, 9102 (436 grams) and 9103 (448 grams) were combined and placed in a 3 L Claisen flask. The oil was sparged with nitrogen for approximately 2 minutes. The vacuum was initiated and the nitrogen sparge was discontinued and water vapor from the steam generator was allowed to begin the deodorization process. The vacuum achieved was between 0.82-0.98 mBar during the deodorization process. The oil was heated under vacuum and water sparge (3 wt. %) to 230° C. The sparge and temperature were maintained for two hours. The heat was discontinued and the oil was allowed to cool under vacuum and water sparge. The vacuum was broken with nitrogen at approximately 100° C. and allowed to further cool to 70° C. before opening to the air. The oil was a dark greenish/grey tint. The oil was labeled as 91023-DEO.

The results in Table 13 show the contents of free fatty acids (FFA), soap, P, Ca, Mg, Fe, and chlorophyll in the combined reaction 9 and 10 oils following silica treatment as described above.

TABLE 13

Composition of once refined canola oil (ORCAN), after enzyme treatment or after enzyme and silica treatment

|  | FFA (%) | Soap (ppm) | P (ppm) | Ca (ppm) | Mg (ppm) | Fe (ppm) | UV/Vis (ppb) | HPLC* (ppm) | Lovibond Color Red | Lovibond Color Yellow |
|---|---|---|---|---|---|---|---|---|---|---|
| 9100 | 0.06 | b.d. | 0.6 | 0.7 | tr | 0.07 | n.m. | 19.10 | t.d. | t.d. |
| 9101 | n.m. | b.d. | 0.4 | 0.3 | b.d. | tr | 8273 | 19.52 | 8.0 | 70 |
| 9102 | n.m. | n.m. | 0.3 | 0.2 | b.d. | b.d. | 6848 | 17.13 | 7.6 | 70 |
| 9103 | n.m. | n.m. | b.d. | 0.1 | b.d. | b.d. | 5514 | 14.04 | 7.1 | 70 |
| 91023-Deo | 0.02 | n.m. | n.m. | n.m. | n.m. | n.m. | 1833 | 3.20 | n.m. | n.m. | tr = trace
b.d. = below detection
n.m. = not measured
t.d. = too dark to measure
*= HPLC was a measurement of total chlorophyll derivatives The results in Table 14 show the chlorophyll substrates and products in the combined reaction 9 and 10 oils following silica treatment as described above.

TABLE 14

Chlorophyll substrate and product composition in oils after enzyme and silica treatment

|  | a | | | | | a' | | b | |
|---|---|---|---|---|---|---|---|---|---|
|  | CHYL ppm | PYN ppm | PPYN ppm | POB ppm | PPOB ppm | PYN ppm | POB ppm | CHYL ppm | PYN ppm |
| 9100 | 0.19 | 5.97 | 6.85 | 0.18 | 0.15 | 1.85 | 0.05 | 0.12 | 1.64 |
| 9101 | 0.10 | 4.78 | 5.85 | 0.03 | 0.02 | 3.31 | b.d. | 0.11 | 1.32 |

TABLE 14-continued

Chlorophyll substrate and product composition in oils after enzyme and silica treatment

| | | | | | | | | | |
|---|---|---|---|---|---|---|---|---|---|
| 9102 | 0.10 | 4.50 | 4.14 | b.d. | b.d. | 3.07 | b.d. | 0.11 | 1.34 |
| 9103 | 0.10 | 3.73 | 2.73 | b.d. | b.d. | 2.65 | b.d. | 0.11 | 1.23 |
| 91023-Deo | 0.05 | 0.48 | 1.43 | b.d. | b.d. | b.d. | b.d. | 0.17 | 0.12 |

| | b | | | b' | | | | Decolorase | |
|---|---|---|---|---|---|---|---|---|---|
| | PPYN ppm | POB ppm | PPOB ppm | CHYL ppm | PYN ppm | POB ppm | Total ppm | Sub. ppm | Prod. ppm |
| 9100 | 1.58 | b.d. | b.d. | b.d. | 0.50 | b.d. | 19.10 | 18.71 | 0.39 |
| 9101 | 3.14 | b.d. | b.d. | b.d. | 0.85 | b.d. | 19.52 | 19.46 | 0.06 |
| 9102 | 2.98 | b.d. | b.d. | b.d. | 0.90 | b.d. | 17.13 | 17.13 | b.d. |
| 9103 | 2.65 | b.d. | b.d. | b.d. | 0.86 | b.d. | 14.04 | 14.04 | b.d. |
| 91023-Deo | 0.96 | b.d. | b.d. | b.d. | b.d. | b.d. | 3.20 | 3.20 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection The feed material from the combined samples from reactions using ELDC94 of 18.71 ppm as reported from the HPLC method shows a dramatic reduction in substrates following treatment with the SP-2115 to 14.04 ppm and a complete removal of the products from 0.39 ppm in the combined samples to below detection limit following treatment with SP-2115.

Reactions 11 and 12—Silica Treatment

Oils from reactions 11 and 12 were combined and then split into three 500 gram samples of the enzyme treated ORCAN oil and added to three 1000 mL round bottom flask with the configuration of Adsorbent procedure. The oils were heated to 80° C. and 1.0, 2.0 and 3.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green. The oils were labeled as 11121, 11122, and 11123 respectively. Oil labeled as 11120 was the combined sample of reaction 11 and reaction 12 oil.

The canola oil treated, 11122 (449 grams) and 11123 (451 grams) were combined and placed in a 3 L Claisen flask and assembled according to the deodorization procedure. The oil was sparged with nitrogen for approximately 2 minutes. The vacuum was initiated and the nitrogen sparge was discontinued and water vapor from the steam generator was allowed to begin the deodorization process. The vacuum achieved was between 0.28-0.56 mBar during the deodorization process. The oil was heated under vacuum and water sparge (3 wt. %) to 230° C. The sparge and temperature were maintained for two hours. The heat was discontinued and the oil was allowed to cool under vacuum and water sparge. The vacuum was broken with nitrogen at approximately 100° C. and allowed to further cool to 70° C. before opening to the air. The oil was a light greenish/grey tint. The oil was labeled as 111223-DEO.

The results in Table 15 show the contents of free fatty acids (FFA), soap, P, Ca, Mg, Fe, and chlorophyll in the combined reaction 11 and 12 oils following silica treatment as described above.

TABLE 15

Composition of once refined canola oil (ORCAN), after enzyme treatment or after enzyme and silica treatment

| | FFA | Soap | P | Ca | Mg | Fe | UV/Vis | HPLC* | Lovibond Color | |
|---|---|---|---|---|---|---|---|---|---|---|
| | (%) | (ppm) | (ppm) | (ppm) | (ppm) | (ppm) | (ppb) | (ppm) | Red | Yellow |
| 11120 | 0.06 | tr | 1.7 | 2.7 | 0.1 | 0.09 | n.m. | 18.19 | t.d. | t.d. |
| 11121 | n.m. | b.d. | 1.2 | 1.8 | tr | 0.07 | 6180 | 12.05 | 8.1 | 70 |
| 11122 | n.m. | n.m. | 0.8 | 1.1 | b.d. | 0.03 | 4267 | 9.38 | 8.9 | 70 |
| 11123 | n.m. | n.m. | 0.2 | 0.3 | b.d. | 0.01 | 3576 | 4.12 | 7.1 | 70 |
| 111223-DEO | 0.02 | n.m. | n.m. | n.m. | n.m. | n.m. | 1741 | 2.41 | n.m. | n.m. | tr = trace
b.d. = below detection
n.m. = not measured
t.d. = too dark to measure
*= HPLC was a measurement of total chlorophyll derivatives The results in Table 16 show the chlorophyll substrates and products in the combined reaction 11 and 12 oils following silica treatment as described above.

TABLE 16

Chlorophyll substrate and product composition in oils after enzyme treatment or after enzyme and silica treatment

| | a | | | | | a' | | b | |
|---|---|---|---|---|---|---|---|---|---|
| | CHYL ppm | PYN ppm | PPYN ppm | POB ppm | PPOB ppm | PYN ppm | POB ppm | CHYL ppm | PYN ppm |
| 11120 | 0.10 | 2.22 | 3.18 | 3.03 | 1.29 | 3.16 | 0.28 | 0.12 | 0.73 |
| 11121 | 0.10 | 2.40 | 2.98 | 0.43 | 0.21 | 2.49 | 0.08 | 0.12 | 0.67 |
| 11122 | 0.10 | 2.26 | 1.97 | 0.12 | 0.05 | 1.96 | 0.04 | b.d. | 0.63 |
| 11123 | 0.09 | 0.98 | 0.68 | 0.05 | 0.04 | 0.85 | b.d. | b.d. | 0.31 |
| 111223-DEO | 0.04 | 0.40 | 1.12 | b.d. | b.d. | b.d. | b.d. | 0.16 | b.d. |

| | b | | | b' | | | | Decolorase | |
|---|---|---|---|---|---|---|---|---|---|
| | PPYN ppm | POB ppm | PPOB ppm | CHYL ppm | PYN ppm | POB ppm | Total ppm | Sub. ppm | Prod. ppm |
| 11120 | 1.73 | 0.86 | 0.64 | 0.12 | 0.64 | 0.08 | 18.19 | 12.00 | 6.19 |
| 11121 | 1.72 | 0.13 | 0.10 | b.d. | 0.60 | 0.03 | 12.05 | 11.07 | 0.98 |
| 11122 | 1.57 | 0.04 | 0.06 | b.d. | 0.58 | b.d. | 9.38 | 9.06 | 0.31 |
| 11123 | 0.74 | 0.03 | 0.05 | b.d. | 0.29 | b.d. | 4.12 | 3.95 | 0.17 |
| 111223-DEO | 0.69 | b.d. | b.d. | b.d. | b.d. | b.d. | 2.41 | 2.41 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection The feed material from the combined samples from reactions using CHL26 of 18.19 ppm as reported from the HPLC method shows a dramatic reduction in substrates following treatment with the SP-2115 of from 12.00 to 3.95 ppm, and a reduction of the products from 6.19 ppm to 0.17 ppm. It is clear that SP-2115 has a capacity for both the substrates and products of the enzymatic reaction of CHL26 for their removal in an adsorptive process.

Reactions 5 and 13—Silica Treatment. Comparison of SP-2114 and SP-2115

Three 500 gram samples of the enzyme treated refined soybean oil from reaction 13 were split and added to three 1000 mL round bottom flask with the configuration of Adsorbent procedure. The oils were heated to 80° C. and 0.5, 1.0 and 2.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color. The oils were labeled as 135, 1310, and 1320 respectively. Oil labeled as 130 was the sample from reaction 13.

A 500 gram sample of the enzyme treated refined soybean oil from reaction 5 was added to a 1000 mL round bottom flask with the configuration of Adsorbent procedure. The oil was heated to 80° C. and 2.0 grams of silica SP-2114 was mixed into the oil and a vacuum of approximately 100 mbar was added. The temperature was increased to 100° C. and mixed for 30 minutes. The color change was greenish/brown in the oil was observed during the adsorption process. The vacuum was broken and the material filter with a Buchner Funnel. The filter disc and cake were light green. The sample was labeled as 132-2114.

The results in Table 17 show the contents of free fatty acids (FFA), soap, P, Ca, Mg, Fe, and chlorophyll in the reaction 5 and reaction 13 oils following silica treatment as described above.

TABLE 17

Composition of oils after enzyme treatment or after enzyme and silica treatment

| | FFA (%) | Soap (ppm) | P (ppm) | Ca (ppm) | Mg (ppm) | Fe (ppm) | UV/Vis (ppb) | HPLC* (ppm) | Lovibond Color | |
|---|---|---|---|---|---|---|---|---|---|---|
| | | | | | | | | | Red | Yellow |
| ORSBO | 0.12 | 20 | 0.3 | 0.2 | b.d. | b.d. | 331 | 3.85 | 11.1 | 70 |
| 130 | 0.10 | b.d. | 0.2 | 0.1 | b.d. | b.d. | 298 | 1.15 | 9.9 | 70 |
| 135 | b.d. | b.d. | b.d. | 0.1 | b.d. | b.d. | 138 | 1.06 | 9.1 | 70 |
| 1310 | n.m. | b.d. | b.d. | 0.1 | b.d. | b.d. | 90 | 1.05 | 9 | 70 |
| 1320 | n.m. | b.d. | b.d. | b.d. | b.d. | b.d. | 41 | 1.03 | 8.6 | 70 |
| 132-2114 | n.m. | n.m. | n.m. | n.m. | n.m. | n.m. | 104 | 1.01 | 8.3 | 70 | b.d. = below detection
n.m. = not measured
*= HPLC was a measurement of total chlorophyll derivatives The results in Table 18 show the chlorophyll substrates and products in the reaction 5 and 13 oils following silica treatment as described above.

TABLE 18

Chlorophyll substrate and product composition in oils after enzyme treatment or after enzyme and silica treatment

| | a | | | | | a' | | b | |
|---|---|---|---|---|---|---|---|---|---|
| | CHYL ppm | PYN ppm | PPYN ppm | POB ppm | PPOB ppm | PYN ppm | POB ppm | CHYL ppm | PYN ppm |
| ORSBO | 0.21 | 0.70 | 0.24 | b.d. | ND | 1.26 | b.d. | 0.28 | 0.24 |
| 130 | 0.17 | 0.31 | 0.05 | 0.03 | 0.03 | b.d. | b.d. | 0.22 | 0.11 |
| 135 | 0.17 | 0.31 | 0.04 | b.d. | b.d. | b.d. | b.d. | 0.21 | 0.11 |
| 1310 | 0.17 | 0.31 | 0.03 | b.d. | b.d. | b.d. | b.d. | 0.22 | 0.11 |
| 1320 | 0.17 | 0.31 | 0.02 | b.d. | b.d. | b.d. | b.d. | 0.22 | 0.11 |
| 132-2114 | 0.16 | 0.27 | 0.03 | b.d. | b.d. | 0.17 | b.d. | 0.22 | ND |

| | b | | | b' | | | | Decolorase | |
|---|---|---|---|---|---|---|---|---|---|
| | PPYN ppm | POB ppm | PPOB ppm | CHYL ppm | PYN ppm | POB ppm | Total ppm | Sub. ppm | Prod. ppm |
| ORSBO | 0.49 | b.d. | b.d. | b.d. | 0.43 | b.d. | 3.85 | 3.85 | b.d. |
| 130 | 0.23 | b.d. | b.d. | b.d. | b.d. | b.d. | 1.15 | 1.09 | 0.06 |
| 135 | 0.22 | b.d. | b.d. | b.d. | b.d. | b.d. | 1.06 | 1.06 | b.d. |
| 1310 | 0.22 | b.d. | b.d. | b.d. | b.d. | b.d. | 1.05 | 1.05 | b.d. |
| 1320 | 0.22 | b.d. | b.d. | b.d. | b.d. | b.d. | 1.03 | 1.03 | b.d. |
| 132-2114 | 0.16 | b.d. | b.d. | b.d. | b.d. | b.d. | 1.01 | 1.01 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection
ND = not detected In a direct comparison of SP-2114 and SP-2115, SP-2114 was not as good as SP-2115, but was able to reduce the chlorophyll from 298 ppb in the reaction 13 oil to 104 ppb, as compared to 41 ppb achieved using SP-2115, as reported from the UV/Ms method.

Reaction 14—Silica Treatment. Comparison of SP-2113, SP-2115, and SP-2119

Three 500 gram samples of the enzyme treated refined soybean oil from reaction 14 were split and added to three 1000 mL round bottom flask with the configuration of Adsorbent procedure. The oils were heated to 80° C. and 0.5, 1.0 and 2.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color. The oils were labeled as 145, 1410, and 1420 respectively. Oil labeled as 140 was the sample of reaction 14.

A 500 gram sample of the enzyme treated refined soybean oil from reaction 14 was added to a 1000 mL round bottom flask with the configuration of Adsorbent procedure. The oil was heated to 80° C. and 2.0 grams of silica SP-2113 was mixed into the oil and a vacuum of approximately 100 mbar was added. The temperature was increased to 100° C. and mixed for 30 minutes. No change in the color of the oil was observed during the adsorption process. The vacuum was broken and the material filter with a Buchner Funnel. The filter disc and cake were yellow. The sample was labeled as 142-2113.

A 500 gram sample of the enzyme treated refined soybean oil from reaction 14 was added to a 1000 mL round bottom flask with the configuration of Adsorbent procedure. The oil was heated to 80° C. and 2.0 grams of silica SP-2119 was mixed into the oil and a vacuum of approximately 100 mbar was added. The temperature was increased to 100° C. and mixed for 30 minutes. No change in the color of the oil was observed during the adsorption process. The vacuum was broken and the material filter with a Buchner Funnel. The filter disc and cake were yellow. The sample was labeled as 142-2119.

The once refined soybean oil enzyme treated and silica treated samples, 1420 (471 grams) and 1410 (461 grams) were combined and placed in a 3 L Claisen flask and assembled according the deodorization procedure. The oil was sparged with nitrogen for approximately 2 minutes. The vacuum was initiated and the nitrogen sparge was discontinued and water vapor from the steam generator was allowed to begin the deodorization process. The vacuum achieved was between 0.28-0.56 mBar during the deodorization process. The oil was heated under vacuum and water sparge (3 wt. %) to 230° C. The sparge and temperature were maintained for two hours. The heat was discontinued and the oil was allowed to cool under vacuum and water sparge. The vacuum was broken with nitrogen at approximately 100° C. and allowed to further cool to 70° C. before opening to the air. The oil was colorless with no green tint. The oil was labeled as 14101420-DEO.

The results in Table 19 show the content of free fatty acids (FFA), soap, P, Ca, Mg, Fe, and chlorophyll in the reaction 14 oil following silica treatment as described above.

TABLE 19

Composition of ORSBOs after enzyme treatment or after enzyme and silica treatment

| | FFA (%) | Soap (ppm) | P (ppm) | Ca (ppm) | Mg (ppm) | Fe (ppm) | UV/Vis (ppb) | HPLC* (ppm) | Lovibond Color Red | Lovibond Color Yellow |
|---|---|---|---|---|---|---|---|---|---|---|
| ORSBO | 0.06 | 27 | 1.0 | 0.4 | tr | b.d. | 319 | 3.90 | 9.2 | 70 |
| 140 | 0.05 | b.d. | 0.2 | 0.1 | b.d. | b.d. | 302 | 1.46 | 9.6 | 70 |
| 145 | n.m. | n.m. | b.d. | 0.1 | b.d. | b.d. | n.m. | 1.09 | n.m. | n.m. |
| 1410 | n.m. | n.m. | b.d. | 0.1 | b.d. | b.d. | 94 | 1.07 | 9.2 | 70 |
| 1420 | n.m. | n.m. | b.d. | 0.1 | b.d. | b.d. | 52 | 1.04 | 8.7 | 70 |
| 142-2113 | n.m. | n.m. | n.m. | n.m. | n.m. | n.m. | 309 | 1.13 | 8.7 | 70 |
| 142-2119 | n.m. | n.m. | n.m. | n.m. | n.m. | n.m. | 305 | 1.16 | 8.9 | 70 |
| 14101420-Deo | 0.02 | n.m. | n.m. | n.m. | n.m. | n.m. | 55 | 0.46 | 0.1 | 2.4 | b.d. = below detection
n.m. = not measured
*= HPLC was a measurement of total chlorophyll derivatives The results in Table 20 show the chlorophyll substrates and products in the reaction 14 oil following silica treatment as described above.

TABLE 20

Chlorophyll substrate and product composition in ORSBOs after enzyme treatment or after enzyme and silica treatment

| | a | | | | | a' | | b | |
|---|---|---|---|---|---|---|---|---|---|
| | CHYL ppm | PYN ppm | PPYN ppm | POB ppm | PPOB ppm | PYN ppm | POB ppm | CHYL ppm | PYN ppm |
| ORSBO | 0.22 | 0.72 | 0.25 | b.d. | b.d. | 1.27 | b.d. | 0.26 | 0.24 |
| 140 | 0.17 | 0.31 | 0.08 | 0.05 | 0.05 | b.d. | 0.03 | 0.22 | 0.11 |
| 145 | 0.17 | 0.31 | 0.05 | b.d. | b.d. | b.d. | b.d. | 0.22 | 0.11 |
| 1410 | 0.17 | 0.31 | 0.03 | b.d. | b.d. | b.d. | b.d. | 0.22 | 0.11 |
| 1420 | 0.17 | 0.31 | 0.02 | b.d. | b.d. | b.d. | b.d. | 0.22 | 0.11 |
| 142-2113 | 0.16 | 0.25 | 0.08 | b.d. | b.d. | 0.18 | b.d. | 0.22 | b.d. |
| 142-2119 | 0.16 | 0.28 | 0.08 | b.d. | b.d. | 0.18 | b.d. | 0.22 | b.d. |
| 14101420-Deo | 0.09 | b.d. | 0.02 | b.d. | b.d. | b.d. | b.d. | 0.16 | b.d. |

| | b | | | b' | | | | Decolorase | |
|---|---|---|---|---|---|---|---|---|---|
| | PPYN ppm | POB ppm | PPOB ppm | CHYL ppm | PYN ppm | POB ppm | Total ppm | Sub. ppm | Prod. ppm |
| ORSBO | 0.52 | b.d. | b.d. | b.d. | 0.43 | b.d. | 3.90 | 3.90 | b.d. |
| 140 | 0.23 | 0.03 | 0.05 | 0.11 | b.d. | b.d. | 1.46 | 1.28 | 0.18 |
| 145 | 0.23 | b.d. | b.d. | b.d. | b.d. | b.d. | 1.09 | 1.09 | b.d. |
| 1410 | 0.23 | b.d. | b.d. | b.d. | b.d. | b.d. | 1.07 | 1.07 | b.d. |
| 1420 | 0.22 | b.d. | b.d. | b.d. | b.d. | b.d. | 1.04 | 1.04 | b.d. |
| 142-2113 | 0.24 | b.d. | b.d. | b.d. | b.d. | b.d. | 1.13 | 1.13 | b.d. |
| 142-2119 | 0.24 | b.d. | b.d. | b.d. | b.d. | b.d. | 1.16 | 1.16 | b.d. |
| 14101420-Deo | 0.18 | b.d. | b.d. | b.d. | b.d. | b.d. | 0.46 | 0.46 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection Unlike samples treated with SP-2115, samples treated with SP-2113 or SP-2119 did not demonstrate any activity for the removal of chlorophyll as measured by the UV/Ms method. This method is accepted by the industry.

Reaction 15—Silica Treatment and/or Deodorization

Three 500 g samples of the enzyme treated refined soybean oil from reaction 15 were split and added to three 1000 mL round bottom flask with the configuration of Adsorbent procedure. The oils were heated to 80° C. and 0.5, 1.0 and 2.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color. The oils were labeled as 155, 1510, and 1520 respectively. Oil labeled as 150 was the sample of reaction 15.

The once refined soybean oil enzyme treated and silica treated samples, 1520 (457 grams) and 1510 (461 grams) were combined and placed in a 3 L Claisen flask and assembled according the deodorization procedure. The oil was sparged with nitrogen for approximately 2 minutes. The vacuum was initiated and the nitrogen sparge was discontinued and water vapor from the steam generator was allowed to begin the deodorization process. The vacuum achieved was between 0.57-0.97 mBar during the deodorization process. The oil was heated under vacuum and water sparge (3 wt. %) to 230° C. The sparge and temperature were maintained for two hours. The heat was discontinued and the oil was allowed to cool under vacuum and water sparge. The vacuum was broken with nitrogen at approximately 100° C. and allowed to further cool to 70° C. before opening to the air. The oil was colorless with no green tint. The oil was labeled as 15101520-DEO.

618 grams of the enzyme treated oil from reaction 15, without any adsorbent treatment, was placed in a 3 L Claisen flask and assembled according the deodorization procedure. The oil was sparged with nitrogen for approximately 2 minutes. The vacuum was initiated and the nitrogen sparge was discontinued and water vapor from the steam generator was allowed to begin the deodorization process. The vacuum achieved was between 1.15-1.40 mBar during the deodorization process. The oil was heated under vacuum and water sparge (3 wt. %) to 230° C. The sparge and temperature were maintained for two hours. The heat was discontinued and the oil was allowed to cool under vacuum and water sparge. Broke vacuum with nitrogen at 100° C. and allowed to cool to 70° C. before opening to the air. The oil was colorless without any green tint. The oil was labeled as 150-DEO.

The results in Table 21 show the contents of free fatty acids (FFA), soap, P, Ca, Mg, Fe, and chlorophyll in the reaction 15 oil following deodorization and/or silica treatment as described above.

TABLE 21

Composition of oils after enzyme treatment or after enzyme and silica treatment

|  | FFA | Soap | P | Ca | Mg | Fe | UV/Vis | HPLC* | Lovibond Color | |
| --- | --- | --- | --- | --- | --- | --- | --- | --- | --- | --- |
|  | (%) | (ppm) | (ppm) | (ppm) | (ppm) | (ppm) | (ppb) | (ppm) | Red | Yellow |
| Refined | 0.03 | 242 | 2.8 | 0.7 | 0.2 | tr | 321 | 3.90 | n.m. | n.m. |
| 150 | 0.02 | tr | 0.3 | 0.2 | b.d. | 0.1 | 282 | 2.05 | 9.3 | 70 |
| 155 | n.m. | b.d. | 0.1 | 0.2 | b.d. | b.d. | 219 | 1.94 | 8.7 | 70 |
| 1510 | n.m. | b.d. | 0.1 | 0.1 | b.d. | b.d. | 133 | 1.79 | 8.9 | 70 |
| 1520 | n.m. | b.d. | 0.1 | 0.1 | n.m. | b.d. | 33 | 1.04 | 8.4 | 70 |
| 15101520-Deo | 0.02 | n.m. | n.m. | n.m. | n.m. | n.m. | 40 | 0.82 | 0.0 | 2.1 |
| 150-Deo | 0.02 | n.m. | n.m. | n.m. | n.m. | n.m. | 176 | 0.88 | 0.3 | 3.2 | tr = trace
b.d. = below detection
n.m. = not measured
*= HPLC was a measurement of total chlorophyll derivatives The results in Table 22 show the chlorophyll substrates and products in the reaction 15 oil following deodorization and/or silica treatment as described above. The results demonstrate the need for an adsorbent to remove the final lower color.

TABLE 22

Chlorophyll substrate and product composition in oils after enzyme treatment or after enzyme and silica treatment

|  | a | | | | | a' | | b | |
| --- | --- | --- | --- | --- | --- | --- | --- | --- | --- |
|  | CHYL ppm | PYN ppm | PPYN ppm | POB ppm | PPOB ppm | PYN ppm | POB ppm | CHYL ppm | PYN ppm |
| Refined | 0.20 | 0.71 | 0.26 | b.d. | b.d. | 1.27 | b.d. | 0.27 | 0.23 |
| 150 | 0.17 | 0.33 | 0.13 | b.d. | b.d. | 0.62 | b.d. | 0.22 | 0.11 |
| 155 | 0.18 | 0.32 | 0.10 | b.d. | b.d. | 0.61 | b.d. | 0.22 | 0.11 |
| 1510 | 0.17 | 0.32 | 0.05 | b.d. | b.d. | 0.61 | b.d. | 0.22 | 0.11 |
| 1520 | 0.17 | 0.31 | 0.02 | b.d. | b.d. | b.d. | b.d. | 0.22 | 0.11 |
| 15101520-Deo | 0.10 | 0.31 | 0.03 | b.d. | b.d. | b.d. | b.d. | 0.15 | b.d. |
| 150-Deo | 0.06 | 0.31 | 0.13 | b.d. | b.d. | b.d. | b.d. | 0.13 | b.d. |

|  | b | | | b' | | | Decolorase | | |
| --- | --- | --- | --- | --- | --- | --- | --- | --- | --- |
|  | PPYN ppm | POB ppm | PPOB ppm | CHYL ppm | PYN ppm | POB ppm | Total ppm | Sub. ppm | Prod. ppm |
| Refined | 0.52 | b.d. | b.d. | b.d. | 0.43 | b.d. | 3.90 | 3.90 | b.d. |
| 150 | 0.25 | b.d. | b.d. | b.d. | 0.21 | b.d. | 2.05 | 2.05 | b.d. |
| 155 | 0.25 | b.d. | b.d. | b.d. | b.d. | b.d. | 1.79 | 1.79 | b.d. |
| 1510 | 0.25 | b.d. | b.d. | b.d. | 0.21 | b.d. | 1.94 | 1.94 | b.d. |

TABLE 22-continued

Chlorophyll substrate and product composition in oils after enzyme treatment or after enzyme and silica treatment

| 1520 | 0.22 | b.d. | b.d. | b.d. | b.d. | b.d. | 1.04 | 1.04 | b.d. |
|---|---|---|---|---|---|---|---|---|---|
| 15101520-Deo | 0.23 | b.d. | b.d. | b.d. | b.d. | b.d. | 0.82 | 0.82 | b.d. |
| 150-Deo | 0.24 | b.d. | b.d. | b.d. | b.d. | b.d. | 0.88 | 0.88 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection Reaction 16—Silica Treatment or Deodorization Three 500 gram samples of the enzyme treated refined soybean oil from reaction 16 were split and added to three 1000 mL round bottom flask with the configuration of Adsorbent procedure. The oils were heated to 80° C. and 0.5, 1.0 and 2.0 grams of silica SP-2115 were mixed into the oil and a vacuum of approximately 100 mbar was added. The temperature was increased to 100° C. and mixed for 30 minutes. The vacuum was broken and the material filter with a Buchner Funnel. The filter disc and cake were a dark green color. The oils were labeled as 165, 1610, and 1620. The oil labeled as 160 was the sample from reaction 16.

825.3 grams of the enzyme treated oil, without any adsorbent treatment, was placed in a 3 L Claisen flask and assembled according the deodorization procedure. The oil was sparged with nitrogen for approximately 2 minutes. The vacuum was initiated and the nitrogen sparge was discontinued and water vapor from the steam generator was allowed to begin the deodorization process. The vacuum achieved was between 1.15-1.40 mBar during the deodorization process. The oil was heated under vacuum and water sparge (3 wt. %) to 230° C. The sparge and temperature were maintained for two hours. The heat was discontinued and the oil was allowed to cool under vacuum and water sparge. Broke vacuum with nitrogen at 100° C. and allowed to cool to 70° C. before opening to the air. The color was expected to be greening, but was very slightly red with no greenish tint. The sample was labeled as 160-Deo.

The results in Table 23 show the contents of free fatty acids (FFA), soap, P, Ca, Mg, Fe, and chlorophyll in the reaction 16 oil following deodorization or silica treatment as described above.

TABLE 23

Composition of oils after enzyme treatment or after enzyme and silica treatment

|  | FFA (%) | Soap (ppm) | P (ppm) | Ca (ppm) | Mg (ppm) | Fe (ppm) | UV/Vis (ppb) | HPLC* (ppm) | Lovibond Color Red | Lovibond Color Yellow |
|---|---|---|---|---|---|---|---|---|---|---|
| Refined | 0.05 | 396 | 3.3 | 0.9 | 0.2 | b.d. | 321 | 2.19 | n.m. | n.m. |
| 160 | 0.03 | tr | b.d. | 0.2 | b.d. | b.d. | 301 | 1.84 | 9.1 | 70 |
| 165 | n.m. | b.d. | b.d. | 0.2 | b.d. | b.d. | 155 | 1.73 | 8.7 | 70 |
| 1610 | n.m. | n.m. | 0.1 | 0.1 | b.d. | b.d. | 79 | n.m. | 8.6 | 70 |
| 1620 | n.m. | n.m. | b.d. | 0.1 | b.d. | b.d. | 59 | 1.16 | 8.3 | 70 |
| 160-Deo | 0.02 | n.m. | n.m. | n.m. | n.m. | n.m. | 210 | 0.94 | 0.2 | 3.3 | tr = trace
b.d. = below detection
n.m. = not measured
*= HPLC was a measurement of total chlorophyll derivatives The results in Table 24 show the chlorophyll substrates and products in the reaction 16 oil following deodorization or silica treatment as described above. The results demonstrate the need for treatment with an adsorbent for final green color removal.

TABLE 24

Chlorophyll substrate and product composition in oils after enzyme treatment or after enzyme and silica treatment

|  | a | | | | | a' | | b | |
|---|---|---|---|---|---|---|---|---|---|
|  | CHYL ppm | PYN ppm | PPYN ppm | POB ppm | PPOB ppm | PYN ppm | POB ppm | CHYL ppm | PYN ppm |
| Refined | 0.21 | 0.36 | 0.12 | b.d. | b.d. | 0.63 | b.d. | 0.28 | 0.12 |
| 160 | 0.17 | 0.32 | 0.10 | 0.04 | 0.03 | 0.61 | b.d. | 0.22 | 0.11 |
| 165 | 0.17 | 0.32 | 0.06 | b.d. | b.d. | 0.61 | b.d. | 0.22 | 0.11 |

TABLE 24-continued

Chlorophyll substrate and product composition in oils after
enzyme treatment or after enzyme and silica treatment

| | | | | | | | | | |
|---|---|---|---|---|---|---|---|---|---|
| 1610 | n.m. | n.m. | n.m. | n.m. | n.m. | n.m. | n.m. | n.m. | n.m. |
| 1620 | 0.17 | 0.31 | 0.02 | b.d. | b.d. | ND | b.d. | 0.21 | 0.11 |
| 160-Deo | 0.11 | 0.31 | 0.11 | b.d. | b.d. | ND | b.d. | 0.17 | ND |

| | b | | | b' | | | | Decolorase | |
|---|---|---|---|---|---|---|---|---|---|
| | PPYN ppm | POB ppm | PPOB ppm | CHYL ppm | PYN ppm | POB ppm | Total ppm | Sub. ppm | Prod. ppm |
| Refined | 0.26 | b.d. | b.d. | b.d. | 0.21 | b.d. | 2.19 | 2.19 | b.d. |
| 160 | 0.24 | b.d. | b.d. | b.d. | b.d. | b.d. | 1.84 | 1.77 | 0.07 |
| 165 | 0.24 | b.d. | b.d. | b.d. | b.d. | b.d. | 1.73 | 1.73 | b.d. |
| 1610 | n.m. | n.m. | n.m. | n.m. | n.m. | n.m. | | | |
| 1620 | 0.23 | b.d. | b.d. | 0.11 | b.d. | b.d. | 1.16 | 1.16 | b.d. |
| 160-Deo | 0.24 | b.d. | b.d. | b.d. | b.d. | b.d. | 0.94 | 0.94 | b.d. |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection
ND = not detected Example 10. Incubation of Once Refined Canola (ORCAN) Oil with the CHL26 Enzyme, and Treatment with Silica SP-2115 or Commercial Silica or Bleaching Clay A five gallon plastic pail of Once Refined Canola (OR-CAN) oil was mixed with a high shear mixer to make uniform. Samples were pulled to use in the following experiments.

Reaction 17—CHL26

3,000 grams of the once refined canola oil was placed into a 4 liter glass beaker on a hot plate with overhead mixing. The oil was heated to 60° C. under agitation. Once the material reached 60° C., the oil was moved to the shear mixer. 15 g of the decolorase enzyme CHL26 (prepared as described in Example 4) and 150 g of deionized water were added. The material was shear mixed for 1 minute. The glass beaker was moved back to the overhead mixer and covered with plastic wrap. The oil was mixed for 4 hours at 60° C. The oil temperature was increased to 75° C., and the oil was centrifuged utilizing a Gyro-Centrifuge with a bowl with holes closed. Oil and heavy samples were collected.

The oil and heavy phase remaining in the bowl were poured into a 400 mL beaker where the oil was decanted off. The remaining oil and heavy phase were placed into 50 mL centrifuge tubes and spun. The oil remaining in the tubes was discarded and the liquid heavy phases were combined. The heavy phase was a dark green.

Reactions 18-20—CHL26

3000 grams of the once refined canola oil was placed into a 4 liter jacket glass beaker. The temperature was set at 60° C. Once the material reached 60° C., the oil was moved to a shear mixer. 15 g of the decolorase enzyme CHL26 (prepared as described in Example 4) and 150 g of deionized water were added to the hot oil. The material was shear mixed for 1 minute. The glass beaker was moved back to the overhead mixer and covered again with plastic wrap. The oil was mixed for 4 hours at 60° C. The oil temperature was increased to 75° C., and the oil was centrifuged utilizing a Gyro-Centrifuge with a bowl with holes closed. The procedure was repeated three times and the oil was collected and combined for reactions 18-20.

Reaction 17—Silica Treatment with SP-2115

500 grams of once refined canola oil from Reaction 17 was added to a 1000 mL round bottom flask with the equipment configuration of above. The oil was heated to 80° C. and 2.0 g of silica SP-2115 was mixed into the oil and a vacuum of approximately 100 mbar was added. The temperature was increased to 100° C. and mixed for 30 minutes. The vacuum was broken and the material filter with a Buchner Funnel. This experiment was repeated under the same conditions, except using 4, 6, and 8 grams of silica SP-2115.

Reactions 18-20—Silica Treatment. Comparison of SP-2115 and Commercial Silica and Bleaching Clay The once refined canola oil from the combined reactions 18-20 was treated with a commercially available silica (TriSyl® 300), a bleaching clay (Clariant 126FF), or two separate lots of SP-2115, as described below.

500 grams of once refined canola oil from the combined reactions 18-20 was added to a 1000 mL round bottom flask with the equipment configuration of above. The oil was heated to 80° C. and 2.0 g of TriSyl® 300 was mixed into the oil and a vacuum of approximately 100 mbar was added. The temperature was increased to 100° C. and the oil was mixed for 30 minutes. The vacuum was broken and the material filter with a Buchner Funnel.

500 grams of once refined canola oil from the combined reactions 18-20 was added to a 1000 mL round bottom flask with the equipment configuration of above. The oil was heated to 80° C. and 2.0 g of the bleaching clay Tonsil® supreme 126 FF (Clariant) was mixed into the oil and a vacuum of approximately 100 mbar was added. The temperature was increased to 100° C. and the oil was mixed for 30 minutes. The vacuum was broken and the material filter with a Buchner Funnel.

500 grams of once refined canola oil from combined reactions 18-20 was added to a 1000 mL round bottom flask with the equipment configuration of above. The oil was heated to 80° C. and 2.0 g of the first lot of silica SP-2115 was mixed into the oil and a vacuum of approximately 100 mbar was added. The temperature was increased to 100° C. and the oil was mixed for 30 minutes. The vacuum was broken and the material filter with a Buchner Funnel.

500 grams of once refined canola oil from combined reactions 18-20 was added to a 1000 mL round bottom flask with the equipment configuration of above. The oil was heated to 80° C. and 2.0 g of the second lot of silica SP-2115 was mixed into the oil and a vacuum of approximately 100 mbar was added. The temperature was increased to 100° C. and the oil was mixed for 30 minutes. The vacuum was broken and the material filter with a Buchner Funnel.

The results in Table 25 show the contents of free fatty acids (FFA), soap, P, Ca, Mg, Fe, and sodium (Na) in the reaction 17 oil or the combined reaction 18-20 oil following treatment with silica SP-2115, TriSyl® silica, or bleaching clay, as described above.

TABLE 25

Composition of oils after treatment with CHL26 or after treatment with CHL26 and SP-2115, TriSyl ® 300 silica, or bleaching clay

| | Oil | Soap (ppm) | FFA (%) | P (ppm) | Ca (ppm) | Mg (ppm) | Fe (ppm) | Na (ppm) |
|---|---|---|---|---|---|---|---|---|
| Once Refined | Can | 171 | 0.09 | 4.8 | 1.1 | 0.2 | 0.10 | 11.4 |
| Rxn 17 - CHL26 | Can | b.d. | 0.05 | 1.0 | 1.9 | tr | 0.05 | b.d. |
| Rxn 17 - 2.0 g SP-2115 | Can | n.m. | 0.05 | b.d. | 0.5 | b.d. | 0.02 | b.d. |
| Rxn 17 - 4.0 g SP-2115 | Can | n.m. | 0.05 | tr | 0.2 | b.d. | 0.03 | b.d. |
| Rxn 17 - 6.0 g SP-2115 | Can | n.m. | 0.04 | 0.1 | 0.2 | b.d. | 0.02 | b.d. |
| Rxn 17 -- 8.0 g SP-2115 | Can | n.m. | 0.04 | 0.3 | 0.3 | b.d. | tr | b.d. |
| Rxn 18-20 -- CHL26 | Can | b.d. | 0.05 | 0.8 | 2.0 | tr | 0.12 | b.d |
| Rxn 18-20 - 2.0 g TriSyl ®300 | Can | n.m. | 0.05 | b.d. | 0.4 | b.d. | b.d. | b.d. |
| Rxn 18-20 - 2.0 g Clariant 126FF | Can | n.m. | 0.06 | 0.2 | 0.9 | b.d. | 0.04 | b.d. |
| Rxn 18-20 - 2.0 g SP-2115 ($2^{nd}$ lot) | Can | n.m. | 0.05 | 0.8 | 0.9 | b.d. | b.d. | b.d. |
| Rxn 18-20 - 2.0 g SP-2115 ($1^{st}$ lot) | Can | n.m. | 0.05 | 0.7 | 0.6 | b.d. | 0.05 | b.d. | b.d.—below detection
tr—trace
n.m.—not measured
Once Refined means washed and dried
Can—canola The oil samples (~1 gram) were diluted in 100 ml volumetric flask with $CHCl_3$ (chloroform) and measured for chlorophyll content using the UV-Vis method looking at the peak absorbance at 670 nm. Measurements were also made using the HPLC method. The results are set forth in Table 26.

TABLE 26

Chlorophyll content of oils after treatment with CHL26 or after treatment with CHL26 and SP-2115, TriSyl ® silica, or bleaching clay

| Oil | UV/Vis (ppb) | HPLC* (ppb) |
|---|---|---|
| Starting Material (ORCO) | 32733 | 36856 |
| Rxn 17 | 30781 | 27090 |
| Rxn 17, 2 g SP-2115 | 16527 | 16722 |
| Rxn 17, 4 g SP-2115 | 14490 | 13680 |
| Rxn 17, 6 g SP-2115 | 4524 | 5652 |
| Rxn 17, 8 g SP-2115 | 3165 | 4812 |
| Rxn 18-20 Combined | 31070 | 28840 |
| Rxn 18-20, 2 g TriSyl 300 | 27881 | 25888 |
| Rxn 18-20, 2 g Clariant 126 FF | 11975 | 6551 |
| Rxn 18-20, 2 g SP-2115 ($2^{nd}$ lot) | 15462 | 13207 |
| Rxn 18-20, 2 g SP-2115 ($1^{st}$ lot) | 18487 | 15595 |

*= HPLC was a measurement of total chlorophyll derivatives

The results in Tables 27-28 show the chlorophyll substrates and products in the reaction 17 or combined reaction 18-20 oils after treatment as described above. The remaining levels are close to the level of chlorophyll substrates and products needed in an industrial process. Optimizing the reaction conditions for the decolorase enzyme will enable the elimination of bleaching earth for very green canola oils.

TABLE 27

Chlorophyll substrate and product composition in oils after treatment with CHL26
or after treatment with CHL26 and SP-2115, TriSyl ® 300, or bleaching clay

| | a | | | | | a' | | b | | | | | b' | | | |
|---|---|---|---|---|---|---|---|---|---|---|---|---|---|---|---|---|
| | CHYL ppm | PYN ppm | PPYN ppm | POB ppm | PPOB ppm | PYN ppm | POB ppm | CHYL ppm | PYN ppm | PPYN ppm | POB ppm | PPOB ppm | CHYL ppm | PYN ppm | POB ppm | Total ppm |
| Starting Material (ORCO) | 0.41 | 11.83 | 13.76 | b.d. | b.d. | 2.87 | b.d. | 0.21 | 3.21 | 3.71 | b.d. | b.d. | b.d. | 0.86 | b.d. | 36.86 |
| Rxn 17 | b.d. | 2.95 | 6.85 | 4.52 | 2.76 | 2.90 | 0.58 | 0.19 | 0.88 | 3.77 | 0.97 | 0.04 | b.d. | 0.60 | 0.09 | 27.09 |
| Rxn 17-2 g SP-2115 | 0.12 | 3.11 | 5.88 | 0.19 | b.d. | 2.16 | 0.12 | 0.21 | 0.81 | 3.52 | b.d. | b.d. | b.d. | 0.60 | b.d. | 16.72 |
| Rxn 17-4 g SP-2115 | 0.11 | 2.48 | 5.28 | 0.07 | b.d. | 1.78 | 0.06 | 0.17 | 0.60 | 2.69 | b.d. | b.d. | b.d. | 0.44 | b.d. | 13.68 |
| Rxn 17-6 g SP-2115 | 0.13 | 1.00 | 0.68 | b.d. | b.d. | 0.94 | b.d. | 0.18 | 0.43 | 1.95 | b.d. | b.d. | b.d. | 0.35 | b.d. | 5.65 |
| Rxn 17-8 g SP-2115 | 0.10 | 0.80 | 0.48 | b.d. | b.d. | 0.94 | b.d. | 0.19 | 0.37 | 1.62 | b.d. | b.d. | b.d. | 0.32 | b.d. | 4.81 |
| Rxn 18-20 combined | b.d. | 2.80 | 6.94 | 4.74 | 2.74 | 2.44 | 0.61 | 0.18 | 0.83 | 3.70 | 1.51 | 1.61 | b.d. | 0.52 | 0.19 | 28.84 |
| Rxn 18-20 - TriSyl ® 300 | b.d. | 2.33 | 7.09 | 3.53 | 1.90 | 3.42 | 0.45 | 0.18 | 0.67 | 3.66 | 0.96 | 0.88 | b.d. | 0.69 | 0.12 | 25.89 |
| Rxn 18-20 - Clariant 126 FF | b.d. | 1.58 | 1.83 | 0.57 | 0.11 | b.d. | 0.12 | 0.18 | 0.63 | 0.18 | 0.40 | 0.37 | b.d. | 0.47 | 0.10 | 6.55 |
| Rxn 18-20 - 2 g SP-2115 (2nd lot) | 0.10 | 2.74 | 5.27 | 0.15 | 0.11 | b.d. | b.d. | 0.19 | 0.74 | 3.43 | b.d. | b.d. | b.d. | 0.49 | b.d. | 13.21 |
| Rxn 18-20 - 2 g SP-2115 (1st lot) | 0.10 | 3.06 | 7.08 | 0.10 | 0.07 | b.d. | b.d. | 0.19 | 0.74 | 3.78 | b.d. | b.d. | b.d. | 0.47 | b.d. | 15.60 |

CHYL = Chlorophyll;
PYN = Pheophytin;
PPYN = Pyropheophytin;
POB = Pheophorbide;
PPOB = Pyropheophorbide;
Sub = Substrates;
Prod = Products
b.d. = below detection

TABLE 28

Chlorophyll substrate and product composition in oils
after treatment with CHL26 or after treatment with
CHL26 and SP-2115, TriSyl ® 300, or bleaching clay.

| | Decolorase | |
|---|---|---|
| | Substrates (ppm) | Products (ppm) |
| Starting Material (ORCO) | 36.86 | b.d. |
| Rxn 17 | 18.14 | 8.95 |
| Rxn 17, 2 g SP-2115 | 16.41 | 0.31 |
| Rxn 17, 4 g SP-2115 | 13.55 | 0.13 |
| Rxn 17, 6 g SP-2115 | 5.65 | b.d. |
| Rxn 17, 8 g SP-2115 | 4.81 | b.d. |
| Rxn 18-20 combined | 17.41 | 11.43 |
| Rxn 18-20, TriSyl ® 300 | 18.03 | 7.85 |
| Rxn 18-20, Clariant 126 FF | 4.87 | 1.68 |
| Rxn 18-20, 2 g SP-2115 ($2^{nd}$ lot) | 12.96 | 0.25 |
| Rxn 18-20, 2 g SP-2115 ($1^{st}$ lot) | 15.42 | 0.17 |

The commercial silica "Trisyl® 300 has a limited ability to remove the products generated in the decolorase reactions, and actually appears to convert some of the chlorophyll products back into substrates. The bleaching earth has a greater ability to remove the chlorophyll substrates found in unreacted decolorase oils, but does not remove the products of the decolorase treated oils as well as the silicas of the present disclosure.

Example 11. Preparation of Silica Adsorbents

This example describes the preparation of the adsorbents in Reactions 21-30 below:

Reaction 21—Preparation of SP-2113

600 grams of a TRISYL® silica, was dried at 60° C. to remove 173 grams of water. The silica was then impregnated with a sodium hydroxide solution containing 18.6 grams of NaOH and 81.9 grams of water. The material was blended in a Waring blender for 5 minutes.

Reaction 22—Preparation of SP-2114

600 grams of TRISYL® silica, was blended in a Waring blender for 5 minutes with 12.2 g of MgO powder.

Reaction 23—Preparation of SP-2115

600 grams of TRISYL® silica was blended in a Waring blender for 5 minutes with 31.6 g of MgO powder.

Reaction 24—Preparation of SP-2116

600 grams of TRISYL® 300 silica, was dried at 60° C. to remove 173 grams of water. The silica was then impregnated with a sodium hydroxide solution containing 11.4 grams of NaOH and 92 grams of water. The material was blended in a Waring blender for 5 minutes.

Reaction 25—Preparation of SP-2117

600 grams of TRISYL® 300 silica was dried at 60° C. to remove 173 grams of water. The silica was then impregnated with a sodium hydroxide solution containing 17.8 grams of NaOH and 92 grams of water. The material was blended in a Waring blender for 5 minutes.

Reaction 26—Preparation of SP-2119

600 grams of a silica xerogel containing less than 10 wt % water, a surface area of 707 m²/g and a median particle size of 19 microns, was blended in a Waring blender with 30 grams of MgO for 5 minutes.

Reaction 27—Preparation of Adsorbent A 4.8 grams of SP-2115 was dried in an oven at 110° C. for 3 hours.

Reaction 28—Preparation of Adsorbent B 5 grams of MgO powder and 20 grams TRISYL® silica were blended into a container, sealed, then mixed by shaking for 1 hour.

Reaction 29—Preparation of Adsorbent C 24.5 grams of a silica xerogel containing less than 10 wt % water, and having a surface area of 707 m²/g and a median particle size of 19 microns, was impregnated with 23.6 grams of DI water then added to a container containing 2.5 grams of MgO powder. The contents were sealed and mixed by shaking for 1 hour.

Reaction 30—Preparation of Adsorbent D 264 grams of silica xerogel with 4 wt % water, a surface area of 330 m²/g, and a particle size between 88 and 210 microns was impregnated with 303 grams of DI water. The material was divided into six different containers, each containing 6 grams of MgO powder. Each container was mixed by shaking for 1 hour, then the contents were all combined into a larger container and blended by shaking for 1 hour.

Example 12. Enzymatic and Adsorbent Treatment of Oils

Adsorbents prepared in Example 11 were used to further treat two batches of oil previously subjected to decolorase treatment (i.e., oil 11120, prepared as described in Example 9).

Reaction 31—Treatment of Decolorase Treated Oil with Adsorbent A 100 grams of enzymatically treated oil 11120 was heated to 80° C. then 0.21 grams of Adsorbent A was mixed into the oil. A 100 mbar vacuum was applied then the temperature was set to 100° C. and mixed for 30 minutes. The vacuum was broken and the material was filtered with a Buchner Funnel. The filter disc and cake were dark green.

Reaction 32—Treatment of Decolorase Treated Oil with Adsorbent B 100 grams of enzymatically treated oil 11120 was heated to 80° C. then 0.4 grams of Adsorbent B was mixed into the oil. A 100 mbar vacuum was applied then the temperature was set to 100° C. and mixed for 30 minutes. The vacuum was broken and the material was filtered with a Buchner Funnel. The filter disc and cake were dark green.

Reaction 33—Treatment of Decolorase Treated Oil with Adsorbent C 100 grams of enzymatically treated oil 11120 was heated to 80° C. then 0.4 grams of Adsorbent C was mixed into the oil. A 100 mbar vacuum was applied then the temperature was set to 100° C. and mixed for 30 minutes. The vacuum was broken and the material was filtered with a Buchner Funnel. The filter disc and cake were dark green.

Reaction 34—Treatment of Decolorase Treated Oil with Adsorbent D 100 grams of enzymatically treated oil 11120 was heated to 80° C. then 0.4 grams of Adsorbent D was mixed into the oil. A 100 mbar vacuum was applied then the temperature was set to 100° C. and mixed for 30 minutes. The vacuum was broken and the material was filtered with a Buchner Funnel. The filter disc and cake were dark green.

Reaction 35—Treatment of Decolorase Treated Oil with TRISYL® Silica 100 grams of enzymatically treated oil 11120 was heated to 80° C. then 0.4 grams of TRISYL® silica was mixed into the oil. A 100 mbar vacuum was applied then the temperature was set to 100° C. and mixed for 30 minutes. The vacuum was broken and the material was filtered with a Buchner Funnel. The filter disc and cake were green.

Reaction 36—Treatment of Decolorase Treated Oil with TRISYL® 300 Silica 100 grams of enzymatically treated oil 11120 was heated to 80° C. then 0.4 grams of TRISYL® 300 silica was mixed into the oil. A 100 mbar vacuum was applied then the temperature was set to 100° C. and mixed for 30 minutes. The vacuum was broken and the material was filtered with a Buchner Funnel. The filter disc and cake were yellow.

The green color concentrations from the oils produced in Reactions 31-36 were determined using the AOCS UV/Ms method. The results are set forth in Table 29.

TABLE 29

Green color of decolorase treated oil after further treatment with various adsorbents.

| Reaction | | Green color (ppm) |
|---|---|---|
| | First batch of oil 11120 | 11.4 |
| 31 | 0.2% of Adsorbent A | 6.5 |
| 32 | 0.4% of Adsorbent B | 5.7 |
| 33 | 0.4% of Adsorbent C | 5.6 |
| 34 | 0.4% of Adsorbent D | 7.0 |
| | Second batch of oil 11120 | 18.9 |
| 35 | 0.4% of TRISYL ® silica | 18.6 |
| 36 | 0.4% TRISYL ®300 silica | 18.8 |

What is claimed is:

1. A process for treating an oil comprising a chlorophyll substrate, the process comprising:
   contacting the oil with a polypeptide having decolorase activity or a composition comprising the polypeptide to produce a decolorase-treated oil, and
   contacting the decolorase-treated oil with an adsorbent comprising a silica treated with an alkaline earth metal oxide;
   wherein the adsorbent has a pH of about 7 or greater, and comprises about 0.1 wt % or greater of MgO, on a dry basis, and has a water content of from about 30 to about 75 wt. %.

2. The process of claim 1, wherein the adsorbent has a pH of from about 7 to about 10, and comprises from about 1 to about 40 wt % of MgO, on a dry basis.

3. The process of claim 2, wherein the adsorbent comprises from about 2.5 to about 15 wt % of MgO, on a dry basis.

4. The process of claim 1, wherein the silica is an amorphous, porous silica.

5. The process of claim 1, wherein the adsorbent has a molar ratio of MgO to $SiO_2$ of 1:3.8 to 1:26.

6. The process of claim 1, wherein the adsorbent has a pH of from about 8.0 to about 9.5.

7. The process of claim 1, wherein the adsorbent has a water content of from about 58 to about 65 wt %.

8. The process of claim 1, wherein the adsorbent has a median particle size of from about 0.1 to about 2,000 microns.

9. The process of claim 1, wherein the adsorbent has a surface area of from about 50 to about 800 $m^2/g$.

10. The process of claim 1, wherein the adsorbent has a pore volume from about 0.7 to about 2.0 cc/g.

11. The process of claim 1, wherein the decolorase-treated oil is contacted with the adsorbent in an amount of about 10 wt % or less based on the weight of the oil.

12. The process of claim 1, wherein the decolorase-treated oil is contacted with the adsorbent in an amount of from about 0.1 wt % to about 1 wt % based on the weight of the decolorase-treated oil.

13. The process of claim 1, wherein the decolorase-treated oil is contacted with the adsorbent at a temperature of from about 60° C. to less than about 100° C.

14. The process of claim 1, wherein the decolorase-treated oil is contacted with the adsorbent under vacuum at a temperature of from about 70° C. to about 130° C.

15. The process of claim 1, wherein the decolorase-treated oil is contacted with the adsorbent under vacuum of about 100 mbar at a temperature of about 100° C.

16. The process of claim 1, wherein the decolorase-treated oil is contacted with the adsorbent for from about 5 to about 240 minutes.

17. The process of claim 1, further comprising removing the adsorbent from the decolorase-treated oil by filtration.

18. The process of claim 1, wherein the oil comprises a triacylglycerol-based oil selected from the group consisting of canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, sesame oil, soybean oil, sunflower seed oil, tall oil, tsubaki oil, vegetable oil, and an oil from algae.

19. The process of claim 1, wherein the oil comprises an oil from algae.

20. The process of claim 1, wherein the oil comprises an oil selected from the group consisting of a crude non-degummed oil, a degummed oil, a caustic refined oil, a caustic refined and water washed oil, or a water degummed oil.

21. The process of claim 1, wherein the polypeptide is selected from the group consisting of:
   a. a polypeptide that has at least 80%, 85%, 86%, 87%, 88%, 89%, 90%, 91%, 92%, 93%, 94%, 95%, 96%, 97%, 98% or at least 99%, or 100% identity to amino acids 1 to 318 of SEQ ID NO: 1; and,
   b. a polypeptide encoded by a nucleic acid sequence that has at least 80%, 85%, 86%, 87%, 88%, 89%, 90%, 91%, 92%, 93%, 94%, 95%, 96%, 97%, 98% or at least 99%, or 100% identity to the nucleic acid sequence of SEQ ID NO: 2.

22. The process of claim 1, wherein the polypeptide has chlorophyllase activity, pheophytinase activity, pyropheophytinase activity, or combinations thereof.

23. The process of claim 1, further comprising treating the oil or the decolorase-treated oil with an additional enzyme selected from the group consisting of a phospholipase, a pheophytinase, a pyropheophytinase, a pheophorbidase, a chlorophyllase, and combinations thereof.

24. A process for treating an oil comprising a chlorophyll derivative, the process comprising contacting the oil with an adsorbent comprising a silica treated with an alkaline earth metal oxide, wherein the adsorbent has a pH of about 7 or greater, and comprises about 0.1 wt % or greater of MgO, on a dry basis, and has a water content of from about 30 to about 75 wt. %.

25. The process of claim 24, wherein the adsorbent has a pH of from about 7 to about 10, and comprises from about 1 to about 40 wt % of MgO, on a dry basis.

26. The process of claim 25, wherein the adsorbent comprises from about 2.5 to about 15 wt % of MgO, on a dry basis.

27. The process of claim 24, wherein the adsorbent has a molar ratio of MgO to $SiO_2$ of 1:3.8 to 1:26.

28. The process of claim 24, wherein the adsorbent has a pH of from about 7.0 to about 10.

29. The process of claim 24, wherein the adsorbent has a water content of from about 40 to about 70 wt %.

30. The process of claim 24, wherein the adsorbent has a median particle size of from about 0.1 to about 2,000 microns.

31. The process of claim 24, wherein the adsorbent has a surface area of from about 50 to about 800 $m^2/g$.

32. The process of claim 24, wherein the oil is contacted with the adsorbent in an amount of about 10 wt % or less based on the weight of the oil.

33. The process of claim 24, wherein the oil is contacted with the adsorbent at a temperature of less than about 100° C.

34. The process of claim 24, wherein the oil is contacted with the adsorbent under vacuum at a temperature of less than about 110° C.

35. A process for treating an oil comprising pyropheophytin comprising:
   contacting the oil with a polypeptide having pyropheophytinase activity, or a composition comprising the polypeptide, wherein pyropheophytin is converted into pyropheophorbide, and optionally wherein pheophytin is converted into pheophorbide to produce a pyropheophytinase-treated oil, and
   contacting the pyropheophytinase-treated oil with an adsorbent comprising a silica treated with an alkaline earth metal oxide;
   wherein the adsorbent has a pH of about 7 or greater, and comprises about 0.1 wt % or greater of MgO on a dry basis, and has a water content of from about 30 to about 75 wt. %.

36. The process of claim 35, wherein the adsorbent has a pH of from about 7 to about 10, and comprises from about 2.5 to about 15 wt. % MgO, on a dry basis.

37. The process of claim 35, wherein the polypeptide is selected from the group consisting of:
   a. a polypeptide which has at least 80%, 85%, 86%, 87%, 88%, 89%, 90%, 91%, 92%, 93%, 94%, 95%, 96%, 97%, 98% or at least 99%, or 100% identity to amino acids 1 to 318 of SEQ ID NO: 1; and,
   b. a polypeptide encoded by a nucleic acid sequence that has at least 80%, 85%, 86%, 87%, 88%, 89%, 90%, 91%, 92%, 93%, 94%, 95%, 96%, 97%, 98% or at least 99%, or 100% identity to the nucleic acid sequence of SEQ ID NO: 2.

38. A process for treating an oil comprising a chlorophyll derivative, the process comprising:
   contacting the oil with a polypeptide having decolorase activity or a composition comprising the polypeptide to produce a decolorase-treated oil, and
   contacting the decolorase-treated oil with an adsorbent comprising an amorphous, porous silica treated with an alkaline earth metal oxide;
   wherein the adsorbent has a pH of about 7 or greater, and comprises about 0.1 wt. % or greater of MgO, on a dry basis, and has a water content of from about 30 to about 75 wt. %; and
   wherein the treatment reduces the total concentration of chlorophyll derivatives in the decolorase-treated oil by at least 5% by weight, compared to the total concentration of chlorophyll derivatives in the decolorase-treated oil prior to contact with the adsorbent.

39. The process of claim 38, wherein the adsorbent has a pH of from about 7 to about 10, and comprises from about 1 to about 40 wt. % MgO, on a dry basis.

40. The process of claim 39 wherein the adsorbent comprises from about 2.5 to about 15 wt. % MgO, on a dry basis.

* * * * *

SEQUENCE LISTING

<160> NUMBER OF SEQ ID NOS: 14

<210> SEQ ID NO 1
<211> LENGTH: 318
<212> TYPE: PRT
<213> ORGANISM: Hordeum vulgare
<220> FEATURE:
<221> NAME/KEY: misc_feature
<223> OTHER INFORMATION: CHL26 putative chlorophyllase

<400> SEQUENCE: 1

Met Ala Ser Ala Gly Asp Val Phe Asp His Gly Arg His Gly Thr Ser
1               5                   10                  15

| | | | | | | | | | | | |
|---|---|---|---|---|---|---|---|---|---|---|---|
|Leu|Ala|Arg|Val|Glu|Gln|Ala|Lys|Asn|Thr|Arg|Cys|Ser|Ala|Ala|Ser|
| | |20| | | |25| | | |30| |

Arg Val Asp Ala Asp Ala Gln Ala Gln Gln Ser Pro Pro Lys Pro Leu
    35                  40                  45

Leu Val Ala Ala Pro Cys Asp Ala Gly Glu Tyr Pro Val Val Phe
50                55                  60

Leu His Gly Tyr Leu Cys Asn Asn Tyr Phe Tyr Ser Gln Leu Ile Gln
65                70                75            80

His Val Ala Ser His Gly Phe Ile Val Val Cys Pro Gln Leu Tyr Thr
             85                  90              95

Val Ser Gly Pro Asp Thr Thr Ser Glu Ile Asn Ser Ala Ala Ala Val
          100                105            110

Ile Asp Trp Leu Ala Ala Gly Leu Ser Ser Lys Leu Ala Pro Gly Ile
       115                120            125

Arg Pro Asn Leu Ala Ala Val Ser Ile Ser Gly His Ser Arg Gly Gly
       130                135            140

Lys Val Ala Phe Ala Leu Gly Leu Gly His Ala Lys Thr Ser Leu Pro
145                150                155            160

Leu Ala Ala Leu Ile Ala Val Asp Pro Val Asp Gly Thr Gly Met Gly
             165                170            175

Asn Gln Thr Pro Pro Ile Leu Ala Tyr Lys Pro Asn Ala Ile Arg
          180                185            190

Val Pro Ala Pro Val Met Val Ile Gly Thr Gly Leu Gly Glu Leu Pro
       195                200            205

Arg Asn Ala Leu Phe Pro Pro Cys Ala Pro Leu Gly Val Ser His Ala
       210                215            220

Ala Phe Tyr Asp Glu Cys Ala Ala Pro Ala Cys His Leu Val Ala Arg
225                230                235            240

Asp Tyr Gly His Thr Asp Met Met Asp Asp Val Thr Thr Gly Ala Lys
             245                250            255

Gly Leu Ala Thr Arg Ala Leu Cys Lys Ser Gly Gly Ala Arg Ala Pro
       260                265            270

Met Arg Arg Phe Val Ala Gly Ala Met Val Ala Phe Leu Asn Lys Trp
       275                280            285

Val Glu Gly Lys Pro Glu Trp Leu Asp Ala Val Arg Glu Gln Thr Val
       290                295            300

Ala Ala Pro Val Val Leu Ser Ala Val Glu Phe Arg Asp Glu
305                310                315

<210> SEQ ID NO 2
<211> LENGTH: 957
<212> TYPE: DNA
<213> ORGANISM: Artificial Sequence
<220> FEATURE:
<223> OTHER INFORMATION: Codon optimized nucleic acid sequence encoding
    a putative chlorophyllase from Hordeum vulgare CHL26
<220> FEATURE:
<221> NAME/KEY: misc_feature
<223> OTHER INFORMATION: Codon optimized nucleic acid sequence encoding
    a putative chlorophyllase from Hordeum vulgare CHL26

<400> SEQUENCE: 2
atggcatcag caggggacgt atttgatcat ggacggcacg gaaccagttt ggcgagggta    60
gaacaagcga agaacacccg ctgtagcgca gcgtcccgcg tggatgcgga cgcccaggct  120
cagcagtcgc cgcccaaacc cctcctggtt gcagccccat cgacgcaggc gaataccccg  180
gtggtcgtat tccttcacgg ctacttgtgc aacaattact tctactcgca gctgatccag  240

```
catgtcgcga gccacggctt cattgtagtg tgcccgcagc tgtataccgt gtctggtccg      300
gatacaacca gtgaaattaa tagcgccgct gccgtcatcg actggctcgc ggcaggactg      360
tcgtccaagc tggccccagg catccgtccg aacctggccg ccgtgagcat cagcggccac      420
tcacgcggtg gcaaggtggc ctttgccctg gtctgggggc atgccaagac cagcttgccg      480
ctggctgccc tgattgccgt ggatccagtc gacggcaccg ggatgggcaa ccaaactccc      540
cctccgatcc tggcctataa gccgaacgcc attcgggtcc ctgctcccgt gatggtgatc      600
ggcacaggac tgggcgaact gcctcgcaac gcgctgtttc accttgcgc cccttgggt       660
gtgtcgcacg ccgcgttcta cgatgagtgt gccgcacccg catgccacct ggttgcccgc      720
gactatggcc acaccgacat gatggatgac gtaacaaccg gcgccaaagg cctggcaacc      780
cgtgcgctgt gcaagagcgg tggggcaaga gccccgatgc gccgttttgt cgccggcgct      840
atggtggcgt tcctgaataa gtgggtggag ggcaagccgg aatggttgga cgccgtgcgc      900
gaacagaccg tggctgcacc ggtggtcctg tccgccgtag agtttcgcga tgagtaa          957
```

```
<210> SEQ ID NO 3
<211> LENGTH: 309
<212> TYPE: PRT
<213> ORGANISM: Gossypium raimondii
<220> FEATURE:
<221> NAME/KEY: misc_feature
<223> OTHER INFORMATION: CHL25 putative chlorophyllase

<400> SEQUENCE: 3
```

Met Ser Ala Pro Thr Ser Leu Ala Thr Asn Val Phe Gly Phe Gly Ser
1               5                   10                  15

Tyr Thr Thr Met Leu Gln Lys Val Glu Ser Val Thr Thr Ser Ser Met
            20                  25                  30

Pro Val Pro Pro Lys Ser Leu Leu Ile Ala Thr Pro Ser Glu Ala
        35                  40                  45

Gly Glu Phe Pro Leu Leu Ile Phe Leu His Gly Tyr Leu Leu Tyr Asn
    50                  55                  60

Ser Phe Tyr Ser Gln Leu Leu Gln His Val Ala Ser His Gly Phe Ile
65                  70                  75                  80

Val Ile Ala Pro Gln Leu Tyr Ile Val Ala Gly Pro Asp Thr Thr Asp
                85                  90                  95

Glu Ile Lys Ser Thr Ala Ala Ile Thr Asn Trp Leu Ser Lys Gly Val
            100                 105                 110

Leu Gln Gly Leu Leu Pro Pro Tyr Val Arg Pro Asn Leu Ser Lys Leu
        115                 120                 125

Ala Leu Ala Gly His Ser Arg Gly Gly Lys Val Ala Phe Ala Leu Ala
    130                 135                 140

Leu Gln Lys Thr Met Thr Lys Leu Lys Phe Ser Thr Leu Ile Gly Ile
145                 150                 155                 160

Asp Pro Val Asp Gly Met Asp Lys Gly Lys Gln Thr Pro Pro Val
                165                 170                 175

Leu Thr Tyr Ile Pro His Ser Phe Asp Leu Asp Met Ala Val Met Val
            180                 185                 190

Ile Gly Ser Gly Leu Gly Glu Val Lys Arg Asn Pro Leu Phe Pro Pro
        195                 200                 205

Cys Ala Pro Lys Gly Val Asn His Glu Asp Phe Phe Lys Glu Cys Arg
    210                 215                 220

Lys Pro Ala Cys His Ile Val Ala Lys Asp Tyr Gly His Leu Asp Met

Leu Asp Asp Glu Thr Asn Gly Phe Arg Gly Arg Ser Ser Tyr Cys Leu
                245                 250                 255

Cys Lys Asn Gly Glu Ala Arg Glu Pro Met Arg Arg Phe Val Gly Gly
            260                 265                 270

Val Val Val Ala Ser Met Lys Ala Tyr Leu Asn Gly Asp Asn Thr Asp
        275                 280                 285

Leu Ile Ala Ile Lys Gly His Glu Ala Ala Pro Val Glu Leu Lys Thr
    290                 295                 300

Ile Glu Phe Leu Val
305

<210> SEQ ID NO 4
<211> LENGTH: 306
<212> TYPE: PRT
<213> ORGANISM: Phoenix dactylifera
<220> FEATURE:
<221> NAME/KEY: misc_feature
<223> OTHER INFORMATION: CHL27 putative chlorophyllase

<400> SEQUENCE: 4

Met Ala Ser Val Ile Ile Asn Lys Pro Ser Ala Thr Ala Ala Ser Val
1               5                   10                  15

Phe Asp Tyr Gly Lys Leu His Val Asp Thr Ile Pro Ala Lys Gln Ser
            20                  25                  30

Asp Glu Ser Ser Pro Pro Lys Asp Ile Leu Val Val Cys Pro Lys Val
        35                  40                  45

Ala Gly Ser Tyr Thr Val Val Leu Phe Ile Gln Gly Tyr Leu Leu Ser
    50                  55                  60

Asn Ala Tyr Tyr Thr Gln Leu Leu Gln His Val Ala Ser His Gly Phe
65                  70                  75                  80

Ile Leu Ile Ala Pro Gln Cys Ile Val Val Ser Pro Tyr Ser Glu Glu
                85                  90                  95

Asp Ile Thr Ser Ala Ala Ala Val Thr Asn Trp Leu Ser Asp Gly Leu
            100                 105                 110

Gln Ser Val Leu Pro Thr Gly Val Glu Ala Asn Leu Asp Lys Leu Ala
        115                 120                 125

Leu Ala Gly His Ser Arg Gly Gly His Ala Ala Phe Ala Leu Ala Leu
    130                 135                 140

Gly His Ala Glu Thr Thr Leu Lys Phe Ser Leu Leu Met Gly Ile Asp
145                 150                 155                 160

Pro Val Ala Gly Pro Ser Lys Cys Cys Gln Ile Pro Pro Lys Ile Leu
                165                 170                 175

Thr Tyr Glu Pro Ser Ser Phe Glu Leu Glu Ile Pro Val Leu Val Leu
            180                 185                 190

Gly Thr Gly Leu Gly Ser Glu Gln Lys Asn Ile Leu Phe Pro Ala Cys
        195                 200                 205

Ala Pro Asp Gly Val Asn His Lys Glu Phe Tyr Ser Glu Cys Lys Pro
    210                 215                 220

Pro Cys Tyr His Phe Val Val Thr Asp Tyr Gly His Leu Asp Met Leu
225                 230                 235                 240

Asp Asp Thr Ala Pro Lys Ile Thr Lys Cys Val Cys Lys Asn Gly Thr
                245                 250                 255

Asn Cys Arg Glu Ile Met Arg Arg Thr Thr Gly Gly Ile Met Thr Ala
            260                 265                 270

```
Phe Leu Lys Ala Tyr Leu Leu Asp Leu Glu Glu Asp Leu Lys Ala Ile
            275                 280                 285

Ala Asp Pro Gln Ile Ala Pro Thr Lys Leu Asp Pro Val Ser Tyr Arg
290                 295                 300

Leu Glu
305

<210> SEQ ID NO 5
<211> LENGTH: 326
<212> TYPE: PRT
<213> ORGANISM: Wollemia nobilis
<220> FEATURE:
<221> NAME/KEY: misc_feature
<223> OTHER INFORMATION: CHL28 putative chlorophyllase

<400> SEQUENCE: 5

Met Gly Leu Glu Asp Ile Phe Lys Glu Gly Pro Leu Pro Ile Gln Thr
1               5                   10                  15

Leu Thr Ile Pro Ala Gln Gln Arg Ala Thr Ala Thr Gly Pro Cys Cys
            20                  25                  30

His Gly Arg Ala Ser Pro Met Glu Pro Thr Ala Leu Pro Pro Lys Pro
        35                  40                  45

Leu Met Val Ile Leu Pro Ser Gln Glu Gly Asp Tyr Pro Val Leu Leu
    50                  55                  60

Tyr Leu His Gly Tyr Leu Leu Asn Ser Tyr Tyr Ser Gln Leu Leu
65                  70                  75                  80

Cys His Ile Ala Ser His Gly Tyr Ile Ala Ile Ala Pro Gln Met Tyr
                85                  90                  95

Thr Ala Ala Gly Pro Asp Ala Thr Pro Glu Ile Arg Asp Ala Val Ala
            100                 105                 110

Ile Thr Glu Trp Leu Pro Thr Gly Phe Ala Gly Arg Leu Pro Thr His
        115                 120                 125

Val Arg Pro Asp Leu Gln Lys Val Ala Val Ala Gly His Ser Arg Gly
    130                 135                 140

Gly Lys Val Ala Phe Gly Ala Ala Leu Gly Arg Ala Thr Pro Pro Pro
145                 150                 155                 160

Ser Leu Pro Tyr Ala Ala Ile Val Gly Val Asp Pro Val Asp Gly Met
                165                 170                 175

Ala Ala Gly Arg Gln Thr Pro Pro Leu Ile Leu Gly Tyr Gly Asp His
            180                 185                 190

Asp Phe Glu Asn Ser Ile Pro Ala Leu Val Ile Gly Ser Gly Leu Gly
        195                 200                 205

Pro Val Arg Arg Asn Pro Leu Phe Pro Pro Cys Ala Pro Ala Gly Val
    210                 215                 220

Asn His Val Asp Phe Phe Arg Glu Cys Arg Ala Pro Tyr His Phe
225                 230                 235                 240

Val Ala Thr Glu Tyr Gly His Gln Asp Phe Leu Asp Asp Glu Thr Gly
                245                 250                 255

Gly Val Arg Gly Arg Ala Thr Tyr Cys Leu Cys Lys Asn Gly Thr Ala
            260                 265                 270

Arg Glu Pro Met Arg Arg Phe Ala Ala Gly Ile Ile Val Ala Phe Leu
        275                 280                 285

Asn Ala Trp Leu Arg Asn Asp Ser Ala Asp Leu Glu Asp Val Leu Asp
    290                 295                 300

Pro Ser Arg Ala Pro Val Lys Met Glu Pro Pro Glu Trp Asn Leu Phe
305                 310                 315                 320
```

```
Gln Lys Val Pro Thr Leu
            325

<210> SEQ ID NO 6
<211> LENGTH: 328
<212> TYPE: PRT
<213> ORGANISM: Cucumis sativus
<220> FEATURE:
<221> NAME/KEY: misc_feature
<223> OTHER INFORMATION: CHL29 putative chlorophyllase

<400> SEQUENCE: 6

Met Ala Ala Val Val Asp Val Lys Gly Lys Ser Lys Ser Ala Ala
1               5                   10                  15

Val Ser Ser Val Val Asp Leu Asp Pro His Pro Tyr Asp Gly Val Phe
                20                  25                  30

Glu Lys Gly Lys Phe Glu Val Gly Val Ile Thr Lys Thr Thr Asp Ile
                35                  40                  45

Phe Ser Thr Ser Lys Pro Leu Leu Val Phe Thr Pro Lys Thr Pro Gly
        50                  55                  60

Leu Tyr Pro Ala Ile Leu Phe Phe His Gly Phe Ser Cys Tyr Gly Ser
65                  70                  75                  80

Phe Tyr Thr Asp Phe Leu Thr Leu Ile Ala Ser His Gly Tyr Val Ile
                85                  90                  95

Ala Ala Pro Gln Leu Tyr Val Met Pro Thr Thr Ser Glu Met Asp Glu
                100                 105                 110

Ile Lys Ser Ala Val Asp Val Ile Lys Trp Leu Ser Ser Gly Leu Asp
            115                 120                 125

Pro Leu Leu Pro Thr Asn Val Lys Gly Asp Leu Ser Lys Leu Ser Leu
        130                 135                 140

Leu Gly His Ser Arg Gly Gly Lys Thr Ala Phe Ser Leu Ala Leu Gly
145                 150                 155                 160

Trp Gly Ser Pro Ser Leu Pro Phe Ser Ala Ile Ile Gly Ile Asp Pro
                165                 170                 175

Val Ala Gly Ser Lys Phe Phe Arg Pro Glu Pro Gln Ile Leu Asp Pro
                180                 185                 190

Pro Ser Gln Pro Phe Lys Ile Ser Leu Pro Ile Thr Val Val Gly Thr
            195                 200                 205

Gly Leu Gly Pro Gln Lys Ala Thr Pro Val Thr Cys Ala Cys Ala Pro
        210                 215                 220

Asp Gly Leu Asn His Ile Ala Phe Phe Lys Lys Cys Lys Pro Thr Cys
225                 230                 235                 240

Ala His Phe Val Ala Val Asn Tyr Gly His Met Asp Ile Leu Asp Asp
                245                 250                 255

Asn Pro Pro Gly Met Thr Gly Tyr Phe Thr Asn Ile Ala Cys Lys Asn
                260                 265                 270

Gly Lys Gly Pro Arg Asp Leu Met Arg Lys Cys Cys Ser Gly Leu Val
            275                 280                 285

Val Ala Ser Leu Lys Ala Tyr Leu Asp Asn Asp Val Ser Ile Leu Asn
        290                 295                 300

Ala Ile Tyr Asp Pro Ser Ile Ala Pro Thr Glu Leu Asn Pro Val Glu
305                 310                 315                 320

Val Ile Tyr Lys Thr Pro Ser Ala
            325
```

<210> SEQ ID NO 7
<211> LENGTH: 317
<212> TYPE: PRT
<213> ORGANISM: Tarenaya hassleriana
<220> FEATURE:
<221> NAME/KEY: misc_feature
<223> OTHER INFORMATION: CHL30 putative chlorophyllase

<400> SEQUENCE: 7

```
Met Gly Glu Glu Ser Glu Arg Leu Gly Ser Ala Phe Pro Gly
1               5                   10                  15

Ser Leu Pro Thr Thr Val Ile Lys Ala Asp Pro Ser Arg Glu Asp Pro
            20                  25                  30

Val Ser Pro Pro Lys Pro Val Met Ile Val Ala Pro Thr Val Ala Gly
        35                  40                  45

Thr Tyr Pro Val Val Phe Phe His Gly Phe Tyr Leu Arg Asn Tyr
    50                  55                  60

Phe Tyr Ser Asp Val Leu Ser His Val Ala Ser His Gly Phe Ile Leu
65                  70                  75                  80

Val Ala Pro Gln Leu Cys Lys Leu Leu Pro Pro Gly Gly Gln Val Glu
                85                  90                  95

Val Asp Asp Ala Gly Lys Val Ile Asn Trp Ala Pro Tyr Leu Lys
            100                 105                 110

Ser Leu Leu Pro Gly Ser Val Lys Pro Ser Gly Glu Asp Thr Ser Leu
        115                 120                 125

Val Gly His Ser Arg Gly Gly Lys Thr Ala Phe Ala Val Ala Leu Gly
    130                 135                 140

His Ala Ser Thr Leu Asp Pro Ser Thr Lys Phe Ser Ala Leu Val Gly
145                 150                 155                 160

Ile Asp Pro Val Ala Gly Ser Asn Val Cys Met Arg Thr Gln Pro His
                165                 170                 175

Ile Leu Thr Tyr Glu Pro Glu Ser Phe Glu Leu Asp Met Pro Val Ala
            180                 185                 190

Val Val Gly Thr Gly Leu Gly Pro Lys Trp Asn Asn Val Met Pro Pro
        195                 200                 205

Cys Ala Pro Asp Gly Val Asn His Lys Glu Phe Phe Asn Glu Cys Arg
    210                 215                 220

Pro Thr Arg Ala His Phe Val Ala Ala Asp Tyr Gly His Met Asp Met
225                 230                 235                 240

Leu Asp Asp Asp Leu Glu Gly Ala Val Gly Tyr Leu Ala Gly Cys Leu
                245                 250                 255

Cys Lys Lys Gly Lys Leu Asp Lys Ser Gly Met Arg Arg Phe Val Gly
            260                 265                 270

Gly Ile Val Val Ala Phe Leu Lys Tyr Ser Val Phe Gly Asp Lys Ser
        275                 280                 285

Glu Ile Asn Ser Ile Val Lys Asp Pro Ser Leu Ser Pro Ala Arg Ile
    290                 295                 300

Asp Pro Pro Pro Gln Phe His Glu Ala Ser Ser Phe Val
305                 310                 315
```

<210> SEQ ID NO 8
<211> LENGTH: 306
<212> TYPE: PRT
<213> ORGANISM: Solanum tuberosum
<220> FEATURE:
<221> NAME/KEY: misc_feature
<223> OTHER INFORMATION: CHL31 putative chlorophyllase

```
<400> SEQUENCE: 8

Met Val His Gly Lys Ala Ser Ile Glu Arg Asn Ile Lys Met Gly Ala
1               5                   10                  15

Ser Ser Ile Phe Glu Ile Gly Asn Glu Thr Ile Asn Thr Ile Asn Val
            20                  25                  30

Lys Ser Ser Ser Leu Pro Cys Ser Leu Leu Val Phe Ser Pro Thr
        35                  40                  45

Thr Lys Gly Ser Tyr Pro Val Leu Leu Phe His Gly Phe Met Leu
    50                  55                  60

Gln Pro Ser Trp Tyr Lys Ser Leu Leu Gln His Ile Ser Ser His Arg
65                  70                  75                  80

Tyr Ile Ile Val Ala Pro Gln Phe Pro Leu Ile Asn Leu Gln Glu Met
                85                  90                  95

Lys Asn Val Arg Lys Ile Ala Glu Trp Leu Ile Asn Asn Leu Lys Ser
            100                 105                 110

Val Val Pro Glu Lys Val Gln Pro Asp Leu Glu Lys Val Ala Ile Ser
        115                 120                 125

Gly His Ser Lys Gly Gly Asn Thr Ala Phe Ala Val Ala Phe Asp Ser
    130                 135                 140

Ser Met Pro Leu Lys Phe Ser Ala Leu Leu Gly Ile Glu Pro Val Ala
145                 150                 155                 160

Gly Thr Ser Thr Ser Cys Leu Cys Pro Tyr Val Leu Glu Tyr Ile
                165                 170                 175

Pro Arg Ile Phe Asn Gln Ser Ile Pro Val Ala Val Leu Gly Ala Gly
                180                 185                 190

Leu Ser Asn Gln Ser Thr Cys Cys Leu Leu Gln Ser Val Ala Pro Asn
        195                 200                 205

Gly Val Asn His Ala Glu Phe Phe Asn Glu Ser Lys Pro Pro Cys Tyr
            210                 215                 220

Tyr Phe Met Ala Lys Asp Tyr Gly His Ala Asp Met Leu Glu Ala Glu
225                 230                 235                 240

Gly Ile Met Ala Ile Leu Ile Arg Ile Leu Met Lys Ser Gly Lys Gly
                245                 250                 255

Ser Lys Asp Ser Met Ile Arg Ala Val Gly Gly Ile Val Val Ala Phe
            260                 265                 270

Leu Lys Ala Tyr Leu Glu Gly Gln Ile Asp Asp Leu Asn Asp Ile Val
        275                 280                 285

Lys Ser Pro Asn Leu Ala Pro Ile Thr Leu Asp Pro Val Ile Ser Ile
    290                 295                 300

Lys Asp
305

<210> SEQ ID NO 9
<211> LENGTH: 343
<212> TYPE: PRT
<213> ORGANISM: Populus trichocarpa
<220> FEATURE:
<221> NAME/KEY: misc_feature
<223> OTHER INFORMATION: CHL32 putative chlorophyllase

<400> SEQUENCE: 9

Met Ala Ala Ile Glu Asp Ser Pro Thr Phe Ser Ser Val Val Thr Pro
1               5                   10                  15

Ala Ala Phe Glu Ile Gly Ser Leu Pro Thr Thr Glu Ile Pro Val Asp
            20                  25                  30
```

Pro Val Glu Asn Asp Ser Thr Ala Pro Pro Gly Ser Leu Leu Ile Phe
            35                  40                  45

Arg Pro Glu Glu Lys Gly Thr Tyr Pro Val Ile Leu Phe His His Gly
 50                  55                  60

Thr Gly Cys Gln Asn Ser Trp Tyr Thr Asp Val Phe Lys Phe Ile Ser
 65                  70                  75                  80

Ser His Gly Tyr Ile Val Ala Pro Gln Leu Tyr Gly Leu Met Pro
                85                  90                  95

Pro Ser Gly Gln Asp Glu Leu Asp Leu Ala Ala Glu Val Ala Asn Trp
            100                 105                 110

Leu Pro Ser Gly Leu Arg Cys Val Leu Pro Glu Asp Ile Glu Gly Asp
            115                 120                 125

Ile His Asn Leu Ala Leu Ala Gly His Ser Arg Gly Gly Tyr Ile Ala
130                 135                 140

Phe Ala Leu Ala Leu Gly Leu Ala Asp Val Ser Leu Asp Val Asp Phe
145                 150                 155                 160

Ser Ala Leu Ile Gly Val Asp Pro Val Ala Gly Thr Ser Lys Thr Asn
                165                 170                 175

Gln Met Glu Pro Lys Ile Leu Asn Tyr Glu Ser Cys Ser Phe Asn Phe
            180                 185                 190

Ser Ile Pro Val Ala Ile Ile Gly Thr Gly Leu Gly Asn Lys Pro Ala
        195                 200                 205

Cys Pro Ile Ile Arg Gln Thr Cys Ala Pro Asp Gly Val Ser His Thr
        210                 215                 220

Glu Ile Phe Asn Glu Cys Lys Pro Pro Cys Ser His Phe Val Thr Thr
225                 230                 235                 240

Asp Tyr Gly His Met Asp Val Leu Asp Asp Ile Gly Leu Ile Gly
                245                 250                 255

Glu Gly Ala Arg Ala Met Cys Lys Gly Ser Arg Arg Gly Val Ser Arg
            260                 265                 270

Asp Pro Met Arg Arg Thr Val Gly Gly Val Ser Val Ala Phe Leu Glu
            275                 280                 285

Ala Phe Phe Lys Gly Asn Tyr Thr Asp Tyr Asn Lys Ile Leu Lys Ser
290                 295                 300

Asn Tyr Phe Ala Pro Thr Thr Leu Asp Pro Val Gln Asn Lys Ser Glu
305                 310                 315                 320

Gly Thr Ser Ser Ser Leu Ser Ala Met Ser Met Pro Ala Thr Leu
            325                 330                 335

Asp Trp His Ile Asp Glu Leu
            340

<210> SEQ ID NO 10
<211> LENGTH: 318
<212> TYPE: PRT
<213> ORGANISM: Vigna radiata
<220> FEATURE:
<221> NAME/KEY: misc_feature
<223> OTHER INFORMATION: CHL33 putative chlorophyllase

<400> SEQUENCE: 10

Met Ala Ala Ile Glu Asp Ser Pro Thr Phe Ser Ser Val Val Thr Pro
1               5                   10                  15

Ala Ala Phe Glu Ile Gly Ser Leu Pro Thr Thr Glu Ile Pro Val Asp
            20                  25                  30

Pro Val Glu Asn Asp Ser Thr Ala Pro Pro Lys Pro Leu Leu Ile Phe
            35                  40                  45

Thr Pro Thr Val Pro Gly Ala Tyr Pro Val Ile Leu Phe Cys His Gly
            50                  55                  60

Phe Phe Val Pro Asn Thr Phe Tyr Ser His Leu Leu Thr His Ile Val
 65                  70                  75                  80

Ser His Gly Phe Ile Leu Val Ala Pro Gln Leu Phe Cys Lys Gly Leu
                85                  90                  95

Pro Met Leu Glu Pro Ser Glu Val Lys Phe Ala Gly Lys Val Ala Asp
            100                 105                 110

Trp Leu Ala Glu Gly Leu Gln Pro Leu Pro Glu Asn Val Glu Ala
            115                 120                 125

Asn Leu Glu Lys Leu Val Val Ser Gly His Ser Lys Gly Gly Lys Thr
            130                 135                 140

Ala Phe Cys Val Ala Leu Gly Tyr Ala Lys Thr Lys Leu Lys Phe Ser
145                 150                 155                 160

Ala Leu Val Gly Ile Asp Pro Val Ala Gly Thr Ser Lys Tyr Cys Glu
                165                 170                 175

Thr Asn Pro His Ile Leu Lys Gly Val Pro Gly Ser Phe Asn Leu Asn
            180                 185                 190

Met Pro Val Ala Val Ile Gly Ser Glu Leu Gly Pro Lys Lys Gly Asn
            195                 200                 205

Cys Cys Ser Pro Pro Cys Ala Pro Asp Gly Met Asn His Lys Glu Phe
210                 215                 220

Phe Lys Glu Cys Lys Pro Pro Ser Ala His Phe Val Val Ala Arg Tyr
225                 230                 235                 240

Gly His Met Asp Met Leu Asp Asp Glu Thr Ala Gly Val Ile Gly Thr
                245                 250                 255

Leu Leu Ser Lys Cys Ala Cys Lys Asn Gly Ser Gly Pro Arg Asp Leu
            260                 265                 270

Met Arg Arg Thr Ile Gly Gly Leu Val Val Ala Phe Leu Arg Ala Gln
            275                 280                 285

Leu Asn Asp His Trp Lys Asp Phe Asp Ala Ile Leu Asn Pro Asn Ile
            290                 295                 300

Ala Pro Thr Gln Leu Asp Asn Met Val Tyr Ile Pro Ala Ser
305                 310                 315

<210> SEQ ID NO 11
<211> LENGTH: 236
<212> TYPE: PRT
<213> ORGANISM: Artificial Sequence
<220> FEATURE:
<223> OTHER INFORMATION: Green fluorescent protein

<400> SEQUENCE: 11

Met Thr Ala Leu Thr Glu Gly Ala Lys Leu Phe Glu Lys Glu Ile Pro
 1               5                  10                  15

Tyr Ile Thr Glu Leu Glu Gly Asp Val Glu Gly Met Lys Phe Ile Ile
                20                  25                  30

Lys Gly Glu Gly Thr Gly Asp Ala Thr Thr Gly Thr Ile Lys Ala Lys
            35                  40                  45

Tyr Ile Cys Thr Thr Gly Asp Leu Pro Val Pro Trp Ala Thr Leu Val
        50                  55                  60

Ser Thr Leu Ser Tyr Gly Val Gln Cys Phe Ala Lys Tyr Pro Ser His
 65                  70                  75                  80

Ile Lys Asp Phe Phe Lys Ser Ala Met Pro Glu Gly Tyr Thr Gln Glu
                85                  90                  95

```
Arg Thr Ile Ser Phe Glu Gly Asp Gly Val Tyr Lys Thr Arg Ala Met
                100                 105                 110

Val Thr Tyr Glu Arg Gly Ser Ile Tyr Asn Arg Val Thr Leu Thr Gly
            115                 120                 125

Glu Asn Phe Lys Lys Asp Gly His Ile Leu Arg Lys Asn Val Ala Phe
        130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175

Glu Lys Leu Val Thr Lys Cys Ser Gln Met Asn Arg Pro Leu Ala Gly
            180                 185                 190

Ser Ala Ala Val His Ile Pro Arg Tyr His His Ile Thr Tyr His Thr
        195                 200                 205

Lys Leu Ser Lys Asp Arg Asp Glu Arg Arg Asp His Met Cys Leu Val
210                 215                 220

Glu Val Val Lys Ala Val Asp Leu Asp Thr Tyr Gln
225                 230                 235
```

<210> SEQ ID NO 12
<211> LENGTH: 301
<212> TYPE: PRT
<213> ORGANISM: Chlamydomonas reinhardtii
<220> FEATURE:
<221> NAME/KEY: misc_feature
<223> OTHER INFORMATION: P2 pyropheophytinase

<400> SEQUENCE: 12

```
Met Ser Asp Asp Tyr Ile Lys Arg Gly Asp Leu Pro Thr Ser Lys Trp
1               5                   10                  15

Ser Gly Arg Val Thr Leu Arg Val Asp Ser Ala Met Ala Val Pro Leu
            20                  25                  30

Asp Val Val Ile Thr Tyr Pro Ser Ser Gly Ala Ala Ala Tyr Pro Val
        35                  40                  45

Leu Val Met Tyr Asn Gly Phe Gln Ala Lys Ala Pro Trp Tyr Arg Gly
50                  55                  60

Ile Val Asp His Val Ser Ser Trp Gly Tyr Thr Val Val Gln Tyr Thr
65                  70                  75                  80

Asn Gly Gly Leu Phe Pro Ile Val Val Asp Arg Val Glu Leu Thr Tyr
                85                  90                  95

Leu Glu Pro Leu Leu Thr Trp Leu Glu Thr Gln Ser Ala Asp Ala Lys
            100                 105                 110

Ser Pro Leu Tyr Gly Arg Ala Asp Val Ser Arg Leu Gly Thr Met Gly
        115                 120                 125

His Ser Arg Gly Gly Lys Leu Ala Ala Leu Gln Phe Ala Gly Arg Thr
    130                 135                 140

Asp Val Ser Gly Cys Val Leu Phe Asp Pro Val Asp Gly Ser Pro Met
145                 150                 155                 160

Thr Pro Glu Ser Ala Asp Tyr Pro Ser Ala Thr Lys Ala Leu Ala Ala
                165                 170                 175

Ala Gly Arg Ser Ala Gly Leu Val Gly Ala Ile Thr Gly Ser Cys
            180                 185                 190

Asn Pro Val Gly Gln Asn Tyr Pro Lys Phe Trp Gly Ala Leu Ala Pro
        195                 200                 205

Gly Ser Trp Gln Met Val Leu Ser Gln Ala Gly His Met Gln Phe Ala
```

-continued

```
                210                 215                 220
Arg Thr Gly Asn Pro Phe Leu Asp Trp Ser Leu Asp Arg Leu Cys Gly
225                 230                 235                 240

Arg Gly Thr Met Met Ser Ser Asp Val Ile Thr Tyr Ser Ala Ala Phe
                245                 250                 255

Thr Val Ala Trp Phe Glu Gly Ile Phe Arg Pro Ala Gln Ser Gln Met
            260                 265                 270

Gly Ile Ser Asn Phe Lys Thr Trp Ala Asn Thr Gln Val Ala Ala Arg
        275                 280                 285

Ser Ile Thr Phe Asp Ile Lys Pro Met Gln Ser Pro Gln
    290                 295                 300

<210> SEQ ID NO 13
<211> LENGTH: 21
<212> TYPE: DNA
<213> ORGANISM: Artificial Sequence
<220> FEATURE:
<223> OTHER INFORMATION: SpeI site and ribosome binding site

<400> SEQUENCE: 13
actagtagga ggtaactaat g                                            21

<210> SEQ ID NO 14
<211> LENGTH: 12
<212> TYPE: DNA
<213> ORGANISM: Artificial Sequence
<220> FEATURE:
<223> OTHER INFORMATION: stop codon and XhoI site

<400> SEQUENCE: 14
tgatgactcg ag                                                      12
```